(12) United States Patent
Jiang et al.

(10) Patent No.: US 11,866,704 B2
(45) Date of Patent: Jan. 9, 2024

(54) NUCLEIC ACID MOLECULES AND USES THEREOF

(71) Applicant: Macau University of Science and Technology, Macau (CN)

(72) Inventors: Zhi-Hong Jiang, Macau (CN); Kai-Yue Cao, Macau (CN); Yu Pan, Macau (CN); Tong-Meng Yan, Macau (CN)

(73) Assignee: Macau University of Science and Technology, Macau (CN)

( * ) Notice: Subject to any disclaimer, the term of this patent is extended or adjusted under 35 U.S.C. 154(b) by 249 days.

(21) Appl. No.: 17/247,265

(22) Filed: Dec. 6, 2020

(65) Prior Publication Data

US 2021/0254066 A1 Aug. 19, 2021

(30) Foreign Application Priority Data

Feb. 10, 2020 (CN) .......................... 202010083971 .2

(51) Int. Cl.
*C12N 15/113* (2010.01)
(52) U.S. Cl.
CPC ........ *C12N 15/113* (2013.01); *C12N 2310/14* (2013.01); *C12N 2310/32* (2013.01)
(58) Field of Classification Search
CPC .......................... C12N 15/113; C12N 2310/14
See application file for complete search history.

(56) References Cited

FOREIGN PATENT DOCUMENTS

| WO | WO-03106631 A2 | * | 12/2003 | ........... C12N 15/111 |
| WO | WO-2004046375 A2 | * | 6/2004 | ............... C12Q 1/04 |

OTHER PUBLICATIONS

Ahmed et al. PLoS One 6(8): e23443, pp. 1-8 (Year: 2011).*
Mlotshwa, S., et al.(2015). A novel chemopreventive strategy based on therapeutic microRNAs produced in plants. Cell research, 25(4), 521-524.
Goodarzi, H., et al.(2015). Endogenous tRNA-derived fragments suppress breast cancer progression via YBX1 displacement. Cell, 161(4), 790-802.

* cited by examiner

*Primary Examiner* — Brian Whiteman
(74) *Attorney, Agent, or Firm* — EAGLE IP LIMITED

(57) ABSTRACT

A method of treating a subject suffering from cancer comprising a step of administering an effective amount of a group of double-stranded RNA molecules to the subject, wherein the RNA molecule is isolated or derived from a bacteria of the genus *Escherichia*. A method of inhibiting growth or proliferation of cancer cells comprising a step of contacting said cells with said RNA molecule; and a pharmaceutical composition for treating cancer comprising said RNA molecule and a pharmaceutically tolerable excipient. Also a double-stranded RNA molecule and a recombinant vector comprising the double-stranded RNA molecule.

16 Claims, 9 Drawing Sheets

Specification includes a Sequence Listing.

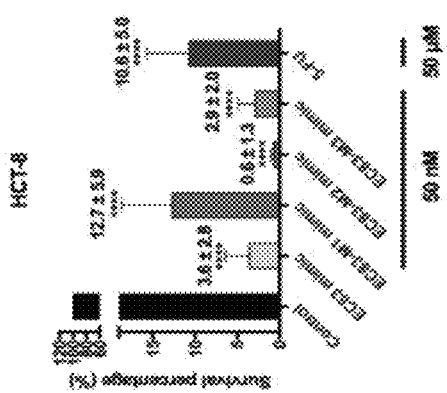 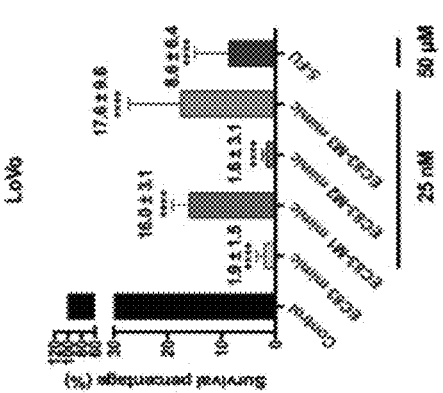
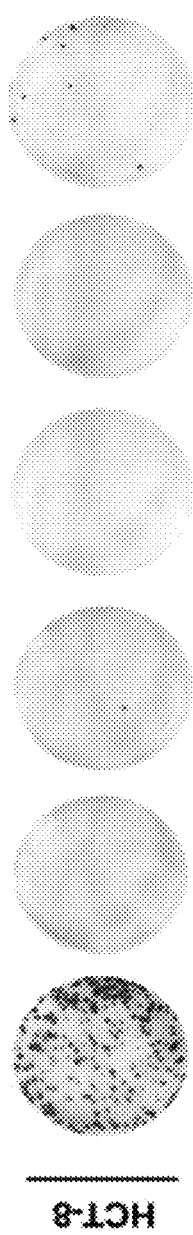 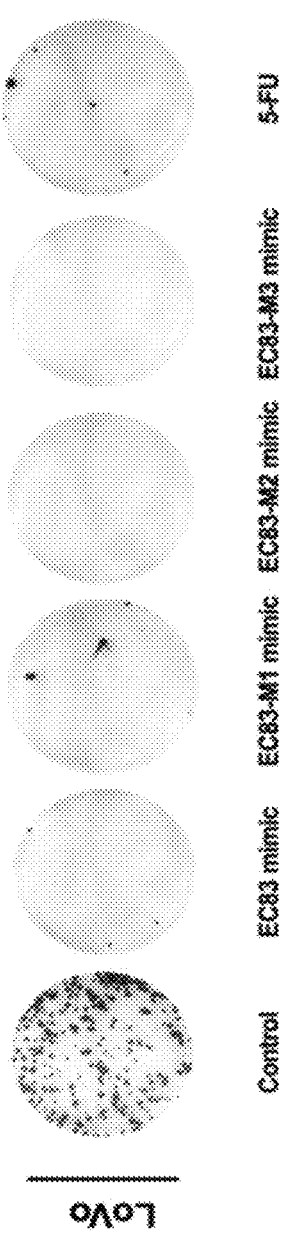
FIG. 8A
FIG. 8B

NUCLEIC ACID MOLECULES AND USES THEREOF

CROSS-REFERENCE TO RELATED APPLICATION

This application claims priority to, and the benefit of, Chinese Patent Application No. 202010083971.2 filed on Feb. 10, 2020. The entire contents of the foregoing application are hereby incorporated by reference for all purposes.

REFERENCE TO SEQUENCE LISTING

This application contains a sequence listing which has been submitted electronically in ASCII format and is hereby incorporated by reference in its entirety. Said ASCII copy, created on Jul. 25, 2022, is named "M006_092_NPRUS_Sequence_list_revised.txt" and is 83 kilobytes in size.

TECHNICAL FIELD

The present invention relates to a method of treating a subject suffering from cancer by administering a nucleic acid to the subject. Said nucleic acid is in particular but not exclusively a RNA molecule. The invention further relates to a pharmaceutical composition comprising a nucleic acid for the treatment and use thereof.

BACKGROUND OF THE INVENTION

Cancer has become the most common disease causing death worldwide.

Traditional Chinese medicines (TCMs) have been applied for treating and preventing cancer whereas lots of research efforts have been contributed to investigate the effectiveness of isolated small molecules such as alkaloids, terpenoids, flavonoids or the like in treating cancer. Some alkaloids are found to have effect in inhibiting cancer such as by enhancing the efficacy of an anti-cancer drug. However, most of them are often toxic to human. Also, macromolecules such as DNAs, RNAs, and proteins are generally considered unstable and have poor effect in living human body and therefore have not been widely considered as suitable in said treatment.

Currently, some studies show that non-coding RNAs (ncRNAs) such as microRNAs have diverse regulatory roles through targeting different aspects of RNA transcription or post-transcription process in nearly all eukaryotic organisms. Mlotshwa, S. et al. (Cell research 2015, 25 (4), 521-4) suggested that exogenous plant microRNAs in foods could be taken up by the mammalian digestive tract and trafficked via the bloodstream to a variety of tissue cells, where they are capable of regulating the expression of mammalian genes. Goodarzi, H. et al. (Cell 2015, 161 (4), 790-802) revealed that endogenous tRNA derived fragments could suppress the stability of multiple oncogenic transcripts in breast cancer cells through binding and antagonizing activities of pathogenesis-related RNA-binding proteins.

*Escherichia coli* (Migula) Castellani & Chalmers, a species from the genus *Escherichia* that belong to the family of Enterobacteriaceae. It is a famous gut microbiota mainly distributed in the colon of human beings and animals, which possess almost 0.1% of gut microorganisms. Non-pathogenic *Escherichia coli* as a part of normal bacteria in human gut intestinal can produce vitamin K, as well as avoiding the progression of other pathogenic strains, which is beneficial to the human beings. Nevertheless, there still remains a need to derive effective molecules from various sources such as human gut microbiota for treatments.

SUMMARY OF THE INVENTION

According to the limitations of current techniques, through lots of experiments and investigations, the inventors successfully separated and purified tRNA-derived fragments from bacteria of the genus *Escherichia* for cancer prevention and/or treatment, especially for the double-stranded RNA molecules containing antisense from SEQ ID NO: 1 to 3 and sense from SEQ ID NO: 4 to 6, which provides a novel and effective method for preventing and/or treating cancer.

In a first aspect, the invention provides a group of double-stranded RNA molecules comprising an antisense sequence selected from SEQ ID NO: 7 to SEQ ID NO: 100 and a sense sequence selected from SEQ ID NO: 101 to SEQ ID NO: 194, or a functional variant or homologue therefore.

Preferably, the said double-stranded RNA molecules or a functional variant or homologue therefore comprising an antisense sequence selected from SEQ ID NO: 47, 48, 89, 90, 91 and 92, and a sense sequence selected from SEQ ID NO: 141, 142, 183, 184, 185 and 186.

In a further aspect, the antisense sequence of said double-stranded RNA molecules or a functional variant or homologue therefore is shown as SEQ ID NO: 47, 48, 89, 90, 91 and 92, and the sense sequence of said double-stranded RNA molecules or a functional variant or homologue therefore is shown as SEQ ID NO: 141, 142, 183, 184, 185 and 186.

Still further, the antisense sequence of said double-stranded RNA molecules or a functional variant or homologue therefore is shown as SEQ ID NO: 89, and the sense sequence of said double-stranded RNA molecules or a functional variant or homologue therefore is shown as SEQ ID NO: 183.

Preferably, the said double-stranded RNA molecules or a functional variant or homologue therefore comprising a 3' overhang.

Preferably, the said double-stranded RNA molecules or a functional variant or homologue therefore comprising one or more preferably modified nucleotides. The said nucleotides comprising m1A, m2A, m5A, m7A, m2G, m6A, m22G, Um, i6A, ms2i6A, t6A, m6t6A, s2C, s2U, s4U, ac4C, f5C, acp3U, mo5U, cmo5U, mcmo5U, mcm5U, mcm5Um, mcm5s2U, nm5s2U, mnm5U, mnm5s2U, ncm5U, ncm5Um, cmnm5U, cmnm5Um, cmnm5s2U, tm5U and tm5s2U. Preferably, said chemical modifications comprising one or more selected from m1A, m7G, m6A, Gm, Cm, Am, Um, m22G, s4U and cmo5U. Preferably, the said chemical modified nucleotides comprising uridine or guanosine. In a further aspect, the said chemical modified nucleotides comprising s4U and/or Gm. Still further, the said double-stranded RNA molecules or a functional variant or homologue therefore comprising an antisense sequence selected from SEQ ID NO: 1, 2 and 3, and a sense sequence selected from SEQ ID NO: 4, 5 and 6. Most preferably, the said double-stranded RNA molecules or a functional variant or homologue therefore is shown as SEQ ID NO: 1, 2 and 3, and a sense sequence is shown as SEQ ID NO: 4, 5 and 6.

In a further aspect, the invention provides to a pharmaceutical composition for cancer prevention and/or treatment. The pharmaceutical composition comprises the said double-stranded RNA molecules or a functional variant or homologue therefore and pharmaceutically tolerable carrier, diluent and/or excipient.

Preferably, the said pharmaceutical composition comprises the said nucleic acid stabilizer.

In a further aspect, the invention provides a delivery system for cancer prevention and/or treatment, which comprises the said double-stranded RNA molecules or a functional variant or homologue therefore and pharmaceutically tolerable carrier, diluent and/or excipient.

In another aspect, the invention provides the use of the said double-stranded RNA molecules or a functional variant or homologue therefore in preparation of pharmaceutical composition for cancer prevention and/or treatment.

Correspondingly, the invention provides a method for cancer prevention and treatment, said method comprising administrating an effective amount of said double-stranded RNA molecules or a functional variant or homologue therefore to objects for cancer prevention and/or treatment.

In the mentioned pharmaceutical composition, delivery system, use or method, said cancer prevention and/or treatment can be inhibiting growth, proliferation or migration of cancer cells.

According to an embodiment, in the mentioned pharmaceutical composition, delivery system, use or method, said cancer prevention and/or treatment is colorectal cancer prevention and/or treatment. Preferably, said cancer prevention and/or treatment is inhibiting colorectal cancer cells. Preferably, cancer prevention and/or treatment is fluorouracil-resistant cancer.

The inventors have found that non-coding RNA molecules isolated from a bacteria of the genus *Escherichia*, particularly transfer RNA molecules, and RNA molecules derived from *Escherichia* are particularly useful in treatment of cancer. The RNA molecules with a sequence length of about 10 to 200 nucleotides and their homologue double-stranded RNA molecules with a sequence length of about 10 to 30 nucleotides are highly effective in inhibiting growth and proliferation of cancer cells in vitro and exhibit an antitumor effect in vivo. Said RNA molecules are also effective against fluorouracil-resistant cell lines. Further, the pharmaceutical composition comprising the RNA molecule that is isolated or derived from a bacteria of the genus *Escherichia* and a pharmaceutically tolerant excipient can act directly on the cancer cells or tumor, and therefore can have a faster-acting therapeutic effect.

Those skilled in the art will appreciate that the invention described herein is susceptible to variations and modifications other than those specifically described.

The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 8A shows the inhibition effects of RNA molecule EC83 mimic, EC83-M1 mimic, EC83-M2 mimic and EC83-M3 mimic derived from *Escherichia coli* (Migula) Castellani & Chalmers at a dose of 50 nM on the proliferation of HCT-8 cells in accordance with an example embodiment (mean±SD n=3; ****, p<0.0001 vs. vehicle control).

FIG. 8B shows the inhibition effects of RNA molecule EC83 mimic, EC83-M1 mimic, EC83-M2 mimic and EC83-M3 mimic derived from *Escherichia coli* (Migula) Castellani & Chalmers at a dose of 25 nM on the proliferation of LoVo cells in accordance with an example embodiment (mean±SD n=3; ****, p<0.0001 vs. vehicle control).

DETAILED DESCRIPTION OF THE EMBODIMENTS

Figure 1A:
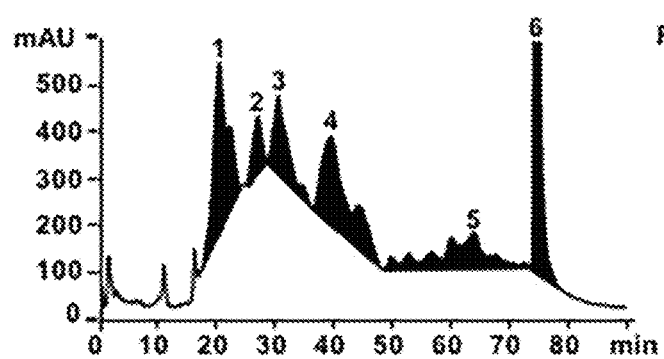
FIG. 1A shows chromatogram under UV 260 nm of mixed tRNA separated by high-performance weak-anion exchange chromatographic method in accordance with an example embodiment.

Unless otherwise defined, all technical terms used herein have the same meaning as commonly understood by one skilled in the art to which the invention belongs.

As used herein and in the claims, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

As used herein and in the claims, the singular forms of "a" and "an" also include the corresponding plurals unless the context clearly dictates otherwise.

The present invention in the first aspect provides a method of treating a subject suffering from cancer. The method comprises a step of administering an effective amount of a RNA molecule to said subject. The RNA molecule administered according to the present invention may be naturally present, modified or artificially synthesized according to the sequences disclosed in the present invention, and preferably the RNA molecule is isolated or derived from a bacteria of the genus *Escherichia*. The RNA molecule of the present invention is not provided in the form of boiled extract obtained from the plant such as decoction, as it would be appreciated that RNA molecule is susceptible to spontaneous degradation at elevated temperature, alkaline pH, and the presence of nucleases or divalent metal ions. In an embodiment, the RNA molecule of the present invention is provided together with a gene delivery carrier which will be described in detail later. The RNA molecule of the present invention has a sequence length of from about 10 to 200 nucleotides which can be regarded as a small RNA molecule. Preferably, the RNA molecule has a sequence length of from about 50 to about 200 nucleotides, from about 60 to about 150 nucleotides, in particular from about 70 to about 100 nucleotides.

The RNA molecule of the present invention comprises a sequence selected from SEQ ID NO: 195 to SEQ ID NO: 241 or a functional variant or homologue thereof. The term "functional variant" of the RNA molecule refers to a molecule substantially similar to said RNA molecule with one or more sequence alterations that do not affect the biological activity or function of the RNA molecule. The alterations in sequence that do not affect the functional properties of the resultant RNA molecules are well known in the art. For example, nucleotide changes which result in alteration of the −5'-terminal and −3'-terminal portions of the molecules would not be expected to alter the activity of the polynucleotides. In an embodiment, the RNA molecule of the present invention comprises at least one modified nucleoside selected from inosine, 1-methyladenosine, 2-methyladenosine, N6-methyladenosine, N6-isopentenyladenosine, 2'-Omethyladenosine, N6-acetyladenosine, 1-methylinosine, pseudouridine, dihydrouridine, or 2-methylthio-N6-methyladenosine. In another embodiment, the RNA molecule comprises at least one nucleotide having one or more chemical modifications. In some embodiments, the one or more chemical modifications is selected from the group consisting of 1-methyl, 2-methyl, 5-methyl, 7-methyl, N2 methyl, N6 methyl, N2,N2 dimethyl, 2'-O-methyl, N6-isopentenyl, 2-methylthio-N6-isopentenyl, N6 threonide carbamoyl, N6-methyl-N6-threosylcarbamoyl, 2-thio, 4-thio, N4 acetyl, 5-formyl, 3-(3-amino-3-carboxypropyl), 5-methoxy, 5-oxoacetic acid, 5-oxoacetate methyl ester, 5-methoxycarbonylmethyl, 5-methoxycarbonylmethyl-2'-O-methyl, 5-methoxycarbonylmethyl-2-thio, 5-aminomethyl-2-thio, 5-methylaminomethyl, 5-methylaminomethyl-2-thio, 5-aminoformylmethyl, 5-aminoformylmethyl-2'-O-methyl, 5-carboxymethyl aminomethyl, 5-carbamoylmethyl-2'-O-methyl, 5-carboxymethylaminomethyl-2-methyl, 5-taurine, 5,2'-O-dimethyl, and 5-tauromethyl-2-thio.

In particular, the functional variant of the RNA molecule has at least 80%, 81%, 82%, 83%, 84%, 85%, 86%, 87%, 88%, 89%, 90%, 91%, 92%, 93%, 94%, 95%, 96%, 97%, 98%, or 99% overall sequence identity to the non-variant RNA molecule according to the present invention.

The term "homologue" used herein refers to nucleotides having a sequence identity of at least 50%, at least 60%, at least 70%, at least 80%, at least 90% or at least 95% to the RNA molecules according to the present invention. In an embodiment, the homologue of the RNA molecule has at least 90%, 91%, 92%, 93%, 94%, 95%, 96%, 97%, 98%, or 99% overall sequence identity to the RNA molecule.

Unless otherwise indicated, the term "thereof" in the term "functional variant or homologue thereof" as used herein in the claims refers to each and every member of the entire group(s) or list(s) preceding the term in the claim. For example, in a claim that claims "an antisense sequence selected from one of SEQ ID NO: 7 to SEQ ID NO: 100 and a sense sequence selected from one of SEQ ID NO: 101 to SEQ ID NO: 194; or a functional variant or homologue thereof", the group of double-stranded RNA molecules covered by the claim includes functional variants or homologs of all the sequences from SEQ ID NO: 7 to SEQ ID NO: 100, and functional variants or homologs of all the sequences from SEQ ID NO: 101 to SEQ ID NO: 194.

In an embodiment, the RNA molecule is a non-coding molecule preferably selected from a transfer RNA molecule, a ribosomal RNA molecule, a micro RNA molecule, a siRNA molecule, or a piwi-interacting RNA molecule; and more preferably is a transfer RNA molecule. tRNA molecules are highly conserved RNAs with function in various cellular processes such as reverse transcription, porphyrin biosynthesis or the like. In a particular embodiment, the double-stranded RNA molecule of the invention comprises an antisense sequence selected from SEQ ID NO: 7 to SEQ ID NO: 100 or a functional variant or homologue thereof; or the RNA molecule comprises a sense sequence selected from SEQ ID NO: 101 to SEQ ID NO: 194 or a functional variant or homologue thereof; or the RNA molecule consists of a sequence selected from SEQ ID NO: 7 to SEQ ID NO: 100 or SEQ ID NO: 101 to SEQ ID NO: 194 or a functional variant or homologue thereof.

In an alternative embodiment where the RNA molecule is a small RNA molecule having a sequence length of from about 10 to about 30 base pairs, from about 15 to about 25 base pairs, from about 19 to about 22 base pairs, 19 base pairs or 22 base pairs.

In an alternative embodiment, the RNA molecule or a functional variant or homologue thereof comprises a sequence selected from SEQ ID NO: 195 to SEQ ID NO: 241, in particular SEQ ID NO: 218 or SEQ ID NO: 237; or consists of a sequence selected from SEQ ID NO: 195 to SEQ ID NO:241, in particular SEQ ID NO: 218 to SEQ ID NO: 237. Preferably, the RNA molecule is a double-stranded RNA molecule having an antisense sequence selected from SEQ ID NO: 7 to SEQ ID NO: 100 or a functional variant or homologue thereof, and a complementary sense sequence. The antisense sequence is complementary to the sense sequence and the antisense sequence is preferably derived from SEQ ID NO: 195 to SEQ ID NO: 241 or functional variant or homologue thereof. Preferably, said double-stranded RNA molecule comprises an antisense sequence selected from SEQ ID NO: 47, 48, 89, 90, 91 or 92, and said double-stranded RNA molecule comprises an sense sequence selected from SEQ ID NO: 141, 142, 183, 184, 185 or 186; Preferably, said double-stranded RNA molecule comprises an antisense sequence shown as SEQ ID NO: 89, and said double-stranded RNA molecule comprises a sense sequence shown as SEQ ID NO: 183. In particular, RNA molecule is chemically modified double-stranded RNA molecule or functional variant or homologue thereof, and comprises an antisense sequence selected from SEQ ID NO: 1 to SEQ ID NO: 3, and comprises a complementary sense sequence selected from SEQ ID NO: 4 to SEQ ID NO: 6 in accordance with an example embodiment. The inventors unexpectedly found that the double-stranded RNA molecules of the present invention are particularly useful in treatment of cancer such as fluorouracil-resistant cancer as described in detail below.

The RNA molecule of the present invention is preferably isolated or derived from the bacteria of the genus *Escherichia*. The bacteria of the genus *Escherichia* include and only include *Escherichia coli* (Migula) Castellani & Chalmers. In an example embodiment, RNA molecule is isolated or derived from *Escherichia coli* (Migula) Castellani & Chalmers.

In more detail, the preferred sequences of the RNA molecules and double-stranded RNA molecules of the present invention are listed in Tables 1 and 3 below. In an embodiment, RNA molecules of SEQ ID NO: 195 to 241 as shown in Table 1 are isolated from a bacteria of genus *Escherichia* in particular from *Escherichia coli* (Migula) Castellani & Chalmers. These sequences are obtained by purification of RNA from *Escherichia coli* (Migula) Castellani & Chalmers. One possible approach to obtain the RNA molecules from a particular bacteria *Escherichia coli* (Migula) Castellani & Chalmers is illustrated in Example 1. It would be appreciated that other suitable methods for obtaining the isolated and purified RNA molecules of the present invention according to the disclosure herein can be applied, and the methods can be subject to appropriate modification to obtain an improved yield of the RNA molecules, without departing from the scope of the present invention.

TABLE 1

RNA molecules in particular tRNAs isolated from *Escherichia coli* (Migula) Castellani & Chalmers according to the present invention.

| SEQ ID NO. | tRNA | Sequence (5'-3') |
|---|---|---|
| 195 | tRNA-Ala(UGC) | GGGGGCA[s4U]AGCUCAGCDGGGAGAGCGCCUGCUU[cmo5U]GCACGCAGGAG[m7G]UCUGCGGTΨCGAUCCCGCGCGCUCCCACCA |
| 196 | tRNA-Ala(UGC) | GGGGCUAUAGCUCAGCDGGGAGAGCGCCUGCUU[cmo5U]GCACGCAGGAG[m7G]UCUGCGGTΨCGAUCCCGCAUAGCUCCACCA |
| 197 | tRNA-Ala(GGC) | GGGGCUANAGCUCAGCDGGGAGAGCGCUUGCAUGGCAUGCAAGAG[m7G]UCAGCGGTΨCGAUCCCGCUUAGCUCCACCA |
| 198 | tRNA-Arg(CCG) | GCGCCCGUAGCUCAGCDGGADAGAGCGCUGCC[s2C]UCCG[m1G]AGGCAGAG[m7G]UCUCAGGTΨCGAAUCCUGUCGGGCGCGCCA |
| 199 | tRNA-Arg(ICG) | GCAUCCG[s4U]AGCUCAGCDGGDAGAGUACUCGG[s2C]UICG[m2A]ACCGAGCG[m7G][acp3U]CGGAGGTΨCGAAUCCUCCCGGAUGCACCA |
| 200 | tRNA-Arg(ICG) | GCAUCCG[s4U]AGCUCAGCDGGADAGAGUACUCGGCUICG[m2A]ACCGAGCG[m7G][acp3U]CGGAGGTΨCGAAUCCUCCCGGAUGCACCA |
| 201 | tRNA-Arg(UCU) | GUCCUCUUAGUUAAAUGGADAUAACGAGCCC[s2C]U[mnm5U]CU[t6A]AGGGCUAAUUGCAGGTΨCGAUUCCUGCAGGGGACACCA |
| 202 | tRNA-Arg(UCU) | GCGCCCUUAGCUCAGUUGGAUAGAGCAACGAC[s2C]U[mnm5U]CU[t6A]AGΨCGUGGGCCGCAGGTΨCGAAUCCUGCAGGGCGCGCCA |
| 203 | tRNA-Asn(GUU) | UCCUCUG[s4U]AGUUCAGDCGGDAGAACGGCGGACUQUU[t6A] Ψ CCGUAU[m7G]UCACUGGTΨCGAGUCCAGUCAGAGGAGCCA |

TABLE 1-continued

RNA molecules in particular tRNAs isolated from *Escherichia coli* (Migula) Castellani & Chalmers according to the present invention.

| SEQ ID NO. | tRNA | Sequence (5'-3') |
|---|---|---|
| 204 | tRNA-Asp(QUC) | GGAGCGG[s4U]AGUUCAGDCGGDDAGAAUACCUGCCU[gluQ]UC[m2A]CGCAGGGG[m7G]UCGCGGGTΨCGAGUCCCGΨCCGUUCCGCCA |
| 205 | tRNA-Cys(GCA) | GGCGCGU[s4U]AACAAAGCGGDDAUGUAGCGGA Ψ UGCA[ms2i6A]A Ψ CCGUCUAGUCCGGTΨCGACUCCGGAACGCGCCUCCA |
| 206 | tRNA-Gln(UUG) | UGGGGUA[s4U]CGCCAAGC[Gm]GDAAGGCACCGGU[Um]U[cmnm5s2U]UG[m2A]ΨACCGGCAUUCCCUGGTΨCGAAUCCAGGUACCCCAGCCA |
| 207 | tRNA-Gln(CUG) | UGGGGUA[s4U]CGCCAAGC[Gm]GDAAGGCACCGGA[Um]UCUG[m2A] ψ ψ CCGGCAUUCCGAGGTUψCGAAUCCUCGUACCCCAGCCA |
| 208 | tRNA-Glu(UUC) | GUCCCCUUCGUCψAGAGGCCCAGGACACCGCCCU[mnm5s2U]UC[m2A]CGGCGGUAACAGGGGTψCGAAUCCCUGGGGGACGCCA |
| 209 | tRNA-Glu(UUC) | GUCCCCUUCGUCψAGAGGCCCAGGACACCGCCCU[mnm5s2U]UC[m2A]CGGCGGUAACAGGGGTψCGAAUCCCUAGGGGACGCCA |
| 210 | tRNA-Glu(UUC) | GUCCCCUUCGUCψAGAGGCCAGGACACCGCCCU[mnm5s2U]UC[m2A]CGGCGGUAACAGGGGTψCGAAUCCCCUAGGGGACGCCA |
| 211 | tRNA-Gly(CCC) | GCGGGCG[s4U]AGUUCAAUGGDAGAACGAGAGCUUCCCAAGCUCUAUACGAGGGTψCGAUUCCCUUCGCCCGCUCCA |
| 212 | tRNA-Gly(UCC} | GCGGGCAUCGUAUAAUGGCUAUUACCUCAGCCU[mnm5U]CCAAGCUGAUGAUGCGGGTψCGAUUCCCGCUGCCCGCUCCA |
| 213 | tRNA-Gly(GCC) | GCGGGAAUAGCUCAGDDGGDAGAGCACGACCUUGCCAAGGUCGGG[m7G]UCGCGAGTψCGAGUCUCGUUUCCCGCUCCA |
| 214 | tRNA-His(GUG) | GGUGGCUA[s4U]AGCUCAGDDGGDAGAGCCCUGGAUUQUG[m2A] ψ ψ CCAGUU[m7G]UCGUGGGTψCGAAUCCCAUUAGCCACCCCA |
| 215 | tRNA-Ile(GAU) | AGGCUUGUAGCUCAGGDGGDDAGAGCGCACCCCUGAU[t6A]AGGGUGAG[m7G][acp3U]CGGUGGTψCAAGUCCACψCAGGCCUACCA |
| 216 | tRNA-Ile(GAU) | AGGCUUGUAGCUCAGGUGGDDAGAGCGCACCCCUGAU[t6A]AGGGUGAG[m7G][acp3U]CGGUGGTψCAAGUCCACψCAGGCCUACCA |
| 217 | tRNA-Ile(CAU) | GGCCCCU[s4U]AGCUCAGU[Gm]GDDAGAGCAGGCGACU[k2C]AU[t6A]A ψ CGCUUG[m7G][acp3U]CGCUGGTψCAAGUCCAGCAGGGGCCACCA |
| 218 | tRNA-Leu(CAG) | GCGAAGGUGGCGGAADD[Gm]GDAGACGCGCUAGCUUCAG[m1G] ψ G ψ UAGUGUCCUUACGGACGUGGGGGTψCAAGUCCCCCCCCUCGCACCA |
| 219 | tRNA-Leu(GAG) | GCCGAGGUGGUGGAADD[Gm]GDAGACACGCUACCUUGAG[m1G] ψ GGUAGUGCCCAAUAGGGCUUACGGGTψCAAGUCCCGUCCUCGGUACCA |
| 220 | tRNA-Leu(AAA) | GCCCGGA[s4U]GGUGGAADC[Gm]GDAGACACAAGGGA ψ U[cmnm5Um]AA[ms2i6A]A ψ CCCUCGGCGUUCGCGCUGUGCGGGT ψ CAAGUCCCGCUCCGGGUACCA |
| 221 | tRNA-Leu(CAA) | GCCGAAG[s4U]GGCGAAADC[Gm]GDAGACGCAGUUGA ψ U[Cm]AA[ms2i6A]A ψ CAACCGUAGAAAUACGUGCCGGTψCGAGUCCGGCCUUCGGCACCA |
| 222 | tRNA-Lys(UUU) | GGGUCGUUAGCUCAGDDGGDAGAGCAGUUGACU[mnm5s2U]UU[t6A]A ψ CAAUUG[m7G][acp3U]CGCAGGTψCGAAUCCUGCACGACCCACCA |
| 223 | tRNA-Met(CAU) | GGCUACG[s4U]AGCUCAGDD[Gm]GDDAGAGCACAUCACU[ac4C]AU[t6A]A ψ GAUGGG[m7G][acp3U]CACAGGTψCGAAUCCCGUCGUAGCCACCA |
| 224 | tRNA-Phe(GAA) | GCCCGGA[s4U]AGCUCAGDCGGDAGAGCAGGGGA ψ UGAA[ms2i6A]A Ψ CCCCGU[m7G][acp3U]CCUUGGTψCGAUUCCGAGUCCGGGCACCA |
| 225 | tRNA-Pro(CGG) | CGGUGAUUGGCGCAGCCUGGDAGCGCACUUCGUUCGG[m1G]ACGAAGGG[m7G]UCGGAGGTΨCGAAUCCUCUAUCACCGACCA |
| 226 | tRNA-Sec(UCA) | AAGAUCG[s4U]CGUCUCCGGDGAGGCGGCUGGACUUCA[i6A]AUCCAGUUGGGGCCGCGCGGUCCCGGGCAGGTΨCGACUCCUGUGAUCUUGCCA |
| 227 | tRNA-Ser(UGA) | GGAAGUG[s4U]GGCCGAGC[Gm]GDDGAAGGCACCGGU[Cm]U[cmo5U]GA[ms2i6A]AACCGGCGACCCGAAAGGGUUCCAGAGTΨCGAAUCUCUGCGCUUCCGCCA |

TABLE 1-continued

RNA molecules in particular tRNAs isolated from *Escherichia coli* (Migula) Castellani & Chalmers according to the present invention.

| SEQ ID NO. | tRNA | Sequence (5'-3') |
|---|---|---|
| 228 | tRNA-Ser(CGA) | GGAGAGAUGCCGGAGC[Gm]GCDGAACGGACCGGUCUCGA[ms2i6A]AACCGGA GUAGGGGCAACUCUACCGGGGGTΨCAAAUCCCCCUCUCUCCGCCA |
| 229 | tRNA-Ser(GCU) | GGUGAGG[s4U]GGCCGAGAGGCGAAGGCGCUCCC[s2C]UGCU[t6A]AGGGAGU AUGCGGUCAAAAGCUGCAUCCGGGGTΨCGAAUCCCCGCCUCACCGCCA |
| 230 | tRNA-Ser(GGA) | GGUGAGG[s4U]GUCCGAGU[Gm]GDDGAAGGAGCACGCCUGGAAAG Ψ GUGUAUACGGCAACGUAUCGGGGGTΨCGAAUCCCCCCUCACCGCCA |
| 231 | tRNA-Ser(GGA) | GGUGAGGUGUCCGAGU#GCDGAAGGAGCACGCCUGGAAAGΨGUGUAUACGGC AACGUAUCGGGGTΨCGAAUCCCCCCUCACCGCCA |
| 232 | tRNA-Thr(GGU) | GCUGAUAUGGCUCAGDDGGDAGAGCGCACCCUUGGU[m6t6A]AGGGUGAG[m7G] UCCCCAGTΨCGACUCUGGGUAUCAGCACCA |
| 233 | tRNA-Thr(GGU) | GCUGAUAUAGCUCAGDDGGDAGAGCGCACCCUUGGU[m6t6A]AGGGUGAG[m7G] UCGGCAGTΨCGAAUCUGCCUAUCAGCACCA |
| 234 | tRNA-Trp(CCA) | AGGGGCG[s4U]AGUUCAADDGGDAGAGCACCGGU[Cm]UCCA[ms2i6A]AACCGG GU[m7G]UUGGGAGTΨCGAGUCUCUCCGCCCCUGCCA |
| 235 | tRNA-Tyr(QUA) | GGUGGGG[s4U][s4U]CCCGAGC[Gm]GCCAAAGGGAGCAGACUQUA[ms2i6A]A Ψ CUGCCGUCAUCGACUUCGAAGGTΨCGAAUCCUUCCCCCACCACCA |
| 236 | tRNA-Tyr(QUA) | GGUGGGG[s4U][s4U]CCCGAGC[Gm]GCCAAAGGGAGCAGACUQUA[ms2i6A]A Ψ CUGCCGUCACAGACUUCGAAGGTΨCGAAUCCUUCCCCCACCACCA |
| 237 | tRNA-Val(UAC) | GGGUGAU[s4U]AGCUCAGCGGGAGAGCACCUCCCU[cmo5U]AC[m6A]AGGAGG GG[m7G]UCGGCGGTΨCGAUCCCGUCAUCACCCACCA |
| 238 | tRNA-Val(GAC) | GCGUCCG[s4U]AGCUCAGDDGGDDAGAGCACCACCUUGACAUGGUGGGG[m7G] [acp3U]CGGUGGTΨCGAGUCCACUCGGACGCACCA |
| 239 | RNA-Val(GAC) | GCGUUCA[s4U]AGCUCAGDDGGDDAGAGCACCACCUUGACAUGGUGGGG[m7G] [acp3U]CGUUGGTΨCGAGUCCAAUUGAACGCACCA |
| 240 | tRNA-Ini(CAU) | CGCGGGG[s4U]GGAGCAGCCUGGDAGCUCGUCGGG[Cm]UCAUAACCCGAAG[m7G] UCGUCGGTΨCAAAUCCGGCCCCCGCAACCA |
| 241 | tRNA-Ini(CAU) | CGCGGGG[s4U]GGAGCAGCCUGGDAGCUCGUCGGG[Cm]UCAUAACCCGAAGAU CGUCGGTΨCAAAUCCGGCCCCCGCAACCA |

TABLE 2

Abbreviations of chemical modifications symbols of tRNA sequences

| Symbols | Common name |
|---|---|
| m1A | 1-methyladenosine |
| m2A | 2-methyladenosine |
| m6A | N6 methyladenosine |
| Am | 2'-O-methyladenosine |
| i6A | N6-isopentenyl adenosine |
| ms2i6A | 2-methylthio-N6-isopentenyl adenosine |
| t6A | N6 threonide carbamoyl adenosine |
| m6t6A | N6-methyl-N6-threosylcarbamoyl adenosine |
| I | Inosine |
| m5C | 5-methylcytidine |
| Cm | 2'-O-methylcytidine |
| s2C | 2-thiocytidine |
| ac4C | N4 acetylcytidine |
| f5C | 5-formylcytidine |
| k2C | Lysidine |
| m1G | 1-methylguanosine |
| m2G | N2 methylguanosine |
| m7G | 7-methylguanosine |
| Gm | 2'-O-methylguanosine |
| m22G | N2, N2 dimethylguanosine |
| Q | Queuosine |
| galQ | Galactosyl queuosine |
| Ψ | Pseudouridine |

TABLE 2-continued

Abbreviations of chemical modifications symbols of tRNA sequences

| Symbols | Common name |
|---|---|
| D | Dihydrouridine |
| T | 5-methyluridine |
| Um | 2'-O-methyluridine |
| s2U | 2-thiouridine |
| s4U | 4-thiouridine |
| acp3U | 3-(3-amino-3-carboxypropyl) uridine |
| mo5U | 5-methoxyuridine |
| cmo5U | Uridine 5-oxoacetic acid |
| mcmo5U | Uridine 5-oxoacetate methyl ester |
| mcm5U | 5-methoxycarbonylmethyl uridine |
| mcm5Um | 5-methoxycarbonylmethyl-2'-O-methyluridine |
| mcm5s2U | 5-methoxycarbonylmethyl-2-thiouridine |
| nm5s2U | 5-aminomethyl-2-thiouridine |
| mnm5U | 5-methylaminomethyl uridine |
| mnm5s2U | 5-methylaminomethyl-2-thiouridine |
| ncm5U | 5-aminoformylmethyluridine |
| ncm5Um | 5-carbamoylmethyl-2'-O-methyluridine |
| cmnm5U | 5-carboxymethyl aminomethyl uridine |
| cmnm5Um | 5-carboxymethylaminomethyl-2'-O-methyluridine |
| cmnm5s2U | 5-carboxymethylaminomethyl-2-methyluridine |
| tm5U | 5-taurine methyluridine |
| tm5s2U | 5-tauromethyl-2-thiouridine |

The antisense sequences of SEQ ID NO: 7 to SEQ ID NO: 100 and the sense sequences of SEQ ID NO: 101 to SEQ ID NO: 194 as shown in Table 3 are artificially synthesized in accordance with the present invention. In particular, these sequences are derived sequence fragments prepared according to the sequences in Table 1 isolated from *Escherichia coli* (Migula) Castellani & Chalmers. Said derived sequence fragments are classified into 2 groups, namely a 5'-tRFs, and a 3'-tRFs. The 5'-t group RNA molecules contain a 2-35 nucleotides cleaved at 5' terminal portion, D loop, D stem loop, anticodon loop or anticodon stem loop of the corresponding full-length tRNA molecules isolated from the bacteria; and the 3'-t group RNA molecules contain a 2-35 nucleotides cleaved at 3'-CCA terminal portion, T loop, T stem loop, anticodon loop, anticodon stem loop of the corresponding full-length tRNA molecules isolated from the bacteria. In another embodiment, tRF obtained from tRNA-Cys(GCA) comprises 22 nucleotides long 5'-tRFs "GGCGCGUUAACAAAGCGGUUAU", which corresponds to SEQ ID No: 7 and 22 nucleotides long 5'-tRFs "UCGACUCCGGAACGCGCCUCCA", which corresponds to SEQ ID No: 8.

Each of the sense sequences together with the corresponding antisense sequence form a double-stranded RNA molecule. As shown in Table 3, the sense sequence of SEQ ID NO: 101 and the antisense sequence of SEQ ID NO: 7 form a double-stranded RNA molecule with a length of 22 base pairs, and the resultant RNA molecule is denoted as EC for easy reference.

The double-stranded RNA molecules are classified into 2 groups, namely a 5'-terminal group (5'-t), and a 3'-terminal group (3'-t). The 5'-t group RNA molecules contain a 5' terminal portion of the corresponding full-length RNA molecules isolated from the bacteria; and the 3'-t group RNA molecules contain a 3' terminal portion of the corresponding full-length RNA molecules isolated from the bacteria. In another embodiment, RNA molecules may contain the anticodon loop portion of the corresponding full-length RNA molecules isolated from the gut microorganisms and referred as anticodon group RNA molecules. The antisense sequences of SEQ ID NO: 7 to SEQ ID NO: 100 can be generated by cleavage at different sites on the full-length RNA molecules SEQ ID NO: 195 to 241.

Further, the RNA molecule of the present invention may comprise a 3' overhang, preferably comprise 2 mer 3' overhangs. The provision of the 3' overhang improves the stability of the RNA molecules.

TABLE 3

RNA molecules derived from the sequences in Table 1 through artificial synthesis according to the present invention.

| Source | Code (mimic) | SEQ ID NO. | Antisense sequence (5'-3') | SEQ ID NO. | Sense sequence (5'-3') | Group |
|---|---|---|---|---|---|---|
| tRNA-Cys(GCA) | EC1 | 7 | GGCGCGUUAACAAAGCGGUUAU | 101 | AUAACCGCUUUGUUAACGCGCC | 5'-t |
| | EC2 | 8 | UCGACUCCGGAACGCGCCUCCA | 102 | UGGAGGCGCGUUCCGGAGUCGA | 3'-t |
| tRNA-His(GUG) | EC3 | 9 | GGUGGCUAUAGCUCAGUUGGUA | 103 | UACCAACUGAGCUAUAGCCACC | 5'-t |
| | EC4 | 10 | UCGAAUCCCAUUAGCCACCCCA | 104 | UGGGGUGGCUAAUGGGAUUCGA | 3'-t |
| tRNA-Lys(UUU) | EC5 | 11 | GGGUCGUUAGCUCAGUUGGUAG | 105 | CUACCAACUGAGCUAACGACCC | 5'-t |
| | EC6 | 12 | UCGAAUCCUGCACGACCCACCA | 106 | UGGUGGGUCGUGCAGGAUUCGA | 3'-t |
| tRNA-Met(CAU) | EC7 | 13 | GGCUACGUAGCUCAGUUGGUUA | 107 | UAACCAACUGAGCUACGUAGCC | 5'-t |
| | EC8 | 14 | UCGAAUCCCGUCGUAGCCACCA | 108 | UGGUGGCUACGACGGGAUUCGA | 3'-t |
| tRNA-Asn(GUU) | EC9 | 15 | UCCUCUGUAGUUCAGUCGGUAG | 109 | CUACCGACUGAACUACAGAGGA | 5'-t |
| | EC10 | 16 | UCGAGUCCAGUCAGAGGAGCCA | 110 | UGGCUCCUCUGACUGGACUCGA | 3'-t |
| tRNA-Phe(GAA) | EC11 | 17 | GCCCGGAUAGCUCAGUCGGUAG | 111 | CUACCGACUGAGCUAUCCGGGC | 5'-t |
| | EC12 | 18 | UCGAUUCCGAGUCCGGGCACCA | 112 | UGGUGCCCGGACUCGGAAUCGA | 3'-t |
| tRNA-Trp(CCA) | EC13 | 19 | AGGGGCGUAGUUCAAUUGGUAG | 113 | CUACCAAUUGAACUACGCCCCU | 5'-t |
| | EC14 | 20 | UCGAGUCUCUCCGCCCUGCCA | 114 | UGGCAGGGGCGGAGAGACUCGA | 3'-t |
| tRNA-Asp(QUC) | EC15 | 21 | GGAGCGGUAGUUCAGUCGGUUA | 115 | UAACCGACUGAACUACCGCUCC | 5'-t |
| | EC16 | 22 | UCGAGUCCCGUCCGUUCCGCCA | 116 | UGGCGGAACGGACGGGACUCGA | 3'-t |
| RNA-Pro(CGG) | EC17 | 23 | CGGUGAUUGGCGCAGCCUGGUA | 117 | UACCAGGCUGCGCCAAUCACCG | 5'-t |
| | EC18 | 24 | UCGAAUCCUCUAUCACCGACCA | 118 | UGGUCGGUGAUAGAGGAUUCGA | 3'-t |

TABLE 3-continued

RNA molecules derived from the sequences in Table 1 through artificial synthesis according to the present invention.

| Source | Code (mimic) | SEQ ID NO. | Antisense sequence (5'-3') | SEQ ID NO. | Sense sequence (5'-3') | Group |
|---|---|---|---|---|---|---|
| tRNA-Sec(UCA) | EC19 | 25 | AAGAUCGUCGUCUCC GGUGAGG | 119 | CCUCACCGGAGACGA CGAUCUU | 5'-t |
|  | EC20 | 26 | UUCGACUCCUGUGAU CUUGCCA | 120 | UGGCAAGAUCACAG GAGUCGAA | 3'-t |
| tRNA-Ala(GGC) | EC21 | 27 | GGGGCUAUAGCUCAG CUGGGAG | 121 | CUCCCAGCUGAGCUA UAGCCCC | 5'-t |
|  | EC22 | 28 | UCGAUCCCGCUUAGCU CCACCA | 122 | UGGUGGAGCUAAGC GGGAUCGA | 3'-t |
| tRNA-Ala(UGC) | EC23 | 29 | GGGGGCAUAGCUCAG CUGGGAG | 123 | CUCCCAGCUGAGCUA UGCCCCC | 5'-t |
|  | EC24 | 30 | UCGAUCCCGCGCGCUC CCACCA | 124 | UGGUGGGAGCGCGC GGGAUCGA | 3'-t |
| tRNA-Ala(UGC) | EC25 | 31 | GGGCUAUAGCUCAG CUGGGAG | 125 | CUCCCAGCUGAGCUA UAGCCCC | 5'-t |
|  | EC26 | 32 | UCGAUCCCGCAUAGCU CCACCA | 126 | UGGUGGAGCUAUGC GGGAUCGA | 3'-t |
| tRNA-Ser(CGA) | EC27 | 33 | GGAGAGAUGCCGGAG CGGCUGA | 127 | UCAGCCGCUCCGGCA UCUCUCC | 5'-t |
|  | EC28 | 34 | UCAAAUCCCCCUCUCU CCGCCA | 128 | UGGCGGAGAGAGGG GGAUUUGA | 3'-t |
| tRNA-Ser(GCU) | EC29 | 35 | GGUGAGGUGGCCGAG AGGCUGA | 129 | UCAGCCUCUCGGCCA CCUCACC | 5'-t |
|  | EC30 | 36 | UCGAAUCCCCGCCUCA CCGCCA | 130 | UGGCGGUGAGGCGG GGAUUCGA | 3'-t |
| tRNA-Ser(GGA) | EC31 | 37 | GGUGAGGUGUCCGAG UGGCUGA | 131 | UCAGCCACUCGGACA CCUCACC | 5'-t |
|  | EC32 | 38 | UCGAAUCCCCCCCUCA CCGCCA | 132 | UGGCGGUGAGGGGG GGAUUCGA | 3'-t |
| tRNA-Ser(GGA) | EC33 | 39 | GGUGAGGUGUCCGAG UGGUUGA | 133 | UCAACCACUCGGACA CCUCACC | 5'-t |
|  | EC34 | 40 | UCGAAUCCCCCCCUCA CCGCCA | 134 | UGGCGGUGAGGGGG GGAUUCGA | 3'-t |
| tRNA-Ser(UGA) | EC35 | 41 | GGAAGUGUGGCCGAG CGGUUGA | 135 | UCAACCGCUCGGCCA CACUUCC | 5'-t |
|  | EC36 | 42 | UCGAAUCUCUGCGCU UCCGCCA | 136 | UGGCGGAAGCGCAG AGAUUCGA | 3'-t |
| tRNA-Val(GAC) | EC37 | 43 | GCGUCCGUAGCUCAG UUGGUUA | 137 | UAACCAACUGAGCUA CGGACGC | 5'-t |
|  | EC38 | 44 | UCGAGUCCACUCGGAC GCACCA | 138 | UGGUGCGUCCGAGU GGACUCGA | 3'-t |
| tRNA-Val(GAC) | EC39 | 45 | GCGUUCAUAGCUCAG UUGGUUA | 139 | UAACCAACUGAGCUA UGAACGC | 5'-t |
|  | EC40 | 46 | UCGAGUCCAAUUGAA CGCACCA | 140 | UGGUGCGUUCAAUU GGACUCGA | 3'-t |
| tRNA-Val(UAC) | EC41 | 47 | GGGUGAUUAGCUCAG CUGGGAG | 141 | CUCCCAGCUGAGCUA AUCACCC | 5'-t |
|  | EC42 | 48 | UCGAUCCCGUCAUCAC CCACCA | 142 | UGGUGGGUGAUGAC GGGAUCGA | 3'-t |
| tRNA-Arg(CCG) | EC43 | 49 | GCGCCCGUAGCUCAGC UGGAUA | 143 | UAUCCAGCUGAGCUA CGGGCGC | 5'-t |
|  | EC44 | 50 | UCGAAUCCUGUCGGG CGCGCCA | 144 | UGGCGCGCCCGACAG GAUUCGA | 3'-t |
| tRNA-Arg(ICG) | EC45 | 51 | GCAUCCGUAGCUCAGC UGGUAG | 145 | CUACCAGCUGAGCUA CGGAUGC | 5'-t |
|  | EC46 | 52 | UCGAAUCCUCCCGGAU GCACCA | 146 | UGGUGCAUCCGGGA GGAUUCGA | 3'-t |
| tRNA-Arg(CCG) | EC47 | 53 | GCAUCCGUAGCUCAGC UGGAUA | 147 | UAUCCAGCUGAGCUA CGGAUGC | 5'-t |

TABLE 3-continued

RNA molecules derived from the sequences in Table 1 through artificial synthesis according to the present invention.

| Source | Code (mimic) | SEQ ID NO. | Antisense sequence (5'-3') | SEQ ID NO. | Sense sequence (5'-3') | Group |
|---|---|---|---|---|---|---|
| | EC48 | 54 | UCGAAUCCUCCCGGAUGCACCA | 148 | UGGUGCAUCCGGGAGGAUUCGA | 3'-t |
| tRNA-Arg(UCU) | EC49 | 55 | GUCCUCUUAGUUAAAUGGAUAU | 149 | AUAUCCAUUUAACUAAGAGGAC | 5'-t |
| | EC50 | 56 | UCGAUUCCUGCAGGGGACACCA | 150 | UGGUGUCCCCUGCAGGAAUCGA | 3'-t |
| tRNA-Arg(UCU) | EC51 | 57 | GCGCCCUUAGCUCAGUUGGAUA | 151 | UAUCCAACUGAGCUAAGGGCGC | 5'-t |
| | EC52 | 58 | UCGAAUCCUGCAGGGCGCGCCA | 152 | UGGCGCGCCCUGCAGGAUUCGA | 3'-t |
| tRNA-Gln(CUG) | EC53 | 59 | UGGGGUAUCGCCAAGCGGUAAG | 153 | CUUACCGCUUGGCGAUACCCCA | 5'-t |
| | EC54 | 60 | UCGAAUCCUCGUACCCCAGCCA | 154 | UGGCUGGGGUACGAGGAUUCGA | 3'-t |
| tRNA-Gln(UUG) | EC55 | 61 | UGGGGUAUCGCCAAGCGGUAAG | 155 | CUUACCGCUUGGCGAUACCCCA | 5'-t |
| | EC56 | 62 | UCGAAUCCAGGUACCCCAGCCA | 156 | UGGCUGGGGUACCUGGAUUCGA | 3'-t |
| tRNA-Ile(GAU) | EC57 | 63 | AGGCUUGUAGCUCAGGUGGUUA | 157 | UAACCACCUGAGCUACAAGCCU | 5'-t |
| | EC58 | 64 | UCAAGUCCACUCAGGCCUACCA | 158 | UGGUAGGCCUGAGUGGACUUGA | 3'-t |
| tRNA-Ile(GAU) | EC59 | 65 | AGGCUUGUAGCUCAGGUGGUUA | 159 | UAACCACCUGAGCUACAAGCCU | 5'-t |
| | EC60 | 66 | UCAAGUCCACUCAGGCCUACCA | 160 | UGGUAGGCCUGAGUGGACUUGA | 3'-t |
| tRNA-Ile(UAU) | EC61 | 67 | GGCCCCUUAGCUCAGUGGUUAG | 161 | CUAACCACCUGAGCUAAGGGGCC | 5'-t |
| | EC62 | 68 | UCAAGUCCAGCAGGGGCCACCA | 162 | UGGUGGCCCCUGCUGGACUUGA | 3'-t |
| tRNA-Thr(GGU) | EC63 | 69 | GCUGAUAUAGCUCAGUUGGUAG | 163 | CUACCAACUGAGCUAUAUCAGC | 5'-t |
| | EC64 | 70 | UCGAAUCUGCCUAUCAGCACCA | 164 | UGGUGCUGAUAGGCAGAUUCGA | 3'-t |
| tRNA-Thr(GGU) | EC65 | 71 | GCUGAUAUGGCUCAGUUGGUAG | 165 | CUACCAACUGAGCCAUAUCAGC | 5'-t |
| | EC66 | 72 | UCGACUCUGGGUAUCAGCACCA | 166 | UGGUGCUGAUACCCAGAGUCGA | 3'-t |
| tRNA-Glu(UUC) | EC67 | 73 | GUCCCCUUCGUCUAGAGGCCCA | 167 | UGGGCCUCUAGACGAAGGGGAC | 5'-t |
| | EC68 | 74 | UCGAAUCCCCUGGGGGACGCCA | 168 | UGGCGUCCCCCAGGGGAUUCGA | 3'-t |
| tRNA-Glu(UUC) | EC69 | 75 | GUCCCCUUCGUCUAGAGGCCCA | 169 | UGGGCCUCUAGACGAAGGGGAC | 5'-t |
| | EC70 | 76 | UCGAAUCCCCUAGGGGACGCCA | 170 | UGGCGUCCCCUAGGGGAUUCGA | 3'-t |
| tRNA-Glu(UUC) | EC71 | 77 | GUCCCCUUCGUCUAGAGGCCAG | 171 | CUGGCCUCUAGACGAAGGGGAC | 5'-t |
| | EC72 | 78 | UCGAAUCCCCUAGGGGACGCCA | 172 | UGGCGUCCCCUAGGGGAUUCGA | 3'-t |
| tRNA-1ni(CAU) | EC73 | 79 | CGCGGGGUGGAGCAGCCUGGUA | 173 | UACCAGGCUGCUCCACCCCGCG | 5'-t |
| | EC74 | 80 | UCAAAUCCGGCCCCCGCAACCA | 174 | UGGUUGCGGGGCCGGAUUUGA | 3'-t |
| tRNA-1ni(CAU) | EC75 | 81 | CGCGGGGUGGAGCAGCCUGGUA | 175 | UACCAGGCUGCUCCACCCCGCG | 5'-t |
| | EC76 | 82 | UCAAAUCCGGCCCCCGCAACCA | 176 | UGGUUGCGGGGCCGGAUUUGA | 3'-t |

TABLE 3-continued

RNA molecules derived from the sequences in Table 1 through artificial synthesis according to the present invention.

| Source | Code (mimic) | SEQ ID NO. | Antisense sequence (5'-3') | SEQ ID NO. | Sense sequence (5'-3') | Group |
|---|---|---|---|---|---|---|
| tRNA-Gly(CCC) | EC77 | 83 | GCGGGCGUAGUUCAAUGGUAGA | 177 | UCUACCAUUGAACUACGCCCGC | 5'-t |
|  | EC78 | 84 | UCGAUUCCCUUCGCCCGCUCCA | 178 | UGGAGCGGGCGAAGGGAAUCGA | 3'-t |
| tRNA-Gly(GCC) | EC79 | 85 | GCGGGAAUAGCUCAGUUGGUAG | 179 | CUACCAACUGAGCUAUUCCCGC | 5'-t |
|  | EC80 | 86 | UCGAGUCUCGUUUCCCGCUCCA | 180 | UGGAGCGGGAAACGAGACUCGA | 3'-t |
| tRNA-Gly(UCC) | EC81 | 87 | GCGGGCAUCGUAUAAUGGCUAU | 181 | AUAGCCAUUAUACGAUGCCCGC | 5'-t |
|  | EC82 | 88 | UCGAUUCCCGCUGCCCGCUCCA | 182 | UGGAGCGGGCAGCGGGAAUCGA | 3'-t |
| tRNA-Leu(CAA) | EC83 | 89 | GCCGAAGUGGCGAAAUCGGUAG | 183 | CUACCGAUUUCGCCACUUCGGC | 5'-t |
|  | EC84 | 90 | UCGAGUCCGGCCUUCGGCACCA | 184 | UGGUGCCGAAGGCCGGACUCGA | 3'-t |
| tRNA-Leu(CAG) | EC85 | 91 | GCGAAGGUGGCGGAAUUGGUAG | 185 | CUACCAAUUCCGCCACCUUCGC | 5'-t |
|  | EC86 | 92 | UCAAGUCCCCCCCCUCGCACCA | 186 | UGGUGCGAGGGGGGGGACUUGA | 3'-t |
| tRNA-Leu(GAG) | EC87 | 93 | GCCGAGGUGGUGGAAUUGGGAG | 187 | CUCCCAAUUCCACCACCUCGGC | 5'-t |
|  | EC88 | 94 | UCAAGUCCCGUCCUCGGUACCA | 188 | UGGUACCGAGGACGGGACUUGA | 3'-t |
| tRNA-Leu(AAA) | EC89 | 95 | GCCCGGAUGGUGGAAUCGGUAG | 189 | CUACCGAUUCCACCAUCCGGGC | 5'-t |
|  | EC90 | 96 | UCAAGUCCCGCUCCGGGUACCA | 190 | UGGUACCCGGAGCGGGACUUGA | 3'-t |
| tRNA-Tyr(QUA) | EC91 | 97 | GGUGGGGUUCCCGAGCGGCCAA | 191 | UUGGCCGCUCGGGAACCCCACC | 5'-t |
|  | EC92 | 98 | UCGAAUCCUUCCCCCACCACCA | 192 | UGGUGGUGGGGAAGGAUUCGA | 3'-t |
| tRNA-Tyr(QUA) | EC93 | 99 | GGUGGGGUUCCCGAGCGGCCAA | 193 | UUGGCCGCUCGGGAACCCCACC | 5'-t |
|  | EC94 | 100 | UCGAAUCCUUCCCCCACCACCA | 194 | UGGUGGUGGGGAAGGAUUCGA | 3'-t |

The inventors unexpectedly found that the natural chemical modifications of RNA sequence derived from EC83 in Table 3 can enhance its inhibition effects on proliferation of colorectal cancer cells. The said antisense sequences of SEQ ID NO: 1 to SEQ ID NO: 3 and the sense sequences of SEQ ID NO: 4 to SEQ ID NO: 6 as shown in Table 4 are artificially synthesized in accordance with the present invention.

The inventors unexpectedly found that the RNA molecules isolated or derived from a bacteria of genus *Escherichia* in particular *Escherichia coli* (Migula) Castellani & Chalmers are effective against cancer cells, in particular they are capable of inhibiting the growth, proliferation and/or metastasis of cancer cells.

Turning back to the method of treatment, the method comprises the step of administering an effective amount of

TABLE 4

RNA molecules derived from the EC83 mimic sequences in Table 2 through artificial synthesis according to the present invention.

| Code (mimic) | SEQ ID NO. | Antisense sequence (5'-3') | SEQ ID NO. | Sense sequence (5'-3') |
|---|---|---|---|---|
| EC83 | 89 | GCCGAAGUGGCGAAAUCGGUAG | 183 | CUACCGAUUUCGCCACUUCGGC |
| EC83-M1 | 1 | GCCGAAG[s$^4$U]GGCGAAAUCGGUAG | 4 | CUACCGAUUUCGCCACUUCGGC |
| EC83-M2 | 2 | GCCGAAGUGGCGAAAUC[Gm]GUAG | 5 | CUACCGAUUUCGCCACUUCGGC |
| EC83-M3 | 3 | GCCGAAG[s$^4$U]GGCGAAAUC[Gm]GUAG | 6 | CUACCGAUUUCGCCACUUCGGC | a RNA molecule as described above to the subject suffering from a cancer. In an embodiment, the step of administering the RNA molecule to the subject comprises contacting cancer cells of the subject with the RNA molecule.

The term "cancer" describes a physiological condition in subjects in which a population of cells are characterized by unregulated malignant (cancerous) cell growth. In an embodiment, the cancer to be treated is ovarian cancer, liver cancer, breast cancer, colorectal cancer, or lung cancer. In a particular embodiment, the cancer is colorectal cancer. In an alternative embodiment, the RNA molecules of the present invention are effective in treating cancer which is resistant against currently existing drugs such as fluorouracil, i.e. can be used to treat cancer which is resistant against fluorouracil. Specifically, the RNA molecules of the present invention can be used to treat fluorouracil-resistant colorectal cancer Accordingly, the method of the present invention can be applied to treat a subject suffering from a multi-drug resistant cancer and related disorders.

The term "subject" used herein refers to a living organism and can include but is not limited to a human and an animal. The subject is preferably a mammal, preferably a human. The RNA molecules may be administered through injection to the subject, preferably a human. The term injection encompasses intravenous, intramuscular, subcutaneous and intradermal administration. In an embodiment, the RNA molecule of the present invention is administered together with suitable excipient(s) to the subject through intravenous injection. For instance, the RNA molecule may be delivered to the subject or cells via transfection, electroporation or viral-mediated delivery.

The expression "effective amount" generally denotes an amount sufficient to produce therapeutically desirable results, wherein the exact nature of the result varies depending on the specific condition which is treated. In this invention, cancer is the condition to be treated and therefore the result is usually an inhibition or suppression of the growth or proliferation of cancer cells, a reduction of cancerous cells or the amelioration of symptoms related to the cancer cells, in particular inhibition of the proliferation of the cancer cells or induction of cell death, i.e. apoptosis of the cancer cells. In an embodiment where the cancer is metastatic cancer, the result is usually an inhibition of migration of cancer cells, suppression of the invasion of cancer cells to other tissues, inhibition of formation metastasis cancer cells at a secondary site distant from the primary site, or amelioration of symptoms related to metastatic cancer.

The effective amount of the RNA molecules of the present invention may depend on the species, body weight, age and individual conditions of the subject and can be determined by standard procedures such as with cell cultures or experimental animals.

The RNA molecule of the present invention may be administered in form of a pharmaceutical composition comprising the RNA molecule and at least one pharmaceutically tolerable excipient. The pharmaceutically tolerable excipient may be one or more of a diluent, a filler, a binder, a disintegrant, a lubricant, a coloring agent, a surfactant, a gene delivery carrier and a preservative. The pharmaceutical composition can be present in solid, semisolid or liquid form, preferably in liquid form. The pharmaceutical composition may comprise further pharmaceutical effective ingredients such as therapeutic compounds which are used for treating cancer such as fluorouracil. The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

In an embodiment, the RNA molecule is provided in a pharmaceutical composition comprising a gene delivery carrier. The gene delivery carrier refers to any molecules that can act as a carrier for delivering a gene into a cell. In an embodiment where the RNA molecule is transfected into a cell, the gene delivery carrier is considered as a transfecting agent. In an embodiment where the RNA molecule is delivered through a recombinant viral vector, the gene delivery carrier is a viral vector carrying the double-stranded RNA molecule of the present invention. The gene delivery carriers include, but is not limited to, a vector such as a viral vector, a collagen such as atelocollagen, a polymer such as polyethylenimine (PEI), a polypeptide such as poly (L-lysine) and protamine, and a lipid for forming a liposome such as Lipofectamine. The gene delivery carriers may be commercially available such as Lipofectamine RNAiMAX Transfection Reagent, Lipofectamine 3000 Reagent, and Lipofectamine® 2000 Transfection Reagent from Thermo Fisher, U.S.A.; RNAi-Mate from GenePharma, China; atelocollagen from Koken Co., Ltd., Japan); and Histidine-Lysine peptide copolymer from siRNAomics, China. The gene delivery carriers may be viral vectors based on retrovirus, adeno-associated virus, adenovirus, and lentivirus. The gene delivery carriers should have a low toxicity and cannot induce significant immune response in the subject. In an embodiment, the RNA molecule is provided in a pharmaceutical composition comprising atelocollagen, wherein atelocollagen forms a complex with the RNA molecule for delivery. In another embodiment, the RNA molecule is provided in a pharmaceutical composition comprising Lipofectamine such as Lipofectamine® RNAiMAX transfection reagent for delivering the RNA molecule to the cells. In a further embodiment, the RNA molecule is inserted into a plasmid and form recombinant vector.

In an embodiment, the pharmaceutical composition may further comprise a nucleic acid stabilizer. The nucleic acid stabilizer refers to any chemicals that are capable of maintaining the stability of the RNA molecule in the composition to minimize or avoid degradation, in particular those having ability to deactivate activity of nucleases or the like degrading the RNA molecules.

Accordingly, the present invention also pertains to a pharmaceutical composition as described above, in particular comprising the RNA molecule and a pharmaceutically tolerable excipient as defined above. In an embodiment, the RNA molecule comprises at least one sequence selected from SEQ ID NO: 1 to 100 or a functional variant or homologue thereof. Preferably, the RNA molecule is isolated or derived from a bacteria of the genus *Escherichia* as described above, in particular from *Escherichia coli* (Migula) Castellani & Chalmers.

The administration step of the RNA molecule according to the method of the present invention may be performed by injecting a pharmaceutical composition containing the RNA molecule to the target site of the subject, i.e. where cancer cells exist or body tissue adjacent to cancer cells. This is advantageous in that the RNA molecule can be directly delivered to the cancer cells before any cellular degradation such as first pass metabolism.

The RNA molecules of the present invention are also suitable for inhibiting growth or proliferation of cancer cells. In another aspect of the invention, there is provided a method of inhibiting growth or proliferation of cancer cells comprising a step of contacting said cells with an effective amount of a RNA molecule as defined above. Preferably the RNA molecule is isolated or derived from a bacteria of the genus *Escherichia* or comprises a sequence selected from SEQ ID NO: 195 to SEQ ID NO: 241 or a functional variant or homologue thereof. The cancer cells are as defined above. Preferably, the cancer cells are colorectal cancer cells. The cancer cells may be resistant against currently existing cancer drugs such as but are not limited to fluorouracil.

In an embodiment, the RNA molecule has a sequence length of from about 50 to 200 nucleotides, more preferably has a length of from about 60 to about 150 nucleotides, in particular from about 70 to about 100 nucleotides. The RNA molecule is a noncoding molecule preferably a transfer RNA molecule. Preferably, the RNA molecule comprises a sequence selected from SEQ ID NO: 7 to SEQ ID NO: 100 or a functional variant or homologue thereof; or the RNA molecule comprises SEQ ID NO: 101 to SEQ ID NO: 194 or a functional variant or homologue thereof, or the RNA molecule consists of a sequence selected from SEQ ID NO: 7 to SEQ ID NO: 100 and/or SEQ ID NO: 101 to SEQ ID NO: 194 or a functional variant or homologue thereof.

In an alternative embodiment, the RNA molecule has a sequence length of from about 10 to about 30 base pairs, from about 15 to about 25 base pairs, from about 19 to about 22 base pairs, 19 base pairs or 22 base pairs. Preferably, the RNA molecule is a double-stranded RNA molecule comprising an antisense sequence selected from SEQ ID NO: 7 to SEQ ID NO: 100 or a functional variant or homologue thereof. Preferably, said double-stranded RNA molecule or a functional variant or homologue thereof comprises an antisense sequence selected from SEQ ID NO: 7 to SEQ ID NO: 100 and a complementary sense sequence selected from SEQ ID NO: 101 to SEQ ID NO: 194. Preferably, said double-stranded RNA molecule or a functional variant or homologue thereof comprises an antisense sequence as shown in SEQ ID NO: 47, 48, 89, 90, 91 or 92, and said double-stranded RNA molecule or a functional variant or homologue thereof comprises a sense sequence as shown in SEQ ID NO: 141, 142, 183, 184, 185 or 186. Preferably, said double-stranded RNA molecule or a functional variant or homologue thereof comprises an antisense sequence as shown in SEQ ID NO: 89, and said double-stranded RNA molecule or a functional variant or homologue thereof comprises a sense sequence as shown in SEQ ID NO: 183. In particular, in an embodiment, RNA molecule or a functional variant or homologue thereof is chemically modified double-stranded RNA molecules, comprising an antisense sequence selected from SEQ ID NO: 1 to SEQ ID NO: 3, and comprising a complementary sense sequence selected from SEQ ID NO: 4 to SEQ ID NO: 6. The RNA molecule may further comprise 2 mer 3' overhangs.

The step of contacting the cancer cells with the RNA molecule of the present invention may be carried out by applying a composition in particular an incubation solution comprising the RNA molecule to said cancer cells which incubation solution may further comprise suitable excipients as defined above, a buffer or a suitable growth medium. In such embodiment of the present invention, the cancer cells are taken from a subject such as an animal or human, in particular a human. The RNA molecule is provided in the composition at a concentration of at least 3 nM, at least 5 nM, from about 5 nM to about 200 nM, from about 10 nM to about 100 nM, or from about 25 nM to about 50 nM. Further, the excipients may include a gene delivery carrier such as but is not limited to a collagen based carrier or a liposome forming agent. In an embodiment, the collagen based carrier is atelocollagen and the liposome forming agent is Lipofectamine.

The present invention pertains to a double-stranded RNA molecule as described above, i.e. comprising an antisense sequence selected from SEQ ID NO: 7 to SEQ ID NO: 100 or a functional variant or homologue thereof, and a complementary sense sequence. In particular, the double-stranded RNA molecule consists of an antisense sequence selected from SEQ ID NO: 7 to SEQ ID NO: 100 or a functional variant or homologue thereof, a complementary sense sequence selected from SEQ ID NO: 101 to SEQ ID NO: 194, and optionally a 3' overhang.

Example embodiments of the double-stranded RNA molecule are presented in Table 3. The double-stranded RNA may be subject to modification and therefore may carry at least one modified nucleoside selected form inosine, 1-methyladenosine, 2-methyladenosine, $N^6$-methyladenosine, $N^6$-isopentenyladenosine, 2'-O-methyladenosine, $N^6$-acetyladenosine, 1-methylinosine, pseudouridine, dihydrouridine, or 2-methylthio-$N^6$-methyladenosine.

In addition to the above, the present invention pertains to tRNA-half cleaved from tRNA molecule in Table 1 using specific method such as S1 nuclease or other enzymes or reagents to probably cleave tRNA into tRNA-half. The tRNA-half may further being chemically modified, and therefore may carry at least one modified nucleoside selected form inosine, 1-methyladenosine, 2-methyladenosine, $N^6$-methyladenosine, $N^6$-isopentenyladenosine, 2'-O-methyladenosine, $N^6$-acetyladenosine, 1-methylinosine, pseudouridine, dihydrouridine, or 2-methylthio-$N^6$-methyladenosine.

In further aspect of the invention, there is provided a vector comprising a nucleic acid molecule, wherein the nucleic acid molecule is a RNA molecule as described above. In particular, the RNA molecule having a sequence selected from SEQ ID NO: 1 to SEQ ID NO: 6 or a functional variant or homologue thereof. In an embodiment, the vector is a recombinant vector comprising the double-stranded RNA molecule as described above. The vector may be viral-based vector derived from retrovirus, adeno-associated virus, adenovirus, or lentivirus. An ordinary skilled in the art would appreciate suitable approach to incorporate the RNA molecule of the present invention into a vector.

Still further, the present invention pertains to use of a nucleic acid molecule in the preparation of a medicament for treating cancer. The nucleic acid is a RNA molecule as described above including a functional variant or homologue thereof. It would also be appreciated that the RNA molecule of the present invention can be used as a small interfering RNA molecule to interfere the expression of certain genes in the target cancer cells, thereby to cause gene silencing, apoptosis, inhibition of cell growth and proliferation, or the like to achieve the desired therapeutic effect.

Accordingly, the present invention provides a novel and effective approach for treating cancers from various origins by administration of a RNA molecule that is isolated or derived from a bacteria of the genus *Escherichia*, or in particular a RNA molecule comprising a sequence selected from SEQ ID NO: 1 to 6. Administration of said RNA molecule is also suitable for inhibiting growth or proliferation of cancer cells. The RNA molecules are found to be highly effective at inhibiting growth and proliferation of cancer cells in vitro and exhibit an antitumor effect in vivo. Said RNA molecules are also effective against fluorouracil-resistant cell lines.

The invention is now described in the following non-limiting examples.

EXAMPLES

Chemicals and Materials

*Escherichia coli* MRE 600 total transfer ribonucleic acid was purchased from Roche (Basel, Switzerland). MicroRNA marker and low range ssRNA ladder were purchased from New England BioLabs (Massachusetts, U.S.A.). Diethylpyrocarbonate (DEPC)—treated water, S1 nuclease, RNase T1 and polyacrylamide containing a ratio of Acrylamide/Bis (19:1, w/w), tris/borate/EDTA (TBE), ammonium persulphate (APS) and tetramethylethylenediamine (TEMED), mirVana™ miRNA isolation kit, SYBR gold nucleic acid gel stain and gel loading buffer II were purchased from Thermo Fisher Scientific (U.S.A.). Guanidinium thiocyanate, triethylammonium acetate, hexafluoro-2-propanol and fluorouracil (5-FU) were purchased from Sigma (Missouri, U.S.A.). Ethanol was purchased from Anaqua Chemicals Supply Inc. Ltd. (U.S.A.). Deionized water was prepared by a Millipore Milli-Q Plus system (Millipore, U.S.A.). HCT-8 human ileocecal colorectal adenocarcinoma cell line and its 5-FU-resistant strain (HCT-8/5-FU), LoVo colorectal adenocarcinoma cell line and its 5-FU-resistant strain (LoVo/5-FU) were purchased from American Type Culture Collection (ATCC, U.S.A.). Opti-MEM medium, RPMI 1640 medium, 10% fetal bovine serum (FBS) and 1% penicillin/streptomycin (P/S) were purchased from Gibco (New Zealand). F-12K medium was purchased from Thermo (U.S.A.), MTT [3-(4,5-dimethylthiazol-2-yl)-2,5-diphenyltetrazolium bromide] was purchased from Sigma (St Louis, MO, U.S.A.).

Example 1

Figure 1B:
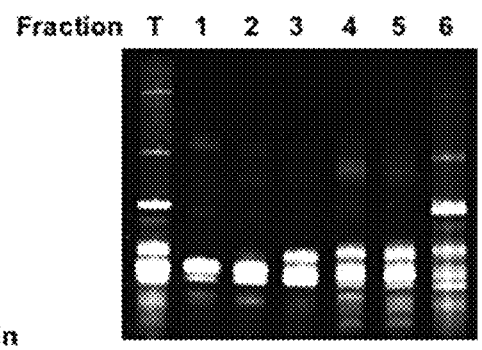
FIG. 1B shows urea denatured polyacrylamide gel electrophoresis profile of 6 mixed tRNA fractions separated by high-performance weak-anion exchange chromatographic method in accordance with an example embodiment.

Isolation of RNA molecules from mixed total tRNA of *Escherichia coli* Weighed powders of *Escherichia coli* MRE600 total tRNA were dissolved in DEPC-treated water. RNA concentration of the solutions was determined by NanoDrop (Thermo, U.S.A.). 100 μg of *Escherichia coli* total tRNA was directly injected into high-performance liquid weak-anion chromatography coupled with a diode array detector for separation of six fractions using the chromatographic conditions as follows: Column: TSKgel DNA-STAT column (4.6×100 i.d., 5 μm, Tosoh, Tokyo, Japan); The flow rate was set as 0.2 mL/min; The column was equilibrated with 20 mM Tris buffer (pH=8.5). Gradient elution with (A) 20 mM Tris buffer (pH=8.5) and (B) 20 mM Tris buffer+1 M NaCl (pH=8.5) was 0-120 min, 53%-63% B. The obtained six fractions were freeze-dried using a Speed-Vac system RVC 2-18 (Marin Christ, Germany). Powders of RNA and inorganic salts were then dissolved with DEPC-treated water and desalted by mirVana™ miRNA Isolation Kit. FIGS. 1A and 1B show that total tRNA was successfully separated into six different fractions by using this method.

Figure 2A:
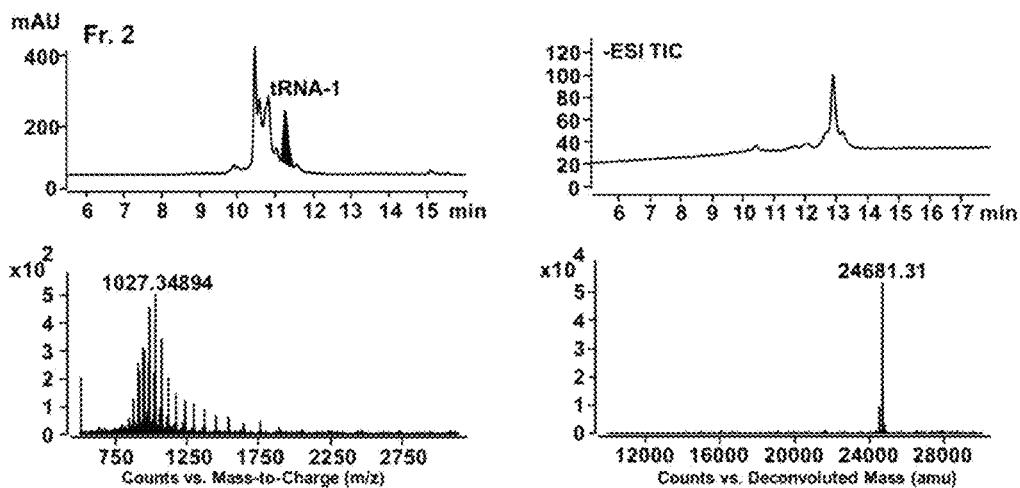
FIG. 2A shows chromatogram under UV 260 nm of fraction 2 separated by high-performance weak-anion exchange chromatographic method, total ion chromatogram of tRNA-1 analyzed by ultra-high performance liquid chromatography coupled with mass spectrometry, multiple charge distribution and deconvolution chromatogram of tRNA-1 in accordance with an example embodiment.
Figure 2B:
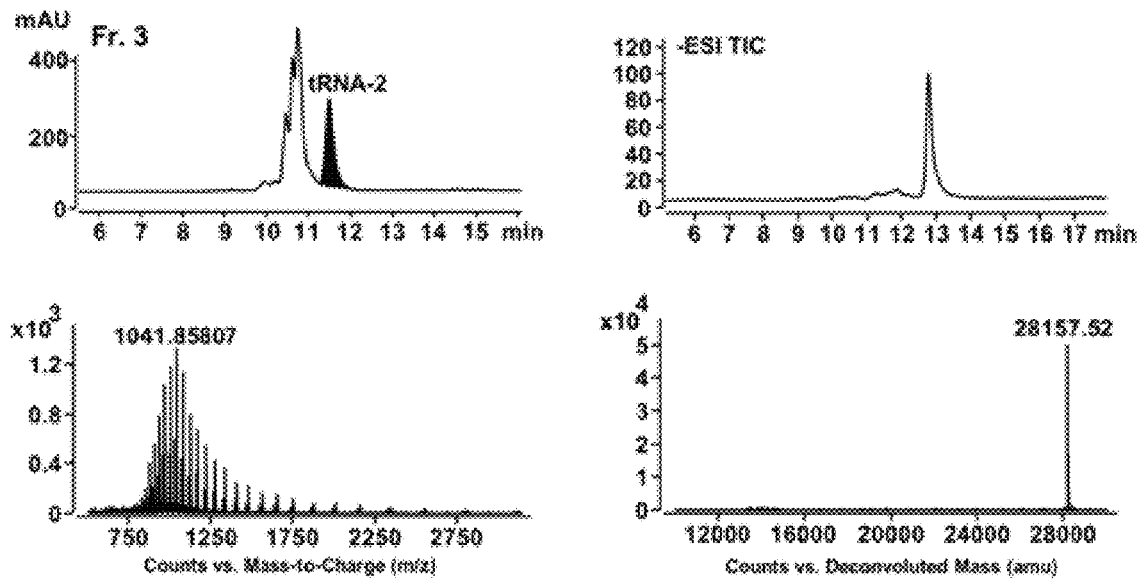
FIG. 2B shows chromatogram under UV 260 nm of fraction 3 separated by high-performance weak-anion exchange chromatographic method, total ion chromatogram of tRNA-2 analyzed by ultra-high performance liquid chromatography coupled with mass spectrometry, multiple charge distribution and deconvolution chromatogram of tRNA-2 in accordance with an example embodiment.
Figure 2C:
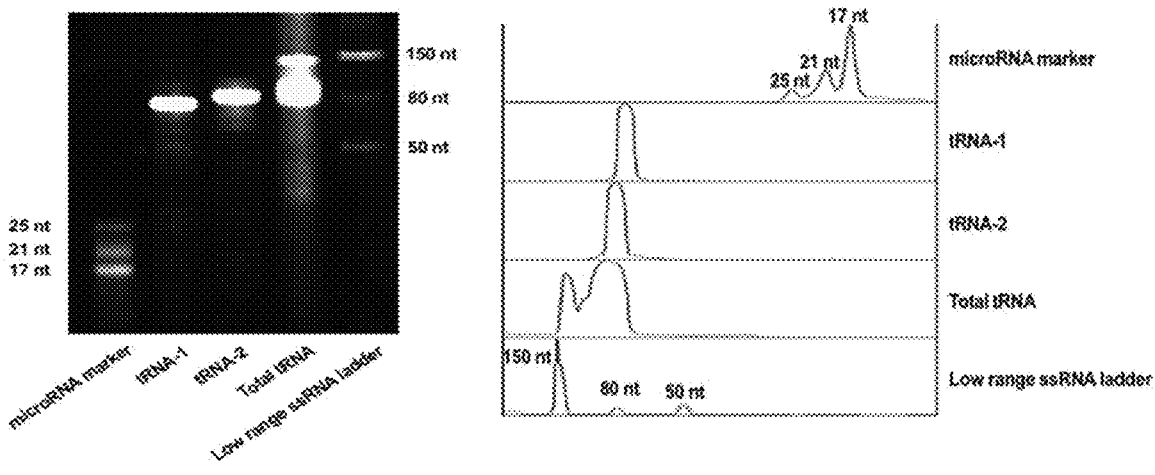
FIG. 2C shows urea denatured polyacrylamide gel electrophoresis profile of tRNA-1 and tRNA-2, including microRNA marker, total tRNA fraction and low range ssRNA ladder in accordance with an example embodiment.

Subsequently, fraction 2 and fraction 3 were separated by high-performance liquid ion-pair chromatography coupled with a diode array detector. The chromatographic conditions are as follows: Column: DNAPac RP column (3.0×100 i.d., 4 μm, Thermo); The flow rate was set as 0.2 mL/min; The column was equilibrated with 100 mM triethylammonium acetate (pH=7.0). Gradient elution with (A) 100 mM triethylammonium acetate (pH=7.0) and (B) 25% acetonitrile in A was 0-5 min, 30%-37% B; 5-25 min, 37%-45% B; 25-35 min, 45%-100% B; 35-45 min, 100% B. FIGS. 2A, 2B and 2C show that two RNA molecules with high purity were obtained from fraction 2 and fraction 3.

Example 2

Chemical Characterization of Purified RNA Molecules

Figure 3:
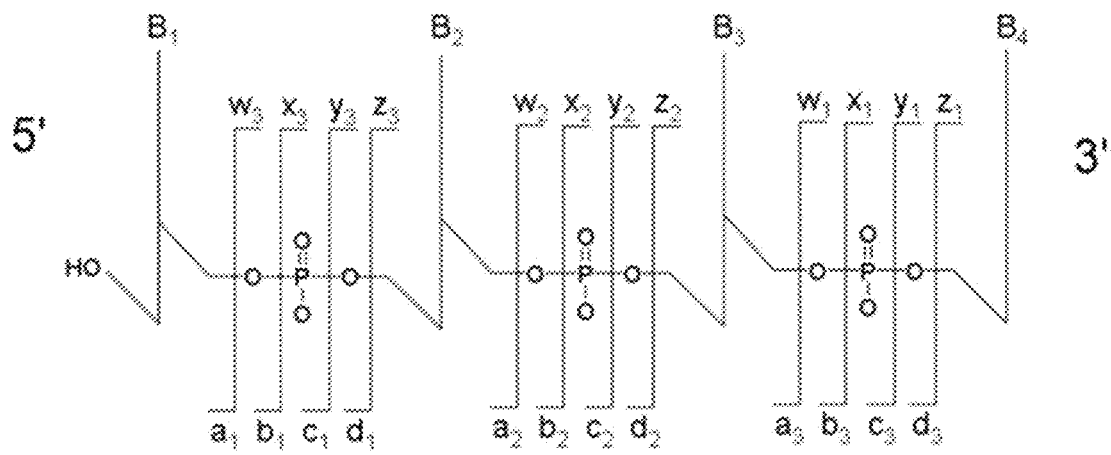
FIG. 3 shows the fragmentation rule of oligonucleotides for characterization of purified tRNA in accordance with an example embodiment.

Further, to characterize the tRNAs by mass spectrometry. The inventors employed ultra-high performance liquid chromatography coupled with quadruple time-of-flight mass technique (UHPLC-QTOF-MS) to quantitative analyze the accurate sequence information and chemical modifications of digested products of purified tRNAs. tRNA would be cleaved to several oligonucleotide fragments in length of 2-15 nt with terminal of guanine 3'-phosphoric acid. In negative mode of ESI source, oligonucleotides would have molecular ion peak with multiple charges. Charge numbers depend on the length of nucleotides, which means that nucleotide with longer length would carry more charges. The sequence information and chemical modifications are determined through collision-induced dissociation (CID) analysis of the rule and products information of tRNA-RNase T1 digestions. At the same impact voltage, the stronger the excimer ion peak intensity is, the greater the fragment response intensity is. In addition, the molecular ion peaks with more charges are easier to be cleaved, and the more fragment information is generated. Due to the complexity of CID profiles of oligonucleotide fragments longer than 8 nt, multiple excimer ions and the corresponding optimal collision energy were selected in the process of sequence analysis. CID cleavage of oligonucleotides is most easily cleaved at the phosphodiester bond and the junction between base and ribose, resulting in a series of characteristic fragments, mainly a-B, c, y and w type ions. FIG. 3 shows that the sequence of oligonucleotides can be analyzed by c, y and w type ions, and the type of nucleotide modification can be further determined by type a-B ions.

The purified RNA was freeze-dried and redissolved with RNase-treated water. Each 1 μg of purified RNA was mixed with 50 units of RNase T1 and mixed with ammonium acetate (220 mM). After incubation in water bath at 37° C. for 1.5 h, the mixed solutions were incubated at 70° C. for 10 minutes to terminate the reaction. After centrifugation at 10000×g for 1 min, the supernatant was collected for UHPLC-MS analysis.

Figure 4A:
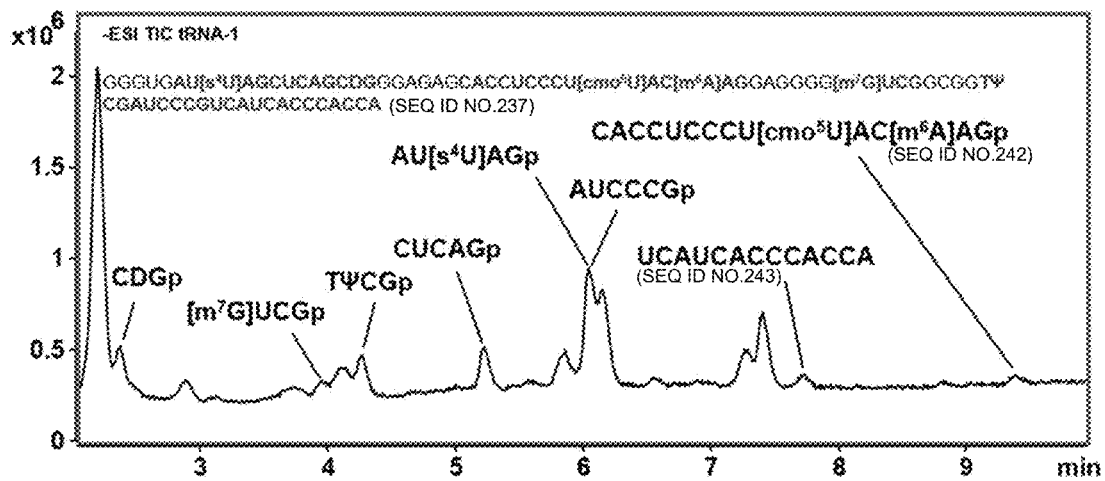
FIG. 4A shows the identification of specific fragment of tRNA-1 digested by RNase T1 in total ion chromatography in accordance with an example embodiment.
Figure 4B:
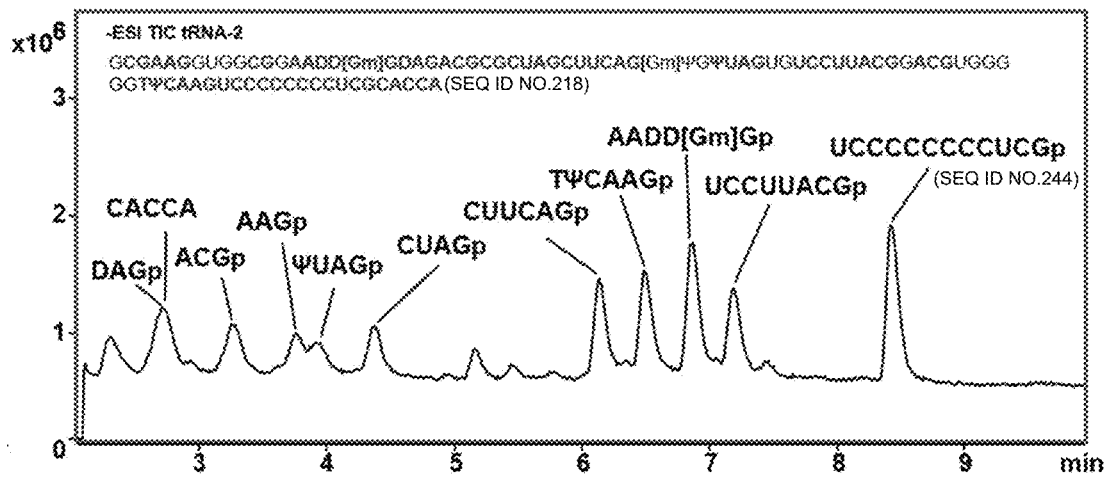
FIG. 4B shows the identification of specific fragment of tRNA-2 digested by RNase T1 in total ion chromatography in accordance with an example embodiment.

UHPLC-MS/MS was performed on an Agilent UHPLC 1290 system (Agilent Technologies, Santa Clara, CA, USA), equipped with a vacuum degasser, a quaternary pump, an autosampler, a diode array detector and an Agilent ultrahigh definition 6545 Q-TOF mass spectrometer. Separation was carried out on an ACQUITY UPLC OST $C_{18}$ Column (2.1×100 mm i.d., 1.7 μm, Waters, Massachusetts, U.S.A.) at 60° C. The flow rate was set at 0.2 mL/min and sample injection volume was 20 μL. Gradient elution with (A) 100 mM hexafluoro-2-propanol (HFIP)+15 mM trimethylamine (TEA) and (B) 50% MeOH in A was 0-1.5 min, 2% B, 1.5-8.3 min, 2%-28% B, 8.3-16.5 min, 28%-34% B, followed by washing with 80% B and equilibration with 2% B. ESI conditions were as follows: gas temperature 320° C., spray voltage 3.5 kV, sheath gas flow and temperature were set as 12 L/min and 350° C., respectively. FIGS. 4A and 4B show the MS2 results of specific RNase T1 digestion products of purified RNA molecules, the signals are in accordance with that of the specific fragments of *Escherichia coli* tRNA in database. Thus, the purified RNA molecules are characterized as tRNA-Val(UAC) (tRNA-1) and tRNA-Leu (CAG) (tRNA-2).

TABLE 5

MS/MS data of RNase T1 signature digestion products of tRNA-1 (SEQ ID NO:237) and tRNA-2 (SEQ ID NO:218).

| tRNA | Signature T1 digestion sequence | Calculated, mass[a] (Da) | Deconvoluted mass (Da) | Difference[b] (Da) | m/z | Measured mass (Da) |
|---|---|---|---|---|---|---|
| tRNA-1 | AU[s⁴U]AGp | 1649.189 | 1649.189 | 0 | $[M - 2H]^{2-}$ | 823.587 |
| | CUCAGp | 1608.216 | 1608.216 | 0 | $[M - H]^{-}$ | 1607.206 |
| | CDGp | 976.138 | 976.139 | 0.001 | $[M - H]^{-}$ | 975.132 |
| | CACCUCCCU[cmo⁵U]AC[m⁶A]AGp (SEQ ID NO:242) | 4820.644 | 4820.652 | 0.008 | $[M - 3H]^{3-}$ | 1605.876 |
| | [m⁷G]UCGp | 1333.186 | 1333.185 | −0.001 | $[M - H]^{-}$ | 1332.177 |
| | TΨPCGp | 1294.163 | 1294.164 | 0.001 | $[M - H]^{-}$ | 1293.155 |
| | AUCCCGp | 1913.257 | 1913.262 | 0.005 | $[M - 2H]^{2-}$ | 955.623 |
| | UCAUCACCCACCA (SEQ ID NO:243) | 4001.590 | 4001.593 | 0.003 | $[M - 3H]^{3-}$ | 1333.191 |
| tRNA-2 | AAGp | 1021.161 | 1021.164 | 0.003 | $[M - H]^{-}$ | 1020.156 |
| | AADD[Gm]Gp | 1996.305 | 1996.315 | 0.01 | $[M - 2H]^{2-}$ | 997.150 |
| | DAGp | 1000.150 | 1000.154 | 0.004 | $[M - H]^{-}$ | 999.146 |
| | ACGp | 997.150 | 997.154 | 0.004 | $[M - H]^{-}$ | 996.149 |
| | CUAGp | 1303.175 | 1303.182 | 0.007 | $[M - H]^{-}$ | 1302.171 |
| | CUUCAGp | 1914.241 | 1914.251 | 0.010 | $[M - 2H]^{2-}$ | 956.118 |
| | ΨUAGp | 1304.159 | 1304.161 | 0.002 | $[M - H]^{-}$ | 1303.154 |
| | UCCUUACGp | 2525.307 | 2525.320 | 0.013 | $[M - 2H]^{2-}$ | 1262.159 |
| | TΨCAAGp | 1952.268 | 1952.278 | 0.01 | $[M - 2H]^{2-}$ | 975.131 |
| | UCCCCCCCCUCGp (SEQ ID NO:244) | 3720.476 | 3720.492 | 0.016 | $[M - 3H]^{3-}$ | 1239.492 |
| | CACCA | 1511.271 | 1511.279 | 0.008 | $[M - 2H]^{2-}$ | 754.633 |

[a] theoretical monoisotopic mass
[b] Difference = (Deconvoluted mass) − (Calculated mass)

Example 3

Preparation of tRNA-Half Molecules

Figure 5A:
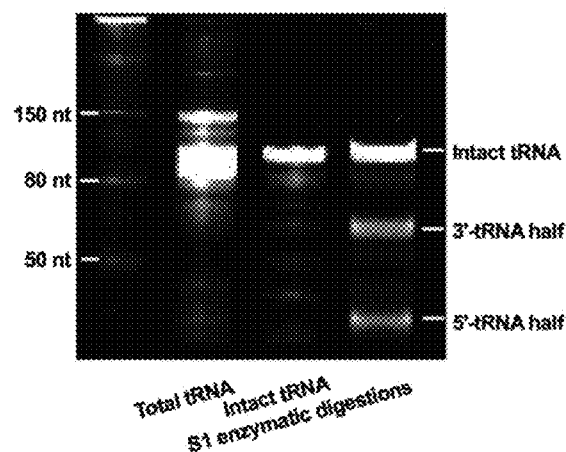
FIG. 5A shows chromatograms under UV 260 nm of fragments of tRNA-2 digested by S1 nuclease, 5'-tRNA-half molecules and 3'-tRNA-half molecules by ultra-high performance liquid chromatography in accordance with an example embodiment.
Figure 5B:
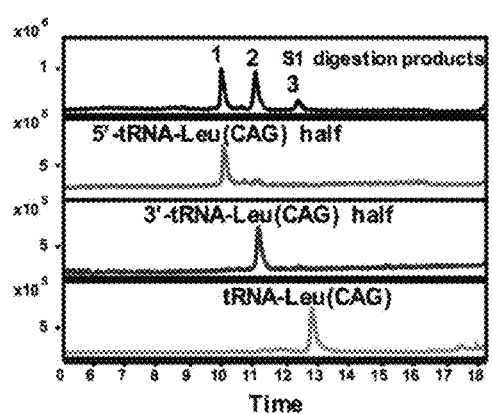
FIG. 5B shows the urea denatured polyacrylamide gel electrophoresis profile of fragments of tRNA-2 digested by S1 nuclease, including low range ssRNA ladder, total tRNA fraction and tRNA-2 in accordance with an example embodiment.

Further, the inventors employed specific S1 nuclease to prepare tRNA-half molecule. Each 500 ng of purified tRNA molecule was dissolved with DEPC-treated RNase-free water and mixed with 8 units of S1 nuclease, followed by added with 2 μL of 5× reaction buffer solutions and mixed with deionized water to 20 μL. After incubation in water bath at 25° C. for 40 min, the mixed solutions were with 0.5 μL of 0.5 M EDTA solution to terminate the reaction. After centrifugation at 10000×g for 1 min, the supernatant was collected and analyzed by urea denatured polyacrylamide gel electrophoresis. FIG. 5A shows that compared to tRNA-Leu(CAG), the digestion products clearly exhibited 2 fragments in the length of almost 30 nt long, which demonstrated the enzyme digestion succussed and the products were tRNA-Leu(CAG) half. Subsequently, the digestion products were injected to ultra-high performance liquid chromatography and separated using the chromatographic condition in EXAMPLE 2. See the prepared tRNA-half molecules in FIG. 5B, the prepared solutions were concentrated and freeze-dried, and stored at −80° C. The tRNA-Val(UAC) half was obtained using the above method.

Example 4

Synthesis of RNA Molecule

The inventors designed and synthesized RNA molecules having a length of about 22 bp based on the 147 isolated tRNA sequences in database. In particular, the tRNA sequences are considered to have at least 3 portions, namely a 5'-terminal portion (5'-t), a 3'-terminal portion (3'-t) and an anticodon portion. Each of the specifically designed RNA molecules contains any one of the portions. For instance, designed RNA molecules containing a 5' terminal portion of the corresponding full-length tRNA sequence are referred as 5'-t group RNA molecules; designed RNA molecules containing a 3' terminal portion of the corresponding full-length tRNA sequence are referred as 3'-t group RNA molecules; designed RNA molecules containing an anticodon portion of the corresponding full-length tRNA sequence are referred as anticodon group RNA molecules. The RNA molecules having a sense sequence selected from SEQ ID NO: 101 to SEQ ID NO: 194 and a complementary antisense sequence selected from SEQ ID NO: 7 to SEQ ID NO: 100, as shown in Table 3, were designed and synthesized by cleavage at different sites on the tRNA sequences in Table 1. The RNA molecules having an antisense sequence selected from SEQ ID NO: 1 to SEQ ID NO: 3 and a complementary sense sequence selected from SEQ ID NO: 4 to SEQ ID NO: 6, as shown in Table 4, were designed and synthesized by cleavage at different sites on the EC83 sequence in Table 3.

Example 5

Cytotoxic Effect of tRNA, tRNA-Half and tRF Mimic Molecules on Colorectal Cancer Cells HCT-8, fluorouracil-resistant HCT-8, fluorouracil-resistant LoVo cell lines were cultured in RPMI Medium 1640 medium containing 10% FBS and 1% penicillin/streptomycin. LoVo cell line was cultured in F-12K medium containing 10% FBS and 1% penicillin/streptomycin. All cell lines above were cultured at humidified atmosphere containing 5% $CO_2$ at 37° C.

In the cytotoxicity assay, exponentially growing cells of each cancer cell line were plated in 96-well microplate at a density of 5000 cells per well in 100 μL of culture medium and allowed to adhere for 24 h before treatment. Serial concentrations of RNA molecules obtained in Example 1 to 4 in a mixture containing a gene delivery carrier, i.e. Lipofectamine™ RNAiMAX Transfection Reagent (Thermo Fisher Scientific, U.S.A.) were then added to the cells. After treated for 48 h, MTT solution (50 µL per well, 1 mg/mL solution) was added to each well and incubated for 4 h at 37° C. Subsequently, 200 µL dimethyl sulfoxide (DMSO) were added and the optical densities of the resulting solutions were calorimetrically determined at 570 nm using a SpectraMax 190 microplate reader (Molecular Devices, Sunnyvale, CA, U.S.A). Dose-response curves were obtained, and the $IC_{50}$ values were calculated by GraphPad Prism 5 (GraphPad, La Jolla, CA, USA). Each experiment was carried out for three times. $IC_{50}$ results were expressed as means±standard deviation.

Figure 6C:
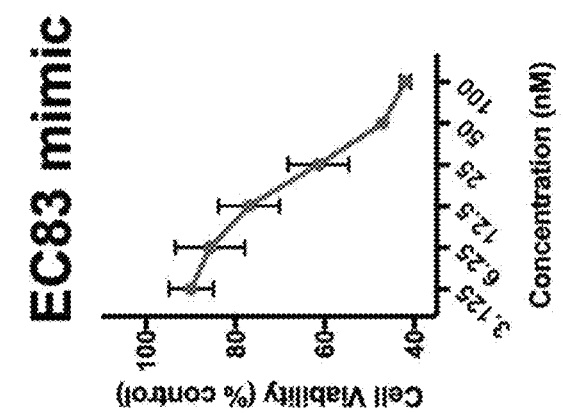
FIG. 6C is a line chart showing the cell viability of HCT-8 cells after treatment with RNA molecule EC83 mimic derived from *Escherichia coli* (Migula) Castellani & Chalmers at different concentrations, i.e. 3.125 nM, 6.25 nM, 12.5 nM, 25 nM, 50 nM and 100 nM, compared to a control group in accordance with an example embodiment (mean±SD n=3).
Figure 6B:
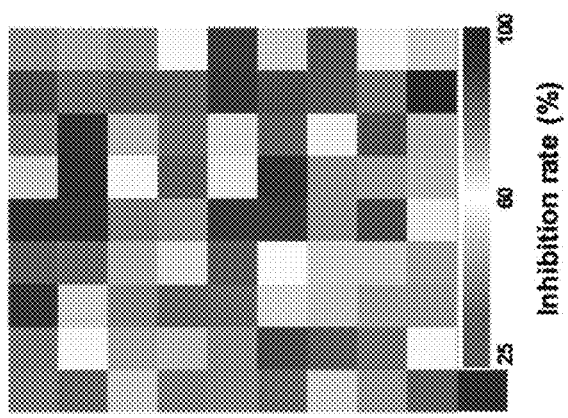
FIG. 6B is a heatmap showing the death rate of HCT-8 cell line treated by a total of 82 RNA molecules in Table 3, including EC1-EC24, EC26-EC33, EC35-EC47, EC49-EC54, EC56-EC58, EC61-EC68, EC70-EC71, EC73-EC74, EC77-EC92 derived from *Escherichia coli* (Migula) Castellani & Chalmers with a sequence length of 22 bp at a dose of 50 nM, compared to a control group and a liposome group in accordance with an example embodiment (mean±SD n=3).
Figure 6A:
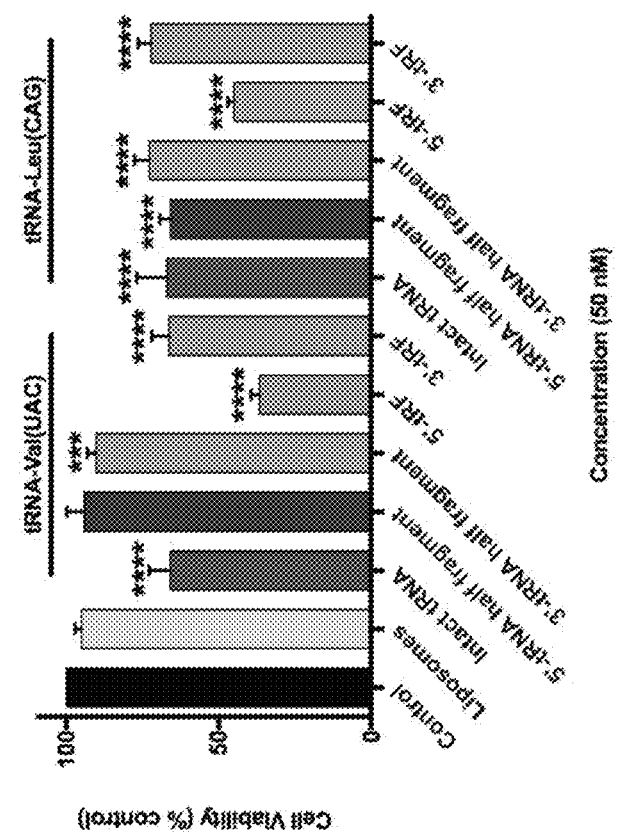
FIG. 6A is a bar chart showing the cell viability of HCT-8 cell line treated by 50 nM RNA molecules 5'-tRNA half fragments and 3'-tRNA half fragments of tRNA-Val(UAC) and tRNA-Leu(CAG), 5'-tRF mimic and 3'-tRF mimic from *Escherichia coli* (Migula) Castellani & Chalmers compared to a control group and a liposome group, in accordance with an example embodiment (mean±SD n=3; *, $p<0.001$, **, $p<0.0001$ vs. vehicle control).

With reference to Figure. 6A, HCT-8 cells were treated with 50 nM RNA molecules of tRNA-Val(UAC), tRNA-Leu(CAG), 5'-tRNA-Val(UAC) half, 3'-tRNA-Val(UAC) half, 5'-tRNA-Leu(CAG) half, 3'-tRNA-Leu(CAG) half, EC41 mimic, EC42 mimic, EC85 mimic and EC86 mimic for 48 h before addition of MTT solution. The cell viability of these cells is compared to a control group and a RNAiMAX group. A comparative example using fluorouracil was conducted. FIG. 6A shows that these RNA molecules are also effective to colorectal cancer cells.

FIG. 6B shows the cytotoxic effect of synthetic RNA molecules in Example 4 on HCT-8 cells. The results demonstrated that in this example, RNA molecules designed and synthesized based on the ensured tRNA sequences in Example 4 are also effective to inhibit cancer cells, particularly are effective in inhibition on the growth and proliferation of colorectal cancer cells. Specifically, FIG. 6C shows that EC83 mimic exhibited the strongest cytotoxicity.

Figure 7A:
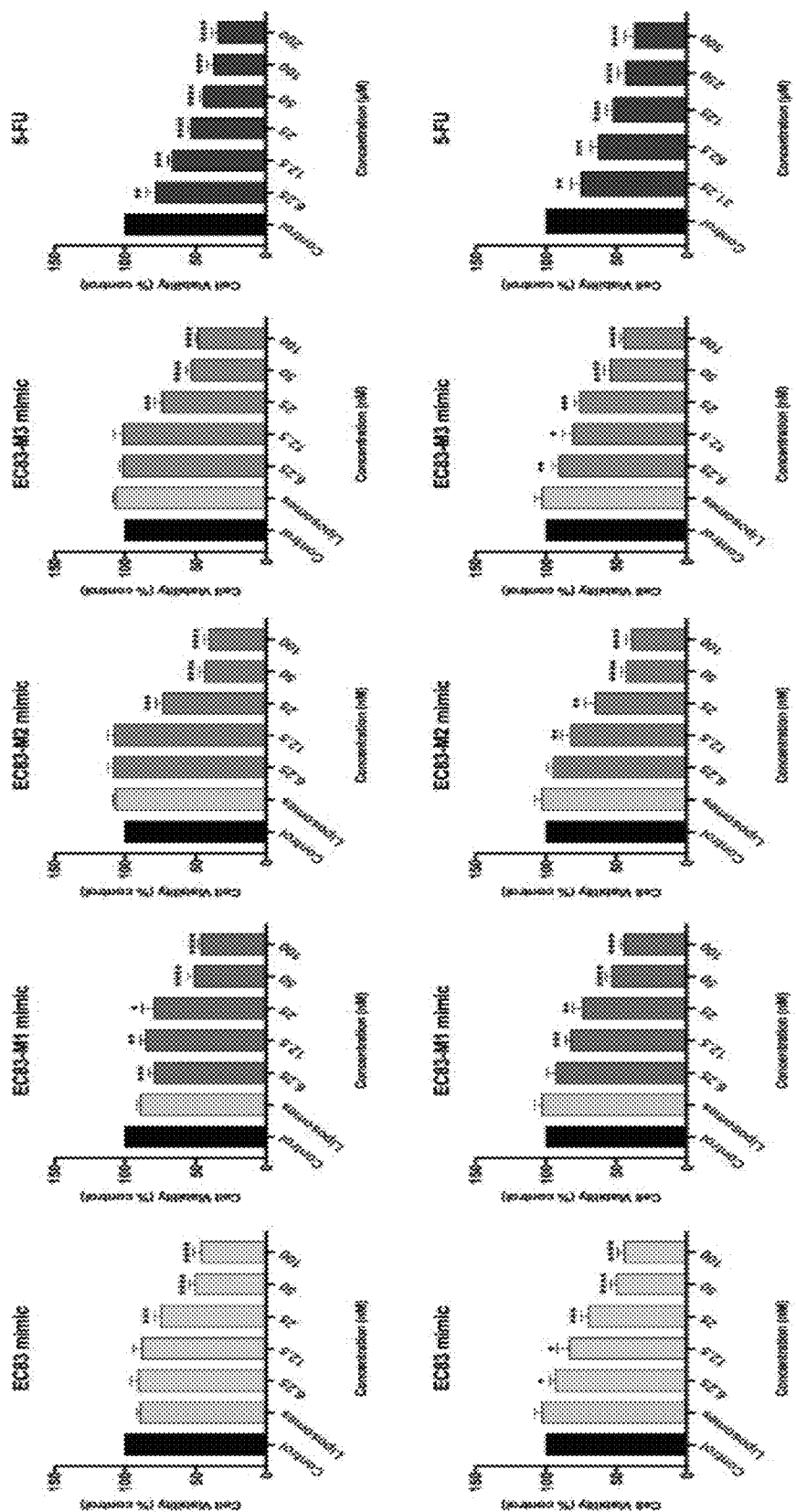
FIGS. 7A and 7B are line charts showing the cell viability of HCT-8 cells, HCT-8/5-FU cells, LoVo cells and LoVo/5-FU cells after treatment with RNA molecule EC83 mimic, EC83-M1 mimic, EC83-M2 mimic and EC83-M3 mimic derived from *Escherichia coli* (Migula) Castellani & Chalmers at different concentrations, i.e. 3.125 nM, 6.25 nM, 12.5 nM, 25 nM, 50 nM and 100 nM, compared to a control group in accordance with an example embodiment (mean±SD n=3; *, p<0.05, *, p<0.001, **, p<0.0001 vs. vehicle control).
Figure 7B:
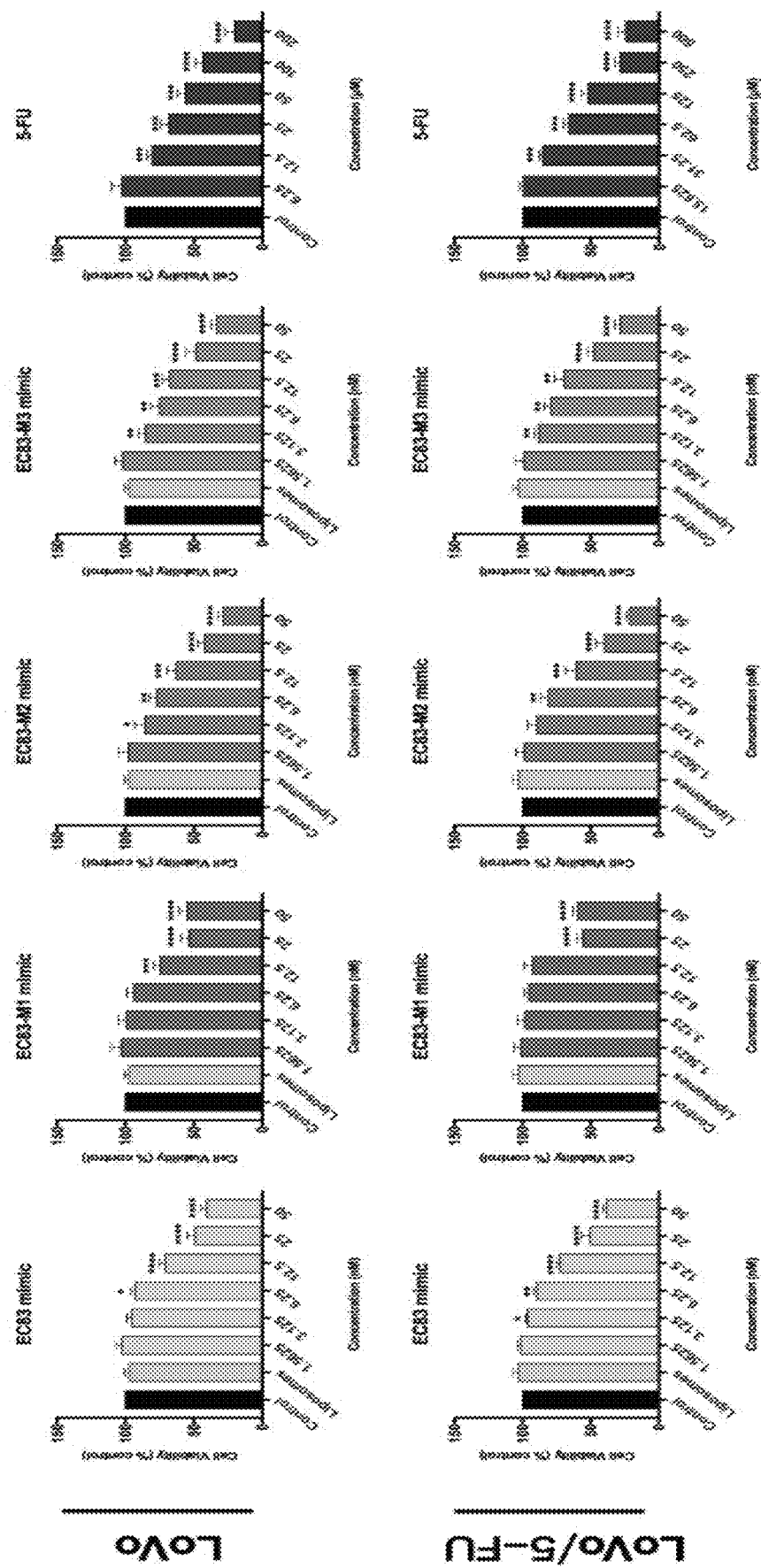

The inventors then specifically determined the cytotoxic effect and $IC_{50}$ of RNA molecule EC83 mimic and different chemically modified RNA molecules EC83-M1, EC83-M2 and EC83-M3 mimic on HCT-8 and LoVo cells, at different concentrations, i.e. 6.25 nM, 12.5 nM, 25 nM, 50 nM and 100 nM. As shown in FIGS. 7A and 7B, the results are compared to a control group and a RNAiMAX group containing a transfecting agent. The results demonstrated that RNA molecule EC83 mimic and different chemically modified EC83-M1, EC83-M2, EC83-M3 mimic have a dose-dependent effect on inhibiting the growth and proliferation of colorectal cancer cells and their fluorouracil-resistant strains. Their IC50 values were summarized in Table 6. A comparative example was conducted using fluorouracil with results.

TABLE 6

IC50 values of EC83 mimic and different chemically modified RNA molecules of EC83-M1, EC83-M2 and EC83-M3 mimic on colorectal cancer cells and their fluorouracil-resistant strains.

| Cell line | $IC_{50}$ (nM) | | | | |
|---|---|---|---|---|---|
| | EC83 mimic | EC83-M1 mimic | EC83-M2 mimic | EC83-M3 mimic | 5-FU |
| HCT-8 | 70.6 | 77.9 | 58.9 | 74.5 | 41400 |
| HCT-8/5-FU | 63.4 | 69.6 | 48.8 | 72.2 | 170600 |
| LoVo | 28.8 | 43.6 | 19.9 | 24.1 | 63900 |
| LoVo/5-FU | 29.5 | 54.2 | 18.3 | 23.0 | 133200 |

In the clonogenic assay, HCT-8 or LoVo cells were plated in 6-well microplate at a density of 1000 cells per well in 2 mL of culture medium and allowed to adhere for 24 h before treatment. Single concentration of RNA molecules obtained in Example 1 to 4 in a mixture containing a gene delivery carrier, i.e. Lipofectamine™ RNAiMAX Transfection Reagent (Thermo Fisher Scientific, U.S.A.) were then added to the cells. After treated for 48 h, discarded the drug solutions and replaced with 2 mL of fresh culture medium. After culture 14 days, discarded the culture medium and the cells were fixated with 4% paraformaldehyde fix solution for 20 min, followed by stained with crystal violet for 10 min and then washed by deionized water. The 6-well microplate was photographed and the number of colonies with more than 50 individual cells were counted using ImageJ software (U.S.A.). Each experiment was carried out for three times. Results were expressed as means±standard deviation.

With reference to FIGS. 8A and 8B, HCT-8 cells and LoVo cells were treated with 50 nM or 25 nM RNA molecules of EC83 mimic and different chemically modified RNA molecules EC83-M1, EC83-M2 and EC83-M3 mimic. The colony number of these cells is compared to a control group. A comparative example using fluorouracil was conducted. The results show that these RNA molecules can significantly inhibit the proliferation of colorectal cancer cells. Specifically, EC83-M2 mimic exhibited the strongest anti-proliferation activity.

In the wound-healing assay, HCT-8 or LoVo cells were plated in 6-well microplate at a density of 500,000 cells per well in 2 mL of culture medium and allowed to adhere for 24 h before treatment. Serial concentrations of RNA molecules obtained in Example 1 to 4 in a mixture containing a gene delivery carrier, i.e. Lipofectamine™ RNAiMAX Transfection Reagent (Thermo Fisher Scientific, U.S.A.) were then added to the cells. After treated for 48 h, discarded the drug solutions and replaced with 2 mL of fresh culture medium. After culture 14 days, discarded the culture medium and the cells were fixated with 4% paraformaldehyde fix solution for 20 min, followed by stained with crystal violet for 10 min and then washed by deionized water. The 6-well microplate was photographed and the number of colonies with more than 50 individual cells were counted using ImageJ software (U.S.A.). Each experiment was carried out for three times. Results were expressed as means±standard deviation. A 1 mL bacteria-free pipette tip was used to make a cross-scratch at the bottom of 6-well microplate. The cells in the scratch were washed away using phosphor buffer solution and the 6-well microplate was photographed under a microscope. Single concentration of RNA molecules obtained in Example 1 to 4 in a mixture containing a gene delivery carrier, i.e. Lipofectamine™ RNAiMAX Transfection Reagent (Thermo Fisher Scientific, U.S.A.) were then added to the cells. The cells were then photographed under microscope at 24 and 48 h. ImageJ software was applied to quantify the area of wound created. Each experiment was carried out for three times. Results were expressed as means±standard deviation.

Figure 9A:
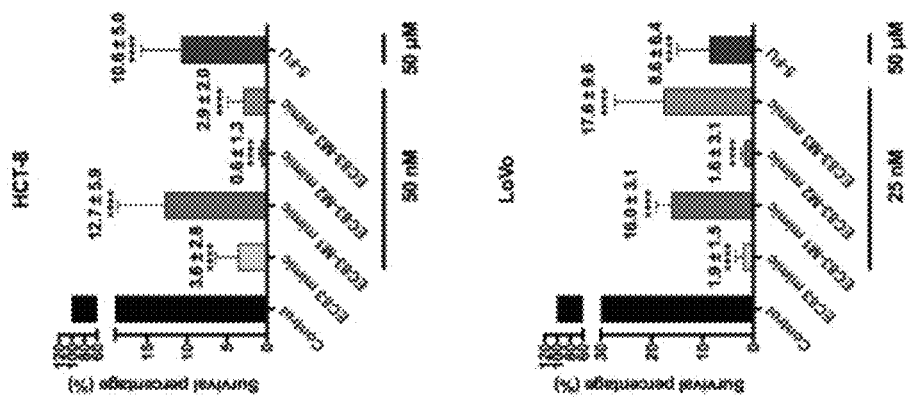
FIG. 9A shows the inhibition effects of RNA molecule EC83 mimic, EC83-M1 mimic, EC83-M2 mimic and EC83-M3 mimic derived from *Escherichia coli* (Migula) Castellani & Chalmers at a dose of 50 nM on the migration of HCT-8 cells in accordance with an example embodiment (mean±SD n=3; ****, p<0.0001 vs. vehicle control).
Figure 9A:
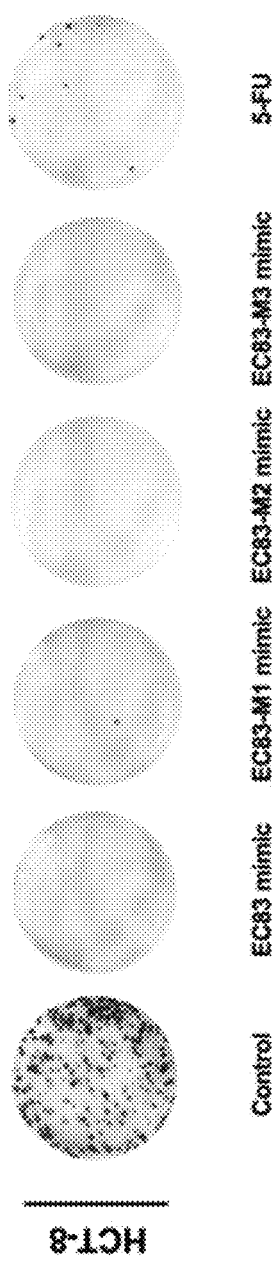
Figure 9B:
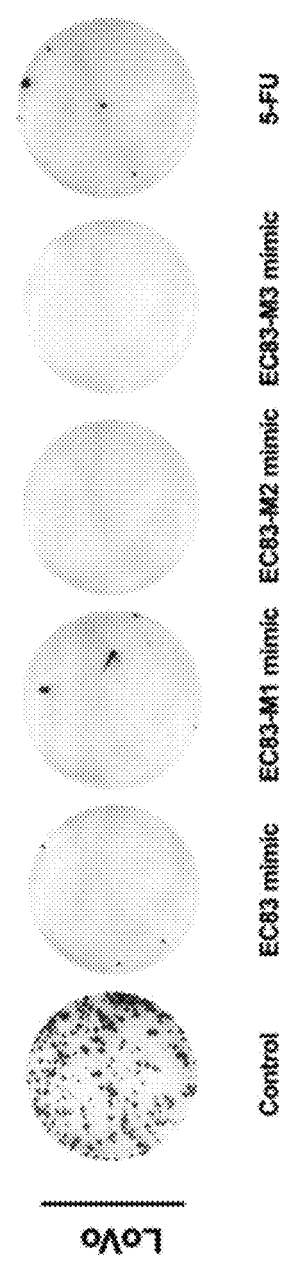
FIG. 9B shows the inhibition effects of RNA molecule EC83 mimic, EC83-M1 mimic, EC83-M2 mimic and EC83-M3 mimic derived from *Escherichia coli* (Migula) Castellani & Chalmers at a dose of 25 nM on the migration of LoVo cells in accordance with an example embodiment (mean±SD n=3; ****, p<0.0001 vs. vehicle control).

With reference to FIGS. 9A and 9B, HCT-8 cells and LoVo cells were treated with 50 nM or 25 nM RNA molecules of EC83 mimic and different chemically modified RNA molecules EC83-M1, EC83-M2 and EC83-M3 mimic. The wound area of these cells is compared to a control group. A comparative example using fluorouracil was conducted. The results show that these RNA molecules can significantly inhibit the migration of colorectal cancer cells. Specifically, EC83-M2 mimic exhibited the strongest inhibition effect on the wound healing of colorectal cancer cells.

NUMBERED EMBODIMENTS

The implementation is further described with reference to the following numbered embodiments.

Embodiment 1: A double-stranded RNA molecule comprising an antisense sequence selected from one of SEQ ID NO: 7 to SEQ ID NO: 100, and a sense sequence selected from one of SEQ ID NO: 101 to SEQ ID NO: 194; or a functional variant or homologue thereof.

Embodiment 2: The double-stranded RNA molecule of embodiment 1, wherein the antisense sequence is selected from one of SEQ ID NO: 47, 48, 89, 90, 91 and 92, and the sense sequence is selected from one of SEQ ID NO: 141, 142, 183, 184, 185 and 186; or a functional variant or homologue thereof.

Embodiment 3: The double-stranded RNA molecule of embodiment 1, wherein the antisense sequence is SEQ ID NO: 47, 48, 89, 90, 91 and 92, and the sense sequence is SEQ ID NO: 141, 142, 183, 184, 185 and 186; or a functional variant or homologue thereof.

Embodiment 4: The double-stranded RNA molecule of embodiment 1, wherein the antisense sequence is SEQ ID NO: 89, and the sense sequence is SEQ ID NO: 183; or a functional variant or homologue thereof.

Embodiment 5: The double-stranded RNA molecule of embodiment 1 comprising a 3' overhang; or a functional variant or homologue thereof.

Embodiment 6: The double-stranded RNA molecule of embodiment 1, wherein the antisense sequence and/or the sense sequence comprises one or more chemically modified nucleotides; wherein the one or more chemically modified nucleotides are selected from the group consisting of m1A, m2A, m5A, m7A, m2G, m6A, m22G, Um, i6A, ms2i6A, t6A, m6t6A, s2C, s2U, s4U, ac4C, f5C, acp3U, mo5U, cmo5U, mcmo5U, mcm5U, mcm5Um, mcm5s2U, nm5s2U, mnm5U, mnm5s2U, ncm5U, ncm5Um, cmnm5U, cmnm5Um, cmnm5s2U, tm5U and tm5s2U; or a functional variant or homologue thereof.

Embodiment 7: The double-stranded RNA molecule of embodiment 1, wherein the antisense sequence and/or the sense sequence comprises one or more chemically modified nucleotides; wherein the one or more chemically modified nucleotides are selected from the group consisting of m1A, m7G, m6A, Gm, Cm, Am, Um, m22G, s4U and cmo5U; or a functional variant or homologue thereof.

Embodiment 8: The double-stranded RNA molecule of embodiment 7, wherein the one or more chemically modified nucleotides are s4U and/or Gm; or a functional variant or homologue thereof.

Embodiment 9: The double-stranded RNA molecule of embodiment 1, wherein the antisense sequence and/or the sense sequence comprises at least one nucleotide having one or more chemical modifications; wherein the nucleotide is selected from the group consisting of adenosine, guanosine, cytidine and uridine; or a functional variant or homologue thereof; and the one or more chemical modifications is selected from the group consisting of 1-methyl, 2-methyl, 5-methyl, 7-methyl, N2 methyl, N6 methyl, N2,N2 dimethyl, 2'-O-methyl, N6-isopentenyl, 2-methylthio-N6-isopentenyl, N6 threonide carbamoyl, N6-methyl-N6-threosyl-carbamoyl, 2-thio, 4-thio, N4 acetyl, 5-formyl, 3-(3-amino-3-carboxypropyl), 5-methoxy, 5-oxoacetic acid, 5-oxoacetate methyl ester, 5-methoxycarbonylmethyl, 5-methoxycarbonylmethyl-2'-O-methyl, 5-methoxycarbonylmethyl-2-thio, 5-aminomethyl-2-thio, 5-methylaminomethyl, 5-methylaminomethyl-2-thio, 5-aminoformylmethyl, 5-aminoformylmethyl-2'-O-methyl, 5-carboxymethyl aminomethyl, 5-carbamoylmethyl-2'-O-methyl, 5-carboxymethylaminomethyl-2-methyl, 5-taurine, 5,2'-O-dimethyl, and 5-tauromethyl-2-thio.

Embodiment 10: The double-stranded RNA molecule of embodiment 9, wherein the one or more chemical modifications is selected from the group consisting of 1-methyl, 7-methyl, N6 methyl, 2'-O-methyl, 5,2'-O-dimethyl, 4-thio, and 5-oxoacetic acid.

Embodiment 11: The double-stranded RNA molecule of embodiment 9, wherein the nucleotide is uridine and/or guanosine; or a functional variant or homologue thereof.

Embodiment 12: A double-stranded RNA molecule comprising an antisense sequence selected from the group consisting of SEQ ID NO: 1, 2 and 3, and a sense sequence selected from the group consisting of SEQ ID NO: 4, 5 and 6; or a functional variant or homologue thereof.

Embodiment 13: The double-stranded RNA molecule embodiment 12, wherein the antisense sequence is SEQ ID NO: 1, 2 or 3, and the sense sequence is SEQ ID NO: 4, 5 or 6; or a functional variant or homologue thereof.

Embodiment 14: A pharmaceutical composition comprising the double-stranded RNA molecule of embodiment 1 or a functional variant or homolog thereof, and a pharmaceutically tolerable carrier, diluent and/or excipient.

Embodiment 15: The pharmaceutical composition of embodiment 14, wherein the pharmaceutical composition further comprises a nucleic acid stabilizer.

Embodiment 16: The pharmaceutical composition of embodiment 14, wherein the pharmaceutical composition is used for preventing and/or treating cancer, wherein the cancer is colorectal cancer or fluorouracil resistant cancer.

Embodiment 17: A method of preventing and/or treating cancer in a subject in need thereof, comprising administering an effective amount of the double-stranded RNA molecule of embodiment 1 to the subject.

Embodiment 18: The method of embodiment 17, wherein the cancer is colorectal cancer or fluorouracil resistant cancer.

What is claimed is:

1. A double-stranded RNA molecule comprising an antisense sequence selected from one of SEQ ID NO: 7 to SEQ ID NO: 70 and SEQ ID NO: 72 to SEQ ID NO: 100, and a sense sequence selected from one of SEQ ID NO: 101 to SEQ ID NO: 164 and SEQ ID NO: 166 to SEQ ID NO: 194.

2. The double-stranded RNA molecule of claim 1, wherein the antisense sequence is selected from one of SEQ ID NO: 47, 48, 89, 90, 91 and 92, and the sense sequence is selected from one of SEQ ID NO: 141, 142, 183, 184, 185 and 186.

3. The double-stranded RNA molecule of claim 1, wherein the antisense sequence is SEQ ID NO: 89, and the sense sequence is SEQ ID NO: 183.

4. The double-stranded RNA molecule of claim 1 comprising a 3' overhang.

5. The double-stranded RNA molecule of claim 1, wherein the antisense sequence and/or the sense sequence comprises one or more chemically modified nucleotides; wherein the one or more chemically modified nucleotides are selected from the group consisting of m1A, m2A, m5A, m7A, m2G, m6A, m22G, Um, i6A, ms2i6A, t6A, m6t6A, s2C, s2U, s4U, ac4C, f5C, acp3U, moSU, cmo5U, mcmo5U, mcm5U, mcm5Um, mcm5s2U, nm5s2U, mnm5U, mnm5s2U, ncm5U, ncm5Um, cmnm5U, cmnm5Um, cmnm5s2U, tm5U and tm5s2U.

6. The double-stranded RNA molecule of claim 1, wherein the antisense sequence and/or the sense sequence comprises one or more chemically modified nucleotides; wherein the one or more chemically modified nucleotides are selected from the group consisting of m1A, m7G, m6A, Gm, Cm, Am, Um, m22G, s4U and cmo5U.

7. The double-stranded RNA molecule of claim 6, wherein the one or more chemically modified nucleotides are s4U and/or Gm.

8. The double-stranded RNA molecule of claim 1, wherein the antisense sequence and/or the sense sequence comprises at least one nucleotide having one or more chemical modifications; wherein the nucleotide is selected from the group consisting of adenosine, guanosine, cytidine and uridine; and the one or more chemical modifications is selected from the group consisting of 1-methyl, 2-methyl, 5-methyl, 7-methyl, N2 methyl, N6 methyl, N2,N2 dimethyl, 2'-O-methyl, N6-isopentenyl, 2-methylthio-N6-isopentenyl, N6 threonide carbamoyl, N6-methyl-N6-threosyl-carbamoyl, 2-thio, 4-thio, N4 acetyl, 5-formyl, 3-(3-amino-3-carboxypropyl), 5-methoxy, 5-oxoacetic acid, 5-oxoacetate methyl ester, 5-methoxycarbonylmethyl, 5-methoxycarbonylmethyl-2'-O-methyl, 5-methoxycarbonylmethyl-2-thio, 5-aminomethyl-2-thio, 5-methylaminomethyl-2-thio, 5-aminoformylmethyl, 5-aminoformylmethyl-2'-O-methyl, 5-carboxymethyl aminomethyl, 5-carbamoylmethyl-2'-O-methyl, 5-carboxymethylaminomethyl-2-methyl, 5-taurine, 5,2'-O-dimethyl, and 5-tauromethyl-2-thio.

9. The double-stranded RNA molecule of claim 8, wherein the one or more chemical modifications is selected from the group consisting of 1-methyl, 7-methyl, N6 methyl, 2'-O-methyl, 5,2'-O-dimethyl, 4-thio, and 5-oxoacetic acid.

10. The double-stranded RNA molecule of claim 8, wherein the nucleotide is uridine and/or guanosine.

11. A double-stranded RNA molecule comprising an antisense sequence selected from the group consisting of SEQ ID NO: 1, 2 and 3, and a sense sequence selected from the group consisting of SEQ ID NO: 4, 5 and 6.

12. A pharmaceutical composition comprising the double-stranded RNA molecule of claim 1; and a pharmaceutically tolerable carrier, diluent and/or excipient.

13. The pharmaceutical composition of claim 12, wherein the pharmaceutical composition further comprises a nucleic acid stabilizer.

14. The pharmaceutical composition of claim 12, wherein the pharmaceutical composition is used for treating cancer, wherein the cancer is colorectal cancer or fluorouracil resistant cancer.

15. A method of treating cancer in a subject in need thereof, comprising administering an effective amount of the double-stranded RNA molecule of claim 1 to the subject.

16. The method of claim 15, wherein the cancer is colorectal cancer or fluorouracil resistant cancer.

* * * * *

SEQUENCE LISTING

<160> NUMBER OF SEQ ID NOS: 244

<210> SEQ ID NO 1
<211> LENGTH: 22
<212> TYPE: RNA
<213> ORGANISM: Artificial Sequence
<220> FEATURE:
<223> OTHER INFORMATION: Artificially synthesized
<220> FEATURE:
<221> NAME/KEY: modified_base
<222> LOCATION: (8)..(8)

<223> OTHER INFORMATION: u =s4u

<400> SEQUENCE: 1
gccgaagugg cgaaaucggu ag                                        22

<210> SEQ ID NO 2
<211> LENGTH: 22
<212> TYPE: RNA
<213> ORGANISM: Artificial Sequence
<220> FEATURE:
<223> OTHER INFORMATION: Artificially synthesized
<220> FEATURE:
<221> NAME/KEY: modified_base
<222> LOCATION: (18)..(18)
<223> OTHER INFORMATION: g =gm

<400> SEQUENCE: 2
gccgaagugg cgaaaucggu ag                                        22

<210> SEQ ID NO 3
<211> LENGTH: 22
<212> TYPE: RNA
<213> ORGANISM: Artificial Sequence
<220> FEATURE:
<223> OTHER INFORMATION: Artificially synthesized
<220> FEATURE:
<221> NAME/KEY: modified_base
<222> LOCATION: (8)..(8)
<223> OTHER INFORMATION: u =s4u
<220> FEATURE:
<221> NAME/KEY: modified_base
<222> LOCATION: (18)..(18)
<223> OTHER INFORMATION: g=gm

<400> SEQUENCE: 3
gccgaagugg cgaaaucggu ag                                        22

<210> SEQ ID NO 4
<211> LENGTH: 22
<212> TYPE: RNA
<213> ORGANISM: Artificial Sequence
<220> FEATURE:
<223> OTHER INFORMATION: Artificially synthesized

<400> SEQUENCE: 4
cuaccgauuu cgccacuucg gc                                        22

<210> SEQ ID NO 5
<211> LENGTH: 22
<212> TYPE: RNA
<213> ORGANISM: Artificial Sequence
<220> FEATURE:
<223> OTHER INFORMATION: Artificially synthesized

<400> SEQUENCE: 5
cuaccgauuu cgccacuucg gc                                        22

<210> SEQ ID NO 6
<211> LENGTH: 22
<212> TYPE: RNA
<213> ORGANISM: Artificial Sequence
<220> FEATURE:
<223> OTHER INFORMATION: Artificially synthesized

<400> SEQUENCE: 6
cuaccgauuu cgccacuucg gc                                        22

```
<210> SEQ ID NO 7
<211> LENGTH: 22
<212> TYPE: RNA
<213> ORGANISM: Artificial Sequence
<220> FEATURE:
<223> OTHER INFORMATION: Artificially synthesized

<400> SEQUENCE: 7
ggcgcguuaa caaagcgguu au                                              22

<210> SEQ ID NO 8
<211> LENGTH: 22
<212> TYPE: RNA
<213> ORGANISM: Artificial Sequence
<220> FEATURE:
<223> OTHER INFORMATION: Artificially synthesized

<400> SEQUENCE: 8
ucgacuccgg aacgcgccuc ca                                              22

<210> SEQ ID NO 9
<211> LENGTH: 22
<212> TYPE: RNA
<213> ORGANISM: Artificial Sequence
<220> FEATURE:
<223> OTHER INFORMATION: Artificially synthesized

<400> SEQUENCE: 9
gguggcuaua gcucaguugg ua                                              22

<210> SEQ ID NO 10
<211> LENGTH: 22
<212> TYPE: RNA
<213> ORGANISM: Artificial Sequence
<220> FEATURE:
<223> OTHER INFORMATION: Artificially synthesized

<400> SEQUENCE: 10
ucgaauccca uuagccaccc ca                                              22

<210> SEQ ID NO 11
<211> LENGTH: 22
<212> TYPE: RNA
<213> ORGANISM: Artificial Sequence
<220> FEATURE:
<223> OTHER INFORMATION: Artificially synthesized

<400> SEQUENCE: 11
gggucguuag cucaguuggu ag                                              22

<210> SEQ ID NO 12
<211> LENGTH: 22
<212> TYPE: RNA
<213> ORGANISM: Artificial Sequence
<220> FEATURE:
<223> OTHER INFORMATION: Artificially synthesized

<400> SEQUENCE: 12
ucgaauccug cacgacccac ca                                              22

<210> SEQ ID NO 13
<211> LENGTH: 22
<212> TYPE: RNA
<213> ORGANISM: Artificial Sequence
<220> FEATURE:
<223> OTHER INFORMATION: Artificially synthesized
```

<400> SEQUENCE: 13
ggcuacguag cucaguuggu ua					22

<210> SEQ ID NO 14
<211> LENGTH: 22
<212> TYPE: RNA
<213> ORGANISM: Artificial Sequence
<220> FEATURE:
<223> OTHER INFORMATION: Artificially synthesized

<400> SEQUENCE: 14
ucgaaucccg ucguagccac ca					22

<210> SEQ ID NO 15
<211> LENGTH: 22
<212> TYPE: RNA
<213> ORGANISM: Artificial Sequence
<220> FEATURE:
<223> OTHER INFORMATION: Artificially synthesized

<400> SEQUENCE: 15
uccucuguag uucagucggu ag					22

<210> SEQ ID NO 16
<211> LENGTH: 22
<212> TYPE: RNA
<213> ORGANISM: Artificial Sequence
<220> FEATURE:
<223> OTHER INFORMATION: Artificially synthesized

<400> SEQUENCE: 16
ucgaguccag ucagaggagc ca					22

<210> SEQ ID NO 17
<211> LENGTH: 22
<212> TYPE: RNA
<213> ORGANISM: Artificial Sequence
<220> FEATURE:
<223> OTHER INFORMATION: Artificially synthesized

<400> SEQUENCE: 17
gcccggauag cucagucggu ag					22

<210> SEQ ID NO 18
<211> LENGTH: 22
<212> TYPE: RNA
<213> ORGANISM: Artificial Sequence
<220> FEATURE:
<223> OTHER INFORMATION: Artificially synthesized

<400> SEQUENCE: 18
ucgauuccga guccgggcac ca					22

<210> SEQ ID NO 19
<211> LENGTH: 22
<212> TYPE: RNA
<213> ORGANISM: Artificial Sequence
<220> FEATURE:
<223> OTHER INFORMATION: Artificially synthesized

<400> SEQUENCE: 19
aggggcguag uucaauuggu ag					22

<210> SEQ ID NO 20
<211> LENGTH: 22

```
<212> TYPE: RNA
<213> ORGANISM: Artificial Sequence
<220> FEATURE:
<223> OTHER INFORMATION: Artificially synthesized

<400> SEQUENCE: 20
ucgagucucu ccgccccugc ca                                              22

<210> SEQ ID NO 21
<211> LENGTH: 22
<212> TYPE: RNA
<213> ORGANISM: Artificial Sequence
<220> FEATURE:
<223> OTHER INFORMATION: Artificially synthesized

<400> SEQUENCE: 21
ggagcgguag uucagucggu ua                                              22

<210> SEQ ID NO 22
<211> LENGTH: 22
<212> TYPE: RNA
<213> ORGANISM: Artificial Sequence
<220> FEATURE:
<223> OTHER INFORMATION: Artificially synthesized

<400> SEQUENCE: 22
ucgagucccg uccguuccgc ca                                              22

<210> SEQ ID NO 23
<211> LENGTH: 22
<212> TYPE: RNA
<213> ORGANISM: Artificial Sequence
<220> FEATURE:
<223> OTHER INFORMATION: Artificially synthesized

<400> SEQUENCE: 23
cggugauugg cgcagccugg ua                                              22

<210> SEQ ID NO 24
<211> LENGTH: 22
<212> TYPE: RNA
<213> ORGANISM: Artificial Sequence
<220> FEATURE:
<223> OTHER INFORMATION: Artificially synthesized

<400> SEQUENCE: 24
ucgaauccuc uaucaccgac ca                                              22

<210> SEQ ID NO 25
<211> LENGTH: 22
<212> TYPE: RNA
<213> ORGANISM: Artificial Sequence
<220> FEATURE:
<223> OTHER INFORMATION: Artificially synthesized

<400> SEQUENCE: 25
aagaucgucg ucuccgguga gg                                              22

<210> SEQ ID NO 26
<211> LENGTH: 22
<212> TYPE: RNA
<213> ORGANISM: Artificial Sequence
<220> FEATURE:
<223> OTHER INFORMATION: Artificially synthesized

<400> SEQUENCE: 26
```

-continued uucgacuccu gugaucuugc ca                                        22

<210> SEQ ID NO 27
<211> LENGTH: 22
<212> TYPE: RNA
<213> ORGANISM: Artificial Sequence
<220> FEATURE:
<223> OTHER INFORMATION: Artificially synthesized

<400> SEQUENCE: 27
ggggcuauag cucagcuggg ag                                        22

<210> SEQ ID NO 28
<211> LENGTH: 22
<212> TYPE: RNA
<213> ORGANISM: Artificial Sequence
<220> FEATURE:
<223> OTHER INFORMATION: Artificially synthesized

<400> SEQUENCE: 28
ucgaucccgc uuagcuccac ca                                        22

<210> SEQ ID NO 29
<211> LENGTH: 22
<212> TYPE: RNA
<213> ORGANISM: Artificial Sequence
<220> FEATURE:
<223> OTHER INFORMATION: Artificially synthesized

<400> SEQUENCE: 29
gggggcauag cucagcuggg ag                                        22

<210> SEQ ID NO 30
<211> LENGTH: 22
<212> TYPE: RNA
<213> ORGANISM: Artificial Sequence
<220> FEATURE:
<223> OTHER INFORMATION: Artificially synthesized

<400> SEQUENCE: 30
ucgaucccgc gcgcucccac ca                                        22

<210> SEQ ID NO 31
<211> LENGTH: 22
<212> TYPE: RNA
<213> ORGANISM: Artificial Sequence
<220> FEATURE:
<223> OTHER INFORMATION: Artificially synthesized

<400> SEQUENCE: 31
ggggcuauag cucagcuggg ag                                        22

<210> SEQ ID NO 32
<211> LENGTH: 22
<212> TYPE: RNA
<213> ORGANISM: Artificial Sequence
<220> FEATURE:
<223> OTHER INFORMATION: Artificially synthesized

<400> SEQUENCE: 32
ucgaucccgc auagcuccac ca                                        22

<210> SEQ ID NO 33
<211> LENGTH: 22
<212> TYPE: RNA
<213> ORGANISM: Artificial Sequence

```
<220> FEATURE:
<223> OTHER INFORMATION: Artificially synthesized

<400> SEQUENCE: 33
ggagagaugc cggagcggcu ga                                              22

<210> SEQ ID NO 34
<211> LENGTH: 22
<212> TYPE: RNA
<213> ORGANISM: Artificial Sequence
<220> FEATURE:
<223> OTHER INFORMATION: Artificially synthesized

<400> SEQUENCE: 34 ucaaauccccc cucucuccgc ca                                             22

<210> SEQ ID NO 35
<211> LENGTH: 22
<212> TYPE: RNA
<213> ORGANISM: Artificial Sequence
<220> FEATURE:
<223> OTHER INFORMATION: Artificially synthesized

<400> SEQUENCE: 35
ggugaggugg ccgagaggcu ga                                              22

<210> SEQ ID NO 36
<211> LENGTH: 22
<212> TYPE: RNA
<213> ORGANISM: Artificial Sequence
<220> FEATURE:
<223> OTHER INFORMATION: Artificially synthesized

<400> SEQUENCE: 36
ucgaaucccc gcccucaccgc ca                                             22

<210> SEQ ID NO 37
<211> LENGTH: 22
<212> TYPE: RNA
<213> ORGANISM: Artificial Sequence
<220> FEATURE:
<223> OTHER INFORMATION: Artificially synthesized

<400> SEQUENCE: 37
ggugaggugu ccgaguggcu ga                                              22

<210> SEQ ID NO 38
<211> LENGTH: 22
<212> TYPE: RNA
<213> ORGANISM: Artificial Sequence
<220> FEATURE:
<223> OTHER INFORMATION: Artificially synthesized

<400> SEQUENCE: 38 ucgaauccccc cccucaccgc ca                                             22

<210> SEQ ID NO 39
<211> LENGTH: 22
<212> TYPE: RNA
<213> ORGANISM: Artificial Sequence
<220> FEATURE:
<223> OTHER INFORMATION: Artificially synthesized

<400> SEQUENCE: 39
ggugaggugu ccgagugguu ga                                              22
```

```
<210> SEQ ID NO 40
<211> LENGTH: 22
<212> TYPE: RNA
<213> ORGANISM: Artificial Sequence
<220> FEATURE:
<223> OTHER INFORMATION: Artificially synthesized

<400> SEQUENCE: 40 ucgaauccccc cccucaccgc ca                                                22

<210> SEQ ID NO 41
<211> LENGTH: 22
<212> TYPE: RNA
<213> ORGANISM: Artificial Sequence
<220> FEATURE:
<223> OTHER INFORMATION: Artificially synthesized

<400> SEQUENCE: 41
ggaagugugg ccgagcgguu ga                                                 22

<210> SEQ ID NO 42
<211> LENGTH: 22
<212> TYPE: RNA
<213> ORGANISM: Artificial Sequence
<220> FEATURE:
<223> OTHER INFORMATION: Artificially synthesized

<400> SEQUENCE: 42
ucgaaucucu gcgcuuccgc ca                                                 22

<210> SEQ ID NO 43
<211> LENGTH: 22
<212> TYPE: RNA
<213> ORGANISM: Artificial Sequence
<220> FEATURE:
<223> OTHER INFORMATION: Artificially synthesized

<400> SEQUENCE: 43
gcguccguag cucaguuggu ua                                                 22

<210> SEQ ID NO 44
<211> LENGTH: 22
<212> TYPE: RNA
<213> ORGANISM: Artificial Sequence
<220> FEATURE:
<223> OTHER INFORMATION: Artificially synthesized

<400> SEQUENCE: 44
ucgaguccac ucggacgcac ca                                                 22

<210> SEQ ID NO 45
<211> LENGTH: 22
<212> TYPE: RNA
<213> ORGANISM: Artificial Sequence
<220> FEATURE:
<223> OTHER INFORMATION: Artificially synthesized

<400> SEQUENCE: 45
gcguucauag cucaguuggu ua                                                 22

<210> SEQ ID NO 46
<211> LENGTH: 22
<212> TYPE: RNA
<213> ORGANISM: Artificial Sequence
<220> FEATURE:
<223> OTHER INFORMATION: Artificially synthesized
```

```
<400> SEQUENCE: 46
ucgaguccaa uugaacgcac ca                                              22

<210> SEQ ID NO 47
<211> LENGTH: 22
<212> TYPE: RNA
<213> ORGANISM: Artificial Sequence
<220> FEATURE:
<223> OTHER INFORMATION: Artificially synthesized

<400> SEQUENCE: 47
gggugauuag cucagcuggg ag                                              22

<210> SEQ ID NO 48
<211> LENGTH: 22
<212> TYPE: RNA
<213> ORGANISM: Artificial Sequence
<220> FEATURE:
<223> OTHER INFORMATION: Artificially synthesized

<400> SEQUENCE: 48
ucgaucccgu caucacccac ca                                              22

<210> SEQ ID NO 49
<211> LENGTH: 22
<212> TYPE: RNA
<213> ORGANISM: Artificial Sequence
<220> FEATURE:
<223> OTHER INFORMATION: Artificially synthesized

<400> SEQUENCE: 49
gcgcccguag cucagcugga ua                                              22

<210> SEQ ID NO 50
<211> LENGTH: 22
<212> TYPE: RNA
<213> ORGANISM: Artificial Sequence
<220> FEATURE:
<223> OTHER INFORMATION: Artificially synthesized

<400> SEQUENCE: 50
ucgaauccug ucgggcgcgc ca                                              22

<210> SEQ ID NO 51
<211> LENGTH: 22
<212> TYPE: RNA
<213> ORGANISM: Artificial Sequence
<220> FEATURE:
<223> OTHER INFORMATION: Artificially synthesized

<400> SEQUENCE: 51
gcauccguag cucagcuggu ag                                              22

<210> SEQ ID NO 52
<211> LENGTH: 22
<212> TYPE: RNA
<213> ORGANISM: Artificial Sequence
<220> FEATURE:
<223> OTHER INFORMATION: Artificially synthesized

<400> SEQUENCE: 52
ucgaauccuc ccggaugcac ca                                              22

<210> SEQ ID NO 53
```

```
<211> LENGTH: 22
<212> TYPE: RNA
<213> ORGANISM: Artificial Sequence
<220> FEATURE:
<223> OTHER INFORMATION: Artificially synthesized

<400> SEQUENCE: 53
gcauccguag cucagcugga ua                                                  22

<210> SEQ ID NO 54
<211> LENGTH: 22
<212> TYPE: RNA
<213> ORGANISM: Artificial Sequence
<220> FEATURE:
<223> OTHER INFORMATION: Artificially synthesized

<400> SEQUENCE: 54
ucgaauccuc ccggaugcac ca                                                  22

<210> SEQ ID NO 55
<211> LENGTH: 22
<212> TYPE: RNA
<213> ORGANISM: Artificial Sequence
<220> FEATURE:
<223> OTHER INFORMATION: Artificially synthesized

<400> SEQUENCE: 55
guccucuuag uuaaauggau au                                                  22

<210> SEQ ID NO 56
<211> LENGTH: 22
<212> TYPE: RNA
<213> ORGANISM: Artificial Sequence
<220> FEATURE:
<223> OTHER INFORMATION: Artificially synthesized

<400> SEQUENCE: 56
ucgauuccug cagggacac ca                                                   22

<210> SEQ ID NO 57
<211> LENGTH: 22
<212> TYPE: RNA
<213> ORGANISM: Artificial Sequence
<220> FEATURE:
<223> OTHER INFORMATION: Artificially synthesized

<400> SEQUENCE: 57
gcgcccuuag cucaguugga ua                                                  22

<210> SEQ ID NO 58
<211> LENGTH: 22
<212> TYPE: RNA
<213> ORGANISM: Artificial Sequence
<220> FEATURE:
<223> OTHER INFORMATION: Artificially synthesized

<400> SEQUENCE: 58
ucgaauccug cagggcgcgc ca                                                  22

<210> SEQ ID NO 59
<211> LENGTH: 22
<212> TYPE: RNA
<213> ORGANISM: Artificial Sequence
<220> FEATURE:
<223> OTHER INFORMATION: Artificially synthesized

<400> SEQUENCE: 59
```
ugggguaucg ccaagcggua ag                                              22

<210> SEQ ID NO 60
<211> LENGTH: 22
<212> TYPE: RNA
<213> ORGANISM: Artificial Sequence
<220> FEATURE:
<223> OTHER INFORMATION: Artificially synthesized

<400> SEQUENCE: 60
ucgaauccuc guaccccagc ca                                              22

<210> SEQ ID NO 61
<211> LENGTH: 22
<212> TYPE: RNA
<213> ORGANISM: Artificial Sequence
<220> FEATURE:
<223> OTHER INFORMATION: Artificially synthesized

<400> SEQUENCE: 61
ugggguaucg ccaagcggua ag                                              22

<210> SEQ ID NO 62
<211> LENGTH: 22
<212> TYPE: RNA
<213> ORGANISM: Artificial Sequence
<220> FEATURE:
<223> OTHER INFORMATION: Artificially synthesized

<400> SEQUENCE: 62
ucgaauccag guaccccagc ca                                              22

<210> SEQ ID NO 63
<211> LENGTH: 22
<212> TYPE: RNA
<213> ORGANISM: Artificial Sequence
<220> FEATURE:
<223> OTHER INFORMATION: Artificially synthesized

<400> SEQUENCE: 63
aggcuuguag cucagguggu ua                                              22

<210> SEQ ID NO 64
<211> LENGTH: 22
<212> TYPE: RNA
<213> ORGANISM: Artificial Sequence
<220> FEATURE:
<223> OTHER INFORMATION: Artificially synthesized

<400> SEQUENCE: 64
ucaaguccac ucaggccuac ca                                              22

<210> SEQ ID NO 65
<211> LENGTH: 22
<212> TYPE: RNA
<213> ORGANISM: Artificial Sequence
<220> FEATURE:
<223> OTHER INFORMATION: Artificially synthesized

<400> SEQUENCE: 65
aggcuuguag cucagguggu ua                                              22

<210> SEQ ID NO 66
<211> LENGTH: 22
<212> TYPE: RNA

```
<213> ORGANISM: Artificial Sequence
<220> FEATURE:
<223> OTHER INFORMATION: Artificially synthesized

<400> SEQUENCE: 66
ucaaguccac ucaggccuac ca                                              22

<210> SEQ ID NO 67
<211> LENGTH: 22
<212> TYPE: RNA
<213> ORGANISM: Artificial Sequence
<220> FEATURE:
<223> OTHER INFORMATION: Artificially synthesized

<400> SEQUENCE: 67 ggcccuuag cucagugguu ag                                               22

<210> SEQ ID NO 68
<211> LENGTH: 22
<212> TYPE: RNA
<213> ORGANISM: Artificial Sequence
<220> FEATURE:
<223> OTHER INFORMATION: Artificially synthesized

<400> SEQUENCE: 68
ucaaguccag cagggggccac ca                                             22

<210> SEQ ID NO 69
<211> LENGTH: 22
<212> TYPE: RNA
<213> ORGANISM: Artificial Sequence
<220> FEATURE:
<223> OTHER INFORMATION: Artificially synthesized

<400> SEQUENCE: 69
gcugauauag cucaguuggu ag                                              22

<210> SEQ ID NO 70
<211> LENGTH: 22
<212> TYPE: RNA
<213> ORGANISM: Artificial Sequence
<220> FEATURE:
<223> OTHER INFORMATION: Artificially synthesized

<400> SEQUENCE: 70
ucgaaucugc cuaucagcac ca                                              22

<210> SEQ ID NO 71
<211> LENGTH: 22
<212> TYPE: RNA
<213> ORGANISM: Artificial Sequence
<220> FEATURE:
<223> OTHER INFORMATION: Artificially synthesized

<400> SEQUENCE: 71
gcugauaugg cucaguuggu ag                                              22

<210> SEQ ID NO 72
<211> LENGTH: 22
<212> TYPE: RNA
<213> ORGANISM: Artificial Sequence
<220> FEATURE:
<223> OTHER INFORMATION: Artificially synthesized

<400> SEQUENCE: 72
ucgacucugg guaucagcac ca                                              22
```

<210> SEQ ID NO 73
<211> LENGTH: 22
<212> TYPE: RNA
<213> ORGANISM: Artificial Sequence
<220> FEATURE:
<223> OTHER INFORMATION: Artificially synthesized

<400> SEQUENCE: 73 gucccccuucg ucuagaggcc ca                                    22

<210> SEQ ID NO 74
<211> LENGTH: 22
<212> TYPE: RNA
<213> ORGANISM: Artificial Sequence
<220> FEATURE:
<223> OTHER INFORMATION: Artificially synthesized

<400> SEQUENCE: 74 ucgaauccccc uggggacgc ca                                     22

<210> SEQ ID NO 75
<211> LENGTH: 22
<212> TYPE: RNA
<213> ORGANISM: Artificial Sequence
<220> FEATURE:
<223> OTHER INFORMATION: Artificially synthesized

<400> SEQUENCE: 75 gucccccuucg ucuagaggcc ca                                    22

<210> SEQ ID NO 76
<211> LENGTH: 22
<212> TYPE: RNA
<213> ORGANISM: Artificial Sequence
<220> FEATURE:
<223> OTHER INFORMATION: Artificially synthesized

<400> SEQUENCE: 76 ucgaauccccc uagggacgc ca                                     22

<210> SEQ ID NO 77
<211> LENGTH: 22
<212> TYPE: RNA
<213> ORGANISM: Artificial Sequence
<220> FEATURE:
<223> OTHER INFORMATION: Artificially synthesized

<400> SEQUENCE: 77 gucccccuucg ucuagaggcc ag                                    22

<210> SEQ ID NO 78
<211> LENGTH: 22
<212> TYPE: RNA
<213> ORGANISM: Artificial Sequence
<220> FEATURE:
<223> OTHER INFORMATION: Artificially synthesized

<400> SEQUENCE: 78 ucgaauccccc uagggacgc ca                                     22

<210> SEQ ID NO 79
<211> LENGTH: 22
<212> TYPE: RNA
<213> ORGANISM: Artificial Sequence
<220> FEATURE:

<223> OTHER INFORMATION: Artificially synthesized

<400> SEQUENCE: 79
cgcggggugg agcagccugg ua                                                22

<210> SEQ ID NO 80
<211> LENGTH: 22
<212> TYPE: RNA
<213> ORGANISM: Artificial Sequence
<220> FEATURE:
<223> OTHER INFORMATION: Artificially synthesized

<400> SEQUENCE: 80
ucaaauccgg cccccgcaac ca                                                22

<210> SEQ ID NO 81
<211> LENGTH: 22
<212> TYPE: RNA
<213> ORGANISM: Artificial Sequence
<220> FEATURE:
<223> OTHER INFORMATION: Artificially synthesized

<400> SEQUENCE: 81
cgcggggugg agcagccugg ua                                                22

<210> SEQ ID NO 82
<211> LENGTH: 22
<212> TYPE: RNA
<213> ORGANISM: Artificial Sequence
<220> FEATURE:
<223> OTHER INFORMATION: Artificially synthesized

<400> SEQUENCE: 82
ucaaauccgg cccccgcaac ca                                                22

<210> SEQ ID NO 83
<211> LENGTH: 22
<212> TYPE: RNA
<213> ORGANISM: Artificial Sequence
<220> FEATURE:
<223> OTHER INFORMATION: Artificially synthesized

<400> SEQUENCE: 83
gcgggcguag uucaauggua ga                                                22

<210> SEQ ID NO 84
<211> LENGTH: 22
<212> TYPE: RNA
<213> ORGANISM: Artificial Sequence
<220> FEATURE:
<223> OTHER INFORMATION: Artificially synthesized

<400> SEQUENCE: 84
ucgauucccu ucgcccgcuc ca                                                22

<210> SEQ ID NO 85
<211> LENGTH: 22
<212> TYPE: RNA
<213> ORGANISM: Artificial Sequence
<220> FEATURE:
<223> OTHER INFORMATION: Artificially synthesized

<400> SEQUENCE: 85
gcgggaauag cucaguuggu ag                                                22

```
<210> SEQ ID NO 86
<211> LENGTH: 22
<212> TYPE: RNA
<213> ORGANISM: Artificial Sequence
<220> FEATURE:
<223> OTHER INFORMATION: Artificially synthesized

<400> SEQUENCE: 86
ucgagucucg uuucccgcuc ca                                              22

<210> SEQ ID NO 87
<211> LENGTH: 22
<212> TYPE: RNA
<213> ORGANISM: Artificial Sequence
<220> FEATURE:
<223> OTHER INFORMATION: Artificially synthesized

<400> SEQUENCE: 87
gcgggcaucg uauaauggcu au                                              22

<210> SEQ ID NO 88
<211> LENGTH: 22
<212> TYPE: RNA
<213> ORGANISM: Artificial Sequence
<220> FEATURE:
<223> OTHER INFORMATION: Artificially synthesized

<400> SEQUENCE: 88
ucgauucccg cugcccgcuc ca                                              22

<210> SEQ ID NO 89
<211> LENGTH: 22
<212> TYPE: RNA
<213> ORGANISM: Artificial Sequence
<220> FEATURE:
<223> OTHER INFORMATION: Artificially synthesized

<400> SEQUENCE: 89
gccgaagugg cgaaaucggu ag                                              22

<210> SEQ ID NO 90
<211> LENGTH: 22
<212> TYPE: RNA
<213> ORGANISM: Artificial Sequence
<220> FEATURE:
<223> OTHER INFORMATION: Artificially synthesized

<400> SEQUENCE: 90
ucgaguccgg ccuucggcac ca                                              22

<210> SEQ ID NO 91
<211> LENGTH: 22
<212> TYPE: RNA
<213> ORGANISM: Artificial Sequence
<220> FEATURE:
<223> OTHER INFORMATION: Artificially synthesized

<400> SEQUENCE: 91
gcgaaggugg cggaauuggu ag                                              22

<210> SEQ ID NO 92
<211> LENGTH: 22
<212> TYPE: RNA
<213> ORGANISM: Artificial Sequence
<220> FEATURE:
<223> OTHER INFORMATION: Artificially synthesized
```

```
<400> SEQUENCE: 92
ucaagucccc ccccucgcac ca                                        22

<210> SEQ ID NO 93
<211> LENGTH: 22
<212> TYPE: RNA
<213> ORGANISM: Artificial Sequence
<220> FEATURE:
<223> OTHER INFORMATION: Artificially synthesized

<400> SEQUENCE: 93
gccgaggugg uggaauuggg ag                                        22

<210> SEQ ID NO 94
<211> LENGTH: 22
<212> TYPE: RNA
<213> ORGANISM: Artificial Sequence
<220> FEATURE:
<223> OTHER INFORMATION: Artificially synthesized

<400> SEQUENCE: 94
ucaagucccg uccucgguac ca                                        22

<210> SEQ ID NO 95
<211> LENGTH: 22
<212> TYPE: RNA
<213> ORGANISM: Artificial Sequence
<220> FEATURE:
<223> OTHER INFORMATION: Artificially synthesized

<400> SEQUENCE: 95
gcccggaugg uggaaucggu ag                                        22

<210> SEQ ID NO 96
<211> LENGTH: 22
<212> TYPE: RNA
<213> ORGANISM: Artificial Sequence
<220> FEATURE:
<223> OTHER INFORMATION: Artificially synthesized

<400> SEQUENCE: 96
ucaagucccg cuccggguac ca                                        22

<210> SEQ ID NO 97
<211> LENGTH: 22
<212> TYPE: RNA
<213> ORGANISM: Artificial Sequence
<220> FEATURE:
<223> OTHER INFORMATION: Artificially synthesized

<400> SEQUENCE: 97 gguggguuc ccgagcggcc aa                                         22

<210> SEQ ID NO 98
<211> LENGTH: 22
<212> TYPE: RNA
<213> ORGANISM: Artificial Sequence
<220> FEATURE:
<223> OTHER INFORMATION: Artificially synthesized

<400> SEQUENCE: 98
ucgaauccuu cccccaccac ca                                        22

<210> SEQ ID NO 99
<211> LENGTH: 22
```

```
<212> TYPE: RNA
<213> ORGANISM: Artificial Sequence
<220> FEATURE:
<223> OTHER INFORMATION: Artificially synthesized

<400> SEQUENCE: 99 gguggguuc ccgagcggcc aa                                            22

<210> SEQ ID NO 100
<211> LENGTH: 22
<212> TYPE: RNA
<213> ORGANISM: Artificial Sequence
<220> FEATURE:
<223> OTHER INFORMATION: Artificially synthesized

<400> SEQUENCE: 100
ucgaauccuu cccccaccac ca                                           22

<210> SEQ ID NO 101
<211> LENGTH: 22
<212> TYPE: RNA
<213> ORGANISM: Artificial Sequence
<220> FEATURE:
<223> OTHER INFORMATION: Artificially synthesized

<400> SEQUENCE: 101
auaaccgcuu uguuaacgcg cc                                           22

<210> SEQ ID NO 102
<211> LENGTH: 22
<212> TYPE: RNA
<213> ORGANISM: Artificial Sequence
<220> FEATURE:
<223> OTHER INFORMATION: Artificially synthesized

<400> SEQUENCE: 102
uggaggcgcg uuccggaguc ga                                           22

<210> SEQ ID NO 103
<211> LENGTH: 22
<212> TYPE: RNA
<213> ORGANISM: Artificial Sequence
<220> FEATURE:
<223> OTHER INFORMATION: Artificially synthesized

<400> SEQUENCE: 103
uaccaacuga gcuauagcca cc                                           22

<210> SEQ ID NO 104
<211> LENGTH: 22
<212> TYPE: RNA
<213> ORGANISM: Artificial Sequence
<220> FEATURE:
<223> OTHER INFORMATION: Artificially synthesized

<400> SEQUENCE: 104
ugggguggcu aaugggauuc ga                                           22

<210> SEQ ID NO 105
<211> LENGTH: 22
<212> TYPE: RNA
<213> ORGANISM: Artificial Sequence
<220> FEATURE:
<223> OTHER INFORMATION: Artificially synthesized

<400> SEQUENCE: 105
```
cuaccaacug agcuaacgac cc                                              22

<210> SEQ ID NO 106
<211> LENGTH: 22
<212> TYPE: RNA
<213> ORGANISM: Artificial Sequence
<220> FEATURE:
<223> OTHER INFORMATION: Artificially synthesized

<400> SEQUENCE: 106
uggugggucg ugcaggauuc ga                                              22

<210> SEQ ID NO 107
<211> LENGTH: 22
<212> TYPE: RNA
<213> ORGANISM: Artificial Sequence
<220> FEATURE:
<223> OTHER INFORMATION: Artificially synthesized

<400> SEQUENCE: 107
uaaccaacug agcuacguag cc                                              22

<210> SEQ ID NO 108
<211> LENGTH: 22
<212> TYPE: RNA
<213> ORGANISM: Artificial Sequence
<220> FEATURE:
<223> OTHER INFORMATION: Artificially synthesized

<400> SEQUENCE: 108
ugguggcuac gacgggauuc ga                                              22

<210> SEQ ID NO 109
<211> LENGTH: 22
<212> TYPE: RNA
<213> ORGANISM: Artificial Sequence
<220> FEATURE:
<223> OTHER INFORMATION: Artificially synthesized

<400> SEQUENCE: 109
cuaccgacug aacuacagag ga                                              22

<210> SEQ ID NO 110
<211> LENGTH: 22
<212> TYPE: RNA
<213> ORGANISM: Artificial Sequence
<220> FEATURE:
<223> OTHER INFORMATION: Artificially synthesized

<400> SEQUENCE: 110
uggcuccucu gacuggacuc ga                                              22

<210> SEQ ID NO 111
<211> LENGTH: 22
<212> TYPE: RNA
<213> ORGANISM: Artificial Sequence
<220> FEATURE:
<223> OTHER INFORMATION: Artificially synthesized

<400> SEQUENCE: 111
cuaccgacug agcuauccgg gc                                              22

<210> SEQ ID NO 112
<211> LENGTH: 22
<212> TYPE: RNA
<213> ORGANISM: Artificial Sequence

```
<220> FEATURE:
<223> OTHER INFORMATION: Artificially synthesized

<400> SEQUENCE: 112
uggugcccgg acucggaauc ga                                              22

<210> SEQ ID NO 113
<211> LENGTH: 22
<212> TYPE: RNA
<213> ORGANISM: Artificial Sequence
<220> FEATURE:
<223> OTHER INFORMATION: Artificially synthesized

<400> SEQUENCE: 113
cuaccaauug aacuacgccc cu                                              22

<210> SEQ ID NO 114
<211> LENGTH: 22
<212> TYPE: RNA
<213> ORGANISM: Artificial Sequence
<220> FEATURE:
<223> OTHER INFORMATION: Artificially synthesized

<400> SEQUENCE: 114
uggcaggggc ggagagacuc ga                                              22

<210> SEQ ID NO 115
<211> LENGTH: 22
<212> TYPE: RNA
<213> ORGANISM: Artificial Sequence
<220> FEATURE:
<223> OTHER INFORMATION: Artificially synthesized

<400> SEQUENCE: 115
uaaccgacug aacuaccgcu cc                                              22

<210> SEQ ID NO 116
<211> LENGTH: 22
<212> TYPE: RNA
<213> ORGANISM: Artificial Sequence
<220> FEATURE:
<223> OTHER INFORMATION: Artificially synthesized

<400> SEQUENCE: 116
uggcggaacg gacgggacuc ga                                              22

<210> SEQ ID NO 117
<211> LENGTH: 22
<212> TYPE: RNA
<213> ORGANISM: Artificial Sequence
<220> FEATURE:
<223> OTHER INFORMATION: Artificially synthesized

<400> SEQUENCE: 117
uaccaggcug cgccaaucac cg                                              22

<210> SEQ ID NO 118
<211> LENGTH: 22
<212> TYPE: RNA
<213> ORGANISM: Artificial Sequence
<220> FEATURE:
<223> OTHER INFORMATION: Artificially synthesized

<400> SEQUENCE: 118
uggucgguga uagaggauuc ga                                              22
```

<210> SEQ ID NO 119
<211> LENGTH: 22
<212> TYPE: RNA
<213> ORGANISM: Artificial Sequence
<220> FEATURE:
<223> OTHER INFORMATION: Artificially synthesized

<400> SEQUENCE: 119
ccucaccgga gacgacgauc uu                                               22

<210> SEQ ID NO 120
<211> LENGTH: 22
<212> TYPE: RNA
<213> ORGANISM: Artificial Sequence
<220> FEATURE:
<223> OTHER INFORMATION: Artificially synthesized

<400> SEQUENCE: 120
uggcaagauc acaggagucg aa                                               22

<210> SEQ ID NO 121
<211> LENGTH: 22
<212> TYPE: RNA
<213> ORGANISM: Artificial Sequence
<220> FEATURE:
<223> OTHER INFORMATION: Artificially synthesized

<400> SEQUENCE: 121
cucccagcug agcuauagcc cc                                               22

<210> SEQ ID NO 122
<211> LENGTH: 22
<212> TYPE: RNA
<213> ORGANISM: Artificial Sequence
<220> FEATURE:
<223> OTHER INFORMATION: Artificially synthesized

<400> SEQUENCE: 122
ugguggagcu aagcgggauc ga                                               22

<210> SEQ ID NO 123
<211> LENGTH: 22
<212> TYPE: RNA
<213> ORGANISM: Artificial Sequence
<220> FEATURE:
<223> OTHER INFORMATION: Artificially synthesized

<400> SEQUENCE: 123
cucccagcug agcuaugccc cc                                               22

<210> SEQ ID NO 124
<211> LENGTH: 22
<212> TYPE: RNA
<213> ORGANISM: Artificial Sequence
<220> FEATURE:
<223> OTHER INFORMATION: Artificially synthesized

<400> SEQUENCE: 124
uggugggagc gcgcgggauc ga                                               22

<210> SEQ ID NO 125
<211> LENGTH: 22
<212> TYPE: RNA
<213> ORGANISM: Artificial Sequence
<220> FEATURE:
<223> OTHER INFORMATION: Artificially synthesized

```
<400> SEQUENCE: 125
cucccagcug agcuauagcc cc                                           22

<210> SEQ ID NO 126
<211> LENGTH: 22
<212> TYPE: RNA
<213> ORGANISM: Artificial Sequence
<220> FEATURE:
<223> OTHER INFORMATION: Artificially synthesized

<400> SEQUENCE: 126
ugguggagcu augcgggauc ga                                           22

<210> SEQ ID NO 127
<211> LENGTH: 22
<212> TYPE: RNA
<213> ORGANISM: Artificial Sequence
<220> FEATURE:
<223> OTHER INFORMATION: Artificially synthesized

<400> SEQUENCE: 127
ucagccgcuc cggcaucucu cc                                           22

<210> SEQ ID NO 128
<211> LENGTH: 22
<212> TYPE: RNA
<213> ORGANISM: Artificial Sequence
<220> FEATURE:
<223> OTHER INFORMATION: Artificially synthesized

<400> SEQUENCE: 128
uggcggagag aggggauuu ga                                            22

<210> SEQ ID NO 129
<211> LENGTH: 22
<212> TYPE: RNA
<213> ORGANISM: Artificial Sequence
<220> FEATURE:
<223> OTHER INFORMATION: Artificially synthesized

<400> SEQUENCE: 129
ucagccucuc ggccaccuca cc                                           22

<210> SEQ ID NO 130
<211> LENGTH: 22
<212> TYPE: RNA
<213> ORGANISM: Artificial Sequence
<220> FEATURE:
<223> OTHER INFORMATION: Artificially synthesized

<400> SEQUENCE: 130
uggcggugag gcggggauuc ga                                           22

<210> SEQ ID NO 131
<211> LENGTH: 22
<212> TYPE: RNA
<213> ORGANISM: Artificial Sequence
<220> FEATURE:
<223> OTHER INFORMATION: Artificially synthesized

<400> SEQUENCE: 131
ucagccacuc ggacaccuca cc                                           22

<210> SEQ ID NO 132
```

```
<211> LENGTH: 22
<212> TYPE: RNA
<213> ORGANISM: Artificial Sequence
<220> FEATURE:
<223> OTHER INFORMATION: Artificially synthesized

<400> SEQUENCE: 132
uggcggugag gggggauuc ga                                              22

<210> SEQ ID NO 133
<211> LENGTH: 22
<212> TYPE: RNA
<213> ORGANISM: Artificial Sequence
<220> FEATURE:
<223> OTHER INFORMATION: Artificially synthesized

<400> SEQUENCE: 133
ucaaccacuc ggacaccuca cc                                             22

<210> SEQ ID NO 134
<211> LENGTH: 22
<212> TYPE: RNA
<213> ORGANISM: Artificial Sequence
<220> FEATURE:
<223> OTHER INFORMATION: Artificially synthesized

<400> SEQUENCE: 134
uggcggugag gggggauuc ga                                              22

<210> SEQ ID NO 135
<211> LENGTH: 22
<212> TYPE: RNA
<213> ORGANISM: Artificial Sequence
<220> FEATURE:
<223> OTHER INFORMATION: Artificially synthesized

<400> SEQUENCE: 135
ucaaccgcuc ggccacacuu cc                                             22

<210> SEQ ID NO 136
<211> LENGTH: 22
<212> TYPE: RNA
<213> ORGANISM: Artificial Sequence
<220> FEATURE:
<223> OTHER INFORMATION: Artificially synthesized

<400> SEQUENCE: 136
uggcggaagc gcagagauuc ga                                             22

<210> SEQ ID NO 137
<211> LENGTH: 22
<212> TYPE: RNA
<213> ORGANISM: Artificial Sequence
<220> FEATURE:
<223> OTHER INFORMATION: Artificially synthesized

<400> SEQUENCE: 137
uaaccaacug agcuacggac gc                                             22

<210> SEQ ID NO 138
<211> LENGTH: 22
<212> TYPE: RNA
<213> ORGANISM: Artificial Sequence
<220> FEATURE:
<223> OTHER INFORMATION: Artificially synthesized

<400> SEQUENCE: 138
```
uggugcgucc gaguggacuc ga                                              22

<210> SEQ ID NO 139
<211> LENGTH: 22
<212> TYPE: RNA
<213> ORGANISM: Artificial Sequence
<220> FEATURE:
<223> OTHER INFORMATION: Artificially synthesized

<400> SEQUENCE: 139
uaaccaacug agcuaugaac gc                                              22

<210> SEQ ID NO 140
<211> LENGTH: 22
<212> TYPE: RNA
<213> ORGANISM: Artificial Sequence
<220> FEATURE:
<223> OTHER INFORMATION: Artificially synthesized

<400> SEQUENCE: 140
uggugcguuc aauuggacuc ga                                              22

<210> SEQ ID NO 141
<211> LENGTH: 22
<212> TYPE: RNA
<213> ORGANISM: Artificial Sequence
<220> FEATURE:
<223> OTHER INFORMATION: Artificially synthesized

<400> SEQUENCE: 141
cucccagcug agcuaaucac cc                                              22

<210> SEQ ID NO 142
<211> LENGTH: 22
<212> TYPE: RNA
<213> ORGANISM: Artificial Sequence
<220> FEATURE:
<223> OTHER INFORMATION: Artificially synthesized

<400> SEQUENCE: 142 uggugggguga ugacgggauc ga                                             22

<210> SEQ ID NO 143
<211> LENGTH: 22
<212> TYPE: RNA
<213> ORGANISM: Artificial Sequence
<220> FEATURE:
<223> OTHER INFORMATION: Artificially synthesized

<400> SEQUENCE: 143
uauccagcug agcuacgggc gc                                              22

<210> SEQ ID NO 144
<211> LENGTH: 22
<212> TYPE: RNA
<213> ORGANISM: Artificial Sequence
<220> FEATURE:
<223> OTHER INFORMATION: Artificially synthesized

<400> SEQUENCE: 144
uggcgcgccc gacaggauuc ga                                              22

<210> SEQ ID NO 145
<211> LENGTH: 22
<212> TYPE: RNA

```
<213> ORGANISM: Artificial Sequence
<220> FEATURE:
<223> OTHER INFORMATION: Artificially synthesized

<400> SEQUENCE: 145
cuaccagcug agcuacggau gc                                              22

<210> SEQ ID NO 146
<211> LENGTH: 22
<212> TYPE: RNA
<213> ORGANISM: Artificial Sequence
<220> FEATURE:
<223> OTHER INFORMATION: Artificially synthesized

<400> SEQUENCE: 146
uggugcaucc gggaggauuc ga                                              22

<210> SEQ ID NO 147
<211> LENGTH: 22
<212> TYPE: RNA
<213> ORGANISM: Artificial Sequence
<220> FEATURE:
<223> OTHER INFORMATION: Artificially synthesized

<400> SEQUENCE: 147
uauccagcug agcuacggau gc                                              22

<210> SEQ ID NO 148
<211> LENGTH: 22
<212> TYPE: RNA
<213> ORGANISM: Artificial Sequence
<220> FEATURE:
<223> OTHER INFORMATION: Artificially synthesized

<400> SEQUENCE: 148
uggugcaucc gggaggauuc ga                                              22

<210> SEQ ID NO 149
<211> LENGTH: 22
<212> TYPE: RNA
<213> ORGANISM: Artificial Sequence
<220> FEATURE:
<223> OTHER INFORMATION: Artificially synthesized

<400> SEQUENCE: 149
auauccauuu aacuaagagg ac                                              22

<210> SEQ ID NO 150
<211> LENGTH: 22
<212> TYPE: RNA
<213> ORGANISM: Artificial Sequence
<220> FEATURE:
<223> OTHER INFORMATION: Artificially synthesized

<400> SEQUENCE: 150 ugguguccccc ugcaggaauc ga                                             22

<210> SEQ ID NO 151
<211> LENGTH: 22
<212> TYPE: RNA
<213> ORGANISM: Artificial Sequence
<220> FEATURE:
<223> OTHER INFORMATION: Artificially synthesized

<400> SEQUENCE: 151
uauccaacug agcuaagggc gc                                              22
```

<210> SEQ ID NO 152
<211> LENGTH: 22
<212> TYPE: RNA
<213> ORGANISM: Artificial Sequence
<220> FEATURE:
<223> OTHER INFORMATION: Artificially synthesized

<400> SEQUENCE: 152
uggcgcgccc ugcaggauuc ga                                              22

<210> SEQ ID NO 153
<211> LENGTH: 22
<212> TYPE: RNA
<213> ORGANISM: Artificial Sequence
<220> FEATURE:
<223> OTHER INFORMATION: Artificially synthesized

<400> SEQUENCE: 153
cuuaccgcuu ggcgauaccc ca                                              22

<210> SEQ ID NO 154
<211> LENGTH: 22
<212> TYPE: RNA
<213> ORGANISM: Artificial Sequence
<220> FEATURE:
<223> OTHER INFORMATION: Artificially synthesized

<400> SEQUENCE: 154
uggcuggggu acgaggauuc ga                                              22

<210> SEQ ID NO 155
<211> LENGTH: 22
<212> TYPE: RNA
<213> ORGANISM: Artificial Sequence
<220> FEATURE:
<223> OTHER INFORMATION: Artificially synthesized

<400> SEQUENCE: 155
cuuaccgcuu ggcgauaccc ca                                              22

<210> SEQ ID NO 156
<211> LENGTH: 22
<212> TYPE: RNA
<213> ORGANISM: Artificial Sequence
<220> FEATURE:
<223> OTHER INFORMATION: Artificially synthesized

<400> SEQUENCE: 156
uggcuggggu accuggauuc ga                                              22

<210> SEQ ID NO 157
<211> LENGTH: 22
<212> TYPE: RNA
<213> ORGANISM: Artificial Sequence
<220> FEATURE:
<223> OTHER INFORMATION: Artificially synthesized

<400> SEQUENCE: 157
uaaccaccug agcuacaagc cu                                              22

<210> SEQ ID NO 158
<211> LENGTH: 22
<212> TYPE: RNA
<213> ORGANISM: Artificial Sequence
<220> FEATURE:

<223> OTHER INFORMATION: Artificially synthesized

<400> SEQUENCE: 158
ugguaggccu gaguggacuu ga                                                22

<210> SEQ ID NO 159
<211> LENGTH: 22
<212> TYPE: RNA
<213> ORGANISM: Artificial Sequence
<220> FEATURE:
<223> OTHER INFORMATION: Artificially synthesized

<400> SEQUENCE: 159
uaaccaccug agcuacaagc cu                                                22

<210> SEQ ID NO 160
<211> LENGTH: 22
<212> TYPE: RNA
<213> ORGANISM: Artificial Sequence
<220> FEATURE:
<223> OTHER INFORMATION: Artificially synthesized

<400> SEQUENCE: 160
ugguaggccu gaguggacuu ga                                                22

<210> SEQ ID NO 161
<211> LENGTH: 22
<212> TYPE: RNA
<213> ORGANISM: Artificial Sequence
<220> FEATURE:
<223> OTHER INFORMATION: Artificially synthesized

<400> SEQUENCE: 161
cuaaccacug agcuaagggg cc                                                22

<210> SEQ ID NO 162
<211> LENGTH: 22
<212> TYPE: RNA
<213> ORGANISM: Artificial Sequence
<220> FEATURE:
<223> OTHER INFORMATION: Artificially synthesized

<400> SEQUENCE: 162
uggugccccc ugcuggacuu ga                                                22

<210> SEQ ID NO 163
<211> LENGTH: 22
<212> TYPE: RNA
<213> ORGANISM: Artificial Sequence
<220> FEATURE:
<223> OTHER INFORMATION: Artificially synthesized

<400> SEQUENCE: 163
cuaccaacug agcuauauca gc                                                22

<210> SEQ ID NO 164
<211> LENGTH: 22
<212> TYPE: RNA
<213> ORGANISM: Artificial Sequence
<220> FEATURE:
<223> OTHER INFORMATION: Artificially synthesized

<400> SEQUENCE: 164
uggugcugau aggcagauuc ga                                                22

```
<210> SEQ ID NO 165
<211> LENGTH: 22
<212> TYPE: RNA
<213> ORGANISM: Artificial Sequence
<220> FEATURE:
<223> OTHER INFORMATION: Artificially synthesized

<400> SEQUENCE: 165
cuaccaacug agccauauca gc                                              22

<210> SEQ ID NO 166
<211> LENGTH: 22
<212> TYPE: RNA
<213> ORGANISM: Artificial Sequence
<220> FEATURE:
<223> OTHER INFORMATION: Artificially synthesized

<400> SEQUENCE: 166
uggugcugau acccagaguc ga                                              22

<210> SEQ ID NO 167
<211> LENGTH: 22
<212> TYPE: RNA
<213> ORGANISM: Artificial Sequence
<220> FEATURE:
<223> OTHER INFORMATION: Artificially synthesized

<400> SEQUENCE: 167
ugggccucua gacgaagggg ac                                              22

<210> SEQ ID NO 168
<211> LENGTH: 22
<212> TYPE: RNA
<213> ORGANISM: Artificial Sequence
<220> FEATURE:
<223> OTHER INFORMATION: Artificially synthesized

<400> SEQUENCE: 168 uggcguccccc caggggauuc ga                                             22

<210> SEQ ID NO 169
<211> LENGTH: 22
<212> TYPE: RNA
<213> ORGANISM: Artificial Sequence
<220> FEATURE:
<223> OTHER INFORMATION: Artificially synthesized

<400> SEQUENCE: 169
ugggccucua gacgaagggg ac                                              22

<210> SEQ ID NO 170
<211> LENGTH: 22
<212> TYPE: RNA
<213> ORGANISM: Artificial Sequence
<220> FEATURE:
<223> OTHER INFORMATION: Artificially synthesized

<400> SEQUENCE: 170 uggcguccccc uaggggauuc ga                                             22

<210> SEQ ID NO 171
<211> LENGTH: 22
<212> TYPE: RNA
<213> ORGANISM: Artificial Sequence
<220> FEATURE:
<223> OTHER INFORMATION: Artificially synthesized
```

```
<400> SEQUENCE: 171
cuggccucua gacgaaggg ac                                             22

<210> SEQ ID NO 172
<211> LENGTH: 22
<212> TYPE: RNA
<213> ORGANISM: Artificial Sequence
<220> FEATURE:
<223> OTHER INFORMATION: Artificially synthesized

<400> SEQUENCE: 172 uggcguccc uagggauuc ga                                              22

<210> SEQ ID NO 173
<211> LENGTH: 22
<212> TYPE: RNA
<213> ORGANISM: Artificial Sequence
<220> FEATURE:
<223> OTHER INFORMATION: Artificially synthesized

<400> SEQUENCE: 173
uaccaggcug cuccaccccg cg                                            22

<210> SEQ ID NO 174
<211> LENGTH: 22
<212> TYPE: RNA
<213> ORGANISM: Artificial Sequence
<220> FEATURE:
<223> OTHER INFORMATION: Artificially synthesized

<400> SEQUENCE: 174
ugguugcggg ggccggauuu ga                                            22

<210> SEQ ID NO 175
<211> LENGTH: 22
<212> TYPE: RNA
<213> ORGANISM: Artificial Sequence
<220> FEATURE:
<223> OTHER INFORMATION: Artificially synthesized

<400> SEQUENCE: 175
uaccaggcug cuccaccccg cg                                            22

<210> SEQ ID NO 176
<211> LENGTH: 22
<212> TYPE: RNA
<213> ORGANISM: Artificial Sequence
<220> FEATURE:
<223> OTHER INFORMATION: Artificially synthesized

<400> SEQUENCE: 176
ugguugcggg ggccggauuu ga                                            22

<210> SEQ ID NO 177
<211> LENGTH: 22
<212> TYPE: RNA
<213> ORGANISM: Artificial Sequence
<220> FEATURE:
<223> OTHER INFORMATION: Artificially synthesized

<400> SEQUENCE: 177
ucuaccauug aacuacgccc gc                                            22

<210> SEQ ID NO 178
<211> LENGTH: 22
```

```
<212> TYPE: RNA
<213> ORGANISM: Artificial Sequence
<220> FEATURE:
<223> OTHER INFORMATION: Artificially synthesized

<400> SEQUENCE: 178
uggagcgggc gaagggaauc ga                                         22

<210> SEQ ID NO 179
<211> LENGTH: 22
<212> TYPE: RNA
<213> ORGANISM: Artificial Sequence
<220> FEATURE:
<223> OTHER INFORMATION: Artificially synthesized

<400> SEQUENCE: 179
cuaccaacug agcuauuccc gc                                         22

<210> SEQ ID NO 180
<211> LENGTH: 22
<212> TYPE: RNA
<213> ORGANISM: Artificial Sequence
<220> FEATURE:
<223> OTHER INFORMATION: Artificially synthesized

<400> SEQUENCE: 180
uggagcggga aacgagacuc ga                                         22

<210> SEQ ID NO 181
<211> LENGTH: 22
<212> TYPE: RNA
<213> ORGANISM: Artificial Sequence
<220> FEATURE:
<223> OTHER INFORMATION: Artificially synthesized

<400> SEQUENCE: 181
auagccauua uacgaugccc gc                                         22

<210> SEQ ID NO 182
<211> LENGTH: 22
<212> TYPE: RNA
<213> ORGANISM: Artificial Sequence
<220> FEATURE:
<223> OTHER INFORMATION: Artificially synthesized

<400> SEQUENCE: 182
uggagcgggc agcgggaauc ga                                         22

<210> SEQ ID NO 183
<211> LENGTH: 22
<212> TYPE: RNA
<213> ORGANISM: Artificial Sequence
<220> FEATURE:
<223> OTHER INFORMATION: Artificially synthesized

<400> SEQUENCE: 183
cuaccgauuu cgccacuucg gc                                         22

<210> SEQ ID NO 184
<211> LENGTH: 22
<212> TYPE: RNA
<213> ORGANISM: Artificial Sequence
<220> FEATURE:
<223> OTHER INFORMATION: Artificially synthesized

<400> SEQUENCE: 184
```
uggugccgaa ggccggacuc ga                                      22

<210> SEQ ID NO 185
<211> LENGTH: 22
<212> TYPE: RNA
<213> ORGANISM: Artificial Sequence
<220> FEATURE:
<223> OTHER INFORMATION: Artificially synthesized

<400> SEQUENCE: 185
cuaccaauuc cgccaccuuc gc                                      22

<210> SEQ ID NO 186
<211> LENGTH: 22
<212> TYPE: RNA
<213> ORGANISM: Artificial Sequence
<220> FEATURE:
<223> OTHER INFORMATION: Artificially synthesized

<400> SEQUENCE: 186
uggugcgagg gggggacuu ga                                       22

<210> SEQ ID NO 187
<211> LENGTH: 22
<212> TYPE: RNA
<213> ORGANISM: Artificial Sequence
<220> FEATURE:
<223> OTHER INFORMATION: Artificially synthesized

<400> SEQUENCE: 187
cucccaauuc caccaccucg gc                                      22

<210> SEQ ID NO 188
<211> LENGTH: 22
<212> TYPE: RNA
<213> ORGANISM: Artificial Sequence
<220> FEATURE:
<223> OTHER INFORMATION: Artificially synthesized

<400> SEQUENCE: 188
ugguaccgag gacgggacuu ga                                      22

<210> SEQ ID NO 189
<211> LENGTH: 22
<212> TYPE: RNA
<213> ORGANISM: Artificial Sequence
<220> FEATURE:
<223> OTHER INFORMATION: Artificially synthesized

<400> SEQUENCE: 189
cuaccgauuc caccauccgg gc                                      22

<210> SEQ ID NO 190
<211> LENGTH: 22
<212> TYPE: RNA
<213> ORGANISM: Artificial Sequence
<220> FEATURE:
<223> OTHER INFORMATION: Artificially synthesized

<400> SEQUENCE: 190
ugguacccgg agcgggacuu ga                                      22

<210> SEQ ID NO 191
<211> LENGTH: 22
<212> TYPE: RNA
<213> ORGANISM: Artificial Sequence

```
<220> FEATURE:
<223> OTHER INFORMATION: Artificially synthesized

<400> SEQUENCE: 191
uuggccgcuc gggaacccca cc                                              22

<210> SEQ ID NO 192
<211> LENGTH: 22
<212> TYPE: RNA
<213> ORGANISM: Artificial Sequence
<220> FEATURE:
<223> OTHER INFORMATION: Artificially synthesized

<400> SEQUENCE: 192
uggugguggg ggaaggauuc ga                                              22

<210> SEQ ID NO 193
<211> LENGTH: 22
<212> TYPE: RNA
<213> ORGANISM: Artificial Sequence
<220> FEATURE:
<223> OTHER INFORMATION: Artificially synthesized

<400> SEQUENCE: 193
uuggccgcuc gggaacccca cc                                              22

<210> SEQ ID NO 194
<211> LENGTH: 22
<212> TYPE: RNA
<213> ORGANISM: Artificial Sequence
<220> FEATURE:
<223> OTHER INFORMATION: Artificially synthesized

<400> SEQUENCE: 194
uggugguggg ggaaggauuc ga                                              22

<210> SEQ ID NO 195
<211> LENGTH: 76
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (17)..(17)
<223> OTHER INFORMATION: n=d
<220> FEATURE:
<221> NAME/KEY: modified_base
<222> LOCATION: (34)..(34)
<223> OTHER INFORMATION: u=cmo5u
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (55)..(55)
```

```
<223> OTHER INFORMATION: n is a, c, g, t or u

<400> SEQUENCE: 195
gggggcauag cucagcnggg agagcgccug cuuugcacgc aggaggucug cgguncgauc      60
ccgcgcgcuc ccacca                                                     76

<210> SEQ ID NO 196
<211> LENGTH: 76
<212> TYPE: RNA
<213> ORGANISM: Escherichia coli
<220> FEATURE:
<221> NAME/KEY: modified_base
<222> LOCATION: (17)..(17)
<223> OTHER INFORMATION: n=d
<220> FEATURE:
<221> NAME/KEY: modified_base
<222> LOCATION: (34)..(34)
<223> OTHER INFORMATION: u=cmo5u
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 196
ggggcuauag cucagcnggg agagcgccug cuuugcacgc aggaggucug cgguncgauc      60
ccgcauagcu ccacca                                                     76

<210> SEQ ID NO 197
<211> LENGTH: 76
<212> TYPE: RNA
<213> ORGANISM: Escherichia coli
<220> FEATURE:
<221> NAME/KEY: modified_base
<222> LOCATION: (17)..(17)
<223> OTHER INFORMATION: n=d
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
```

<222> LOCATION: (55)..(55)
<223> OTHER INFORMATION: n is a, c, g, t or u

<400> SEQUENCE: 197
ggggcuanag cucagcnggg agagcgcuug cauggcaugc aagaggucag cgguncgauc    60
ccgcuuagcu ccacca                                                   76

<210> SEQ ID NO 198
<211> LENGTH: 77
<212> TYPE: RNA
<213> ORGANISM: Escherichia coli
<220> FEATURE:
<221> NAME/KEY: modified_base
<222> LOCATION: (17)..(17)
<223> OTHER INFORMATION: n=d
<220> FEATURE:
<221> NAME/KEY: modified_base
<222> LOCATION: (21)..(21)
<223> OTHER INFORMATION: n=d
<220> FEATURE:
<221> NAME/KEY: modified_base
<222> LOCATION: (33)..(33)
<223> OTHER INFORMATION: c=s2c
<220> FEATURE:
<221> NAME/KEY: modified_base
<222> LOCATION: (38)..(38)
<223> OTHER INFORMATION: g=m1g
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 198
gcgcccguag cucagcngga nagagcgcug cccuccggag gcagaggucu cagguncgaa    60
uccugucggg cgcgcca                                                  77

<210> SEQ ID NO 199
<211> LENGTH: 76
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (17)..(17)
<223> OTHER INFORMATION: n=d
<220> FEATURE:
<221> NAME/KEY: modified_base
<222> LOCATION: (20)..(20)
<223> OTHER INFORMATION: n=d
<220> FEATURE:

```
<221> NAME/KEY: modified_base
<222> LOCATION: (32)..(32)
<223> OTHER INFORMATION: c=s2c
<220> FEATURE:
<221> NAME/KEY: modified_base
<222> LOCATION: (34)..(34)
<223> OTHER INFORMATION: n=i
<220> FEATURE:
<221> NAME/KEY: modified_base
<222> LOCATION: (37)..(37)
<223> OTHER INFORMATION: a=m2a
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (47)..(47)
<223> OTHER INFORMATION: u=acp3u
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (34)..(34)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 199
gcauccguag cucagcnggn agaguacucg gcuncgaacc gagcggucgg agguncgaau    60
ccucccggau gcacca                                                   76

<210> SEQ ID NO 200
<211> LENGTH: 77
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (17)..(17)
<223> OTHER INFORMATION: n=d
<220> FEATURE:
<221> NAME/KEY: modified_base
<222> LOCATION: (21)..(21)
<223> OTHER INFORMATION: n=d
<220> FEATURE:
<221> NAME/KEY: modified_base
<222> LOCATION: (35)..(35)
<223> OTHER INFORMATION: n=i
<220> FEATURE:
<221> NAME/KEY: modified_base
<222> LOCATION: (38)..(38)
<223> OTHER INFORMATION: a=m2a
<220> FEATURE:
<221> NAME/KEY: modified_base
<222> LOCATION: (47)..(47)
<223> OTHER INFORMATION: g=m7g
```

```
<220> FEATURE:
<221> NAME/KEY: modified_base
<222> LOCATION: (48)..(48)
<223> OTHER INFORMATION: u=acp3u
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (35)..(35)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 200
gcauccguag ucagcngga nagaguacuc ggcuncgaac cgagcggucg gagguncgaa      60
uccucccgga ugcacca                                                    77

<210> SEQ ID NO 201
<211> LENGTH: 75
<212> TYPE: RNA
<213> ORGANISM: Escherichia coli
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (32)..(32)
<223> OTHER INFORMATION: c=s2c
<220> FEATURE:
<221> NAME/KEY: modified_base
<222> LOCATION: (37)..(37)
<223> OTHER INFORMATION: a=t6a
<220> FEATURE:
<221> NAME/KEY: modified_base
<222> LOCATION: (53)..(53)
<223> OTHER INFORMATION: u=m5u
<220> FEATURE:
<221> NAME/KEY: modified_base
<222> LOCATION: (54)..(54)
<223> OTHER INFORMATION: n=p
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u

<400> SEQUENCE: 201
guccucuuag uuaaauggan auaacgagcc ccuucuaagg gcuaauugca gguncgauuc      60
cugcagggga cacca                                                      75

<210> SEQ ID NO 202
<211> LENGTH: 77
<212> TYPE: RNA
```

```
<213> ORGANISM: Escherichia coli
<220> FEATURE:
<221> NAME/KEY: modified_base
<222> LOCATION: (33)..(33)
<223> OTHER INFORMATION: c=s2c
<220> FEATURE:
<221> NAME/KEY: modified_base
<222> LOCATION: (35)..(35)
<223> OTHER INFORMATION: u=mnm5u
<220> FEATURE:
<221> NAME/KEY: modified_base
<222> LOCATION: (38)..(38)
<223> OTHER INFORMATION: a=t6a
<220> FEATURE:
<221> NAME/KEY: modified_base
<222> LOCATION: (41)..(41)
<223> OTHER INFORMATION: n=p
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 202
gcgcccuuag cucaguugga uagagcaacg accuucuaag ncgugggccg cagguncgaa      60
uccugcaggg cgcgcca                                                    77

<210> SEQ ID NO 203
<211> LENGTH: 76
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(16)
<223> OTHER INFORMATION: n=d
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (34)..(34)
<223> OTHER INFORMATION: n=q
<220> FEATURE:
<221> NAME/KEY: modified_base
<222> LOCATION: (37)..(37)
<223> OTHER INFORMATION: a=t6a
<220> FEATURE:
<221> NAME/KEY: modified_base
<222> LOCATION: (39)..(39)
<223> OTHER INFORMATION: n=p
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
```

```
<222> LOCATION: (55)..(55)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (34)..(34)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 203
uccucuguag uucagncggn agaacggcgg acunuuaanc cguaugucac ugguncgagu      60
ccagucagag gagcca                                                     76

<210> SEQ ID NO 204
<211> LENGTH: 77
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(16)
<223> OTHER INFORMATION: n=d
<220> FEATURE:
<221> NAME/KEY: modified_base
<222> LOCATION: (20)..(21)
<223> OTHER INFORMATION: n=d
<220> FEATURE:
<221> NAME/KEY: modified_base
<222> LOCATION: (35)..(35)
<223> OTHER INFORMATION: n=gluq
<220> FEATURE:
<221> NAME/KEY: modified_base
<222> LOCATION: (38)..(38)
<223> OTHER INFORMATION: a=m2a
<220> FEATURE:
<221> NAME/KEY: modified_base
<222> LOCATION: (47)..(47)
<223> OTHER INFORMATION: g=m7g
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: modified_base
<222> LOCATION: (66)..(66)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
```

```
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (35)..(35)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u

<400> SEQUENCE: 204
ggagcgguag uucagncggn nagaauaccu gccunucacg caggggucg cggguncgag    60 ucccgnccgu uccgcca                                                  77

<210> SEQ ID NO 205
<211> LENGTH: 74
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (19)..(20)
<223> OTHER INFORMATION: n=d
<220> FEATURE:
<221> NAME/KEY: modified_base
<222> LOCATION: (31)..(31)
<223> OTHER INFORMATION: n=p
<220> FEATURE:
<221> NAME/KEY: modified_base
<222> LOCATION: (36)..(36)
<223> OTHER INFORMATION: a=ms2i6a
<220> FEATURE:
<221> NAME/KEY: modified_base
<222> LOCATION: (38)..(38)
<223> OTHER INFORMATION: n=p
<220> FEATURE:
<221> NAME/KEY: modified_base
<222> LOCATION: (52)..(52)
<223> OTHER INFORMATION: u=m5u
<220> FEATURE:
<221> NAME/KEY: modified_base
<222> LOCATION: (53)..(53)
<223> OTHER INFORMATION: n=p
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (53)..(53)
<223> OTHER INFORMATION: n is a, c, g, t or u

<400> SEQUENCE: 205
ggcgcguuaa caaagcggnn auguagcgga nugcaaancc gucuaguccg guncgacucc    60
```
ggaacgcgcc ucca                                                         74

<210> SEQ ID NO 206
<211> LENGTH: 75
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (17)..(17)
<223> OTHER INFORMATION: g=gm
<220> FEATURE:
<221> NAME/KEY: modified_base
<222> LOCATION: (19)..(19)
<223> OTHER INFORMATION: n=d
<220> FEATURE:
<221> NAME/KEY: modified_base
<222> LOCATION: (31)..(31)
<223> OTHER INFORMATION: u=um
<220> FEATURE:
<221> NAME/KEY: modified_base
<222> LOCATION: (33)..(33)
<223> OTHER INFORMATION: u=cmnm5s2u
<220> FEATURE:
<221> NAME/KEY: modified_base
<222> LOCATION: (36)..(36)
<223> OTHER INFORMATION: a=m2a
<220> FEATURE:
<221> NAME/KEY: modified_base
<222> LOCATION: (37)..(37)
<223> OTHER INFORMATION: n=p
<220> FEATURE:
<221> NAME/KEY: modified_base
<222> LOCATION: (53)..(53)
<223> OTHER INFORMATION: u=m5u
<220> FEATURE:
<221> NAME/KEY: modified_base
<222> LOCATION: (54)..(54)
<223> OTHER INFORMATION: n=p
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (37)..(37)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u

<400> SEQUENCE: 206
ugggguaucg ccaagcggna aggcaccggu uuuuganacc ggcauucccu gguncgaauc       60
cagguacccc agcca                                                        75

<210> SEQ ID NO 207
<211> LENGTH: 75
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (17)..(17)
<223> OTHER INFORMATION: g=gm
<220> FEATURE:
<221> NAME/KEY: modified_base
<222> LOCATION: (19)..(19)

<223> OTHER INFORMATION: n=d
<220> FEATURE:
<221> NAME/KEY: modified_base
<222> LOCATION: (31)..(31)
<223> OTHER INFORMATION: u=um
<220> FEATURE:
<221> NAME/KEY: modified_base
<222> LOCATION: (36)..(36)
<223> OTHER INFORMATION: a=m2a
<220> FEATURE:
<221> NAME/KEY: modified_base
<222> LOCATION: (37)..(38)
<223> OTHER INFORMATION: n=p
<220> FEATURE:
<221> NAME/KEY: modified_base
<222> LOCATION: (53)..(53)
<223> OTHER INFORMATION: u=m5u
<220> FEATURE:
<221> NAME/KEY: modified_base
<222> LOCATION: (54)..(54)
<223> OTHER INFORMATION: n=p
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (37)..(37)
<223> OTHER INFORMATION: n is a, c, g, t or u
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u

<400> SEQUENCE: 207 uggggu aucg ccaagcggna aggcaccgga uucuganncc ggcauuccga gguncgaauc    60
cucguacccc agcca                                                     75

<210> SEQ ID NO 208
<211> LENGTH: 76
<212> TYPE: RNA
<213> ORGANISM: Escherichia coli
<220> FEATURE:
<221> NAME/KEY: modified_base
<222> LOCATION: (13)..(13)
<223> OTHER INFORMATION: n=p
<220> FEATURE:
<221> NAME/KEY: modified_base
<222> LOCATION: (35)..(35)
<223> OTHER INFORMATION: u=mnm5s2u
<220> FEATURE:
<221> NAME/KEY: modified_base
<222> LOCATION: (38)..(38)
<223> OTHER INFORMATION: a=m2a
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 208 gucccccuucg ucnagaggcc caggacaccg cccuuucacg gcgguaacag ggguncgaau    60
ccccuggggg acgcca    76

<210> SEQ ID NO 209
<211> LENGTH: 76
<212> TYPE: RNA
<213> ORGANISM: Escherichia coli
<220> FEATURE:
<221> NAME/KEY: modified_base
<222> LOCATION: (13)..(13)
<223> OTHER INFORMATION: n=p
<220> FEATURE:
<221> NAME/KEY: modified_base
<222> LOCATION: (35)..(35)
<223> OTHER INFORMATION: u=mnm5s2u
<220> FEATURE:
<221> NAME/KEY: modified_base
<222> LOCATION: (38)..(38)
<223> OTHER INFORMATION: a=m2a
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 209 gucccccuucg ucnagaggcc caggacaccg cccuuucacg gcgguaacag ggguncgaau    60 ccccuaggggg acgcca    76

<210> SEQ ID NO 210
<211> LENGTH: 75
<212> TYPE: RNA
<213> ORGANISM: Escherichia coli
<220> FEATURE:
<221> NAME/KEY: modified_base
<222> LOCATION: (13)..(13)
<223> OTHER INFORMATION: n=p
<220> FEATURE:
<221> NAME/KEY: modified_base
<222> LOCATION: (34)..(34)
<223> OTHER INFORMATION: u=mnm5s2u
<220> FEATURE:
<221> NAME/KEY: modified_base
<222> LOCATION: (37)..(37)
<223> OTHER INFORMATION: a=m2a
<220> FEATURE:
<221> NAME/KEY: modified_base
<222> LOCATION: (53)..(53)
<223> OTHER INFORMATION: u=m5u
<220> FEATURE:
<221> NAME/KEY: modified_base
<222> LOCATION: (54)..(54)
<223> OTHER INFORMATION: n=p
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u

```
<400> SEQUENCE: 210 gucccccuucg ucnagaggcc aggacaccgc ccuuucacgg cgguaacagg gguncgaauc    60
cccuagggga cgcca                                                     75

<210> SEQ ID NO 211
<211> LENGTH: 74
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (19)..(19)
<223> OTHER INFORMATION: n=d
<220> FEATURE:
<221> NAME/KEY: modified_base
<222> LOCATION: (52)..(52)
<223> OTHER INFORMATION: u=m5u
<220> FEATURE:
<221> NAME/KEY: modified_base
<222> LOCATION: (53)..(53)
<223> OTHER INFORMATION: n=p
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (53)..(53)
<223> OTHER INFORMATION: n is a, c, g, t or u

<400> SEQUENCE: 211
gcgggcguag uucaauggna gaacgagagc uucccaagcu cuauacgagg guncgauucc    60
cuucgcccgc ucca                                                      74

<210> SEQ ID NO 212
<211> LENGTH: 75
<212> TYPE: RNA
<213> ORGANISM: Escherichia coli
<220> FEATURE:
<221> NAME/KEY: modified_base
<222> LOCATION: (34)..(34)
<223> OTHER INFORMATION: u=mnm5u
<220> FEATURE:
<221> NAME/KEY: modified_base
<222> LOCATION: (53)..(53)
<223> OTHER INFORMATION: u=m5u
<220> FEATURE:
<221> NAME/KEY: modified_base
<222> LOCATION: (54)..(54)
<223> OTHER INFORMATION: n=p
<220> FEATURE:
<221> NAME/KEY: misc_feature
<222> LOCATION: (54)..(54)
<223> OTHER INFORMATION: n is a, c, g, t or u

<400> SEQUENCE: 212
gcgggcaucg uauaauggcu auuaccucag ccuuccaagc ugaugaugcg gguncgauuc    60
ccgcugcccg cucca                                                     75

<210> SEQ ID NO 213
<211> LENGTH: 76
<212> TYPE: RNA
<213> ORGANISM: Escherichia coli
<220> FEATURE:
<221> NAME/KEY: modified_base
<222> LOCATION: (16)..(17)
<223> OTHER INFORMATION: n=d
```

-continued

```
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 213
gcgggaauag cucagnnggn agagcacgac cuugccaagg ucgggucgc gaguncgagu    60 cucguuuccc gcucca                                                  76

<210> SEQ ID NO 214
<211> LENGTH: 77
<212> TYPE: RNA
<213> ORGANISM: Escherichia coli
<220> FEATURE:
<221> NAME/KEY: modified_base
<222> LOCATION: (9)..(9)
<223> OTHER INFORMATION: u=s4u
<220> FEATURE:
<221> NAME/KEY: modified_base
<222> LOCATION: (17)..(18)
<223> OTHER INFORMATION: n=d
<220> FEATURE:
<221> NAME/KEY: modified_base
<222> LOCATION: (21)..(21)
<223> OTHER INFORMATION: n=d
<220> FEATURE:
<221> NAME/KEY: modified_base
<222> LOCATION: (35)..(35)
<223> OTHER INFORMATION: n=q
<220> FEATURE:
<221> NAME/KEY: modified_base
<222> LOCATION: (38)..(38)
<223> OTHER INFORMATION: a=m2a
<220> FEATURE:
<221> NAME/KEY: modified_base
<222> LOCATION: (39)..(40)
<223> OTHER INFORMATION: n=p
<220> FEATURE:
<221> NAME/KEY: modified_base
<222> LOCATION: (47)..(47)
<223> OTHER INFORMATION: g=m7g
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
```

```
<223> OTHER INFORMATION: n=p
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (35)..(35)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 214
gguggcuaua gcucagnngg nagagcccug gauunugann ccaguugucg ugggucgaa      60 ucccauuagc cacccca                                                   77

<210> SEQ ID NO 215
<211> LENGTH: 77
<212> TYPE: RNA
<213> ORGANISM: Escherichia coli
<220> FEATURE:
<221> NAME/KEY: modified_base
<222> LOCATION: (17)..(17)
<223> OTHER INFORMATION: n=d
<220> FEATURE:
<221> NAME/KEY: modified_base
<222> LOCATION: (20)..(21)
<223> OTHER INFORMATION: n=d
<220> FEATURE:
<221> NAME/KEY: modified_base
<222> LOCATION: (38)..(38)
<223> OTHER INFORMATION: a=t6a
<220> FEATURE:
<221> NAME/KEY: modified_base
<222> LOCATION: (47)..(47)
<223> OTHER INFORMATION: g=m7g
<220> FEATURE:
<221> NAME/KEY: modified_base
<222> LOCATION: (48)..(48)
<223> OTHER INFORMATION: u=acp3u
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: modified_base
<222> LOCATION: (66)..(66)
<223> OTHER INFORMATION: n=p
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
```

```
<222> LOCATION: (20)..(20)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u

<400> SEQUENCE: 215
aggcuuguag cucaggnggn nagagcgcac cccugauaag ggugaggucg gugguncaag    60
uccacncagg ccuacca                                                  77

<210> SEQ ID NO 216
<211> LENGTH: 77
<212> TYPE: RNA
<213> ORGANISM: Escherichia coli
<220> FEATURE:
<221> NAME/KEY: modified_base
<222> LOCATION: (20)..(21)
<223> OTHER INFORMATION: n=d
<220> FEATURE:
<221> NAME/KEY: modified_base
<222> LOCATION: (47)..(47)
<223> OTHER INFORMATION: g=m7g
<220> FEATURE:
<221> NAME/KEY: modified_base
<222> LOCATION: (48)..(48)
<223> OTHER INFORMATION: u=acp3u
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: modified_base
<222> LOCATION: (66)..(66)
<223> OTHER INFORMATION: n=p
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u

<400> SEQUENCE: 216
aggcuuguag cucagguggn nagagcgcac cccugauaag ggugaggucg gugguncaag    60
uccacncagg ccuacca                                                  77

<210> SEQ ID NO 217
<211> LENGTH: 76
<212> TYPE: RNA
<213> ORGANISM: Escherichia coli
<220> FEATURE:
```

```
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (17)..(17)
<223> OTHER INFORMATION: g=gm
<220> FEATURE:
<221> NAME/KEY: modified_base
<222> LOCATION: (19)..(20)
<223> OTHER INFORMATION: n=d
<220> FEATURE:
<221> NAME/KEY: modified_base
<222> LOCATION: (34)..(34)
<223> OTHER INFORMATION: c=k2c
<220> FEATURE:
<221> NAME/KEY: modified_base
<222> LOCATION: (37)..(37)
<223> OTHER INFORMATION: a=t6a
<220> FEATURE:
<221> NAME/KEY: modified_base
<222> LOCATION: (39)..(39)
<223> OTHER INFORMATION: n=p
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (47)..(47)
<223> OTHER INFORMATION: u=acp3u
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 217
ggccccuuag cucaguggnn agagcaggcg acucauaanc gcuuggucgc ugguncaagu    60
ccagcagggg ccacca                                                   76

<210> SEQ ID NO 218
<211> LENGTH: 87
<212> TYPE: RNA
<213> ORGANISM: Escherichia coli
<220> FEATURE:
<221> NAME/KEY: modified_base
<222> LOCATION: (16)..(17)
<223> OTHER INFORMATION: n=d
<220> FEATURE:
<221> NAME/KEY: modified_base
<222> LOCATION: (18)..(18)
<223> OTHER INFORMATION: g=gm
<220> FEATURE:
<221> NAME/KEY: modified_base
<222> LOCATION: (20)..(20)
<223> OTHER INFORMATION: n=d
```

```
<220> FEATURE:
<221> NAME/KEY: modified_base
<222> LOCATION: (38)..(38)
<223> OTHER INFORMATION: g=m1g
<220> FEATURE:
<221> NAME/KEY: modified_base
<222> LOCATION: (39)..(39)
<223> OTHER INFORMATION: n=p
<220> FEATURE:
<221> NAME/KEY: modified_base
<222> LOCATION: (41)..(41)
<223> OTHER INFORMATION: n=p
<220> FEATURE:
<221> NAME/KEY: modified_base
<222> LOCATION: (65)..(65)
<223> OTHER INFORMATION: u=m5u
<220> FEATURE:
<221> NAME/KEY: modified_base
<222> LOCATION: (66)..(66)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u

<400> SEQUENCE: 218
gcgaaggugg cggaannggn agacgcgcua gcuucaggng nuaguguccu uacggacgug      60
gggguncaag uccccccccu cgcacca                                         87

<210> SEQ ID NO 219
<211> LENGTH: 87
<212> TYPE: RNA
<213> ORGANISM: Escherichia coli
<220> FEATURE:
<221> NAME/KEY: modified_base
<222> LOCATION: (16)..(17)
<223> OTHER INFORMATION: n=d
<220> FEATURE:
<221> NAME/KEY: modified_base
<222> LOCATION: (18)..(18)
<223> OTHER INFORMATION: g=gm
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (38)..(38)
<223> OTHER INFORMATION: g=m1g
<220> FEATURE:
<221> NAME/KEY: modified_base
<222> LOCATION: (39)..(39)
<223> OTHER INFORMATION: n=p
<220> FEATURE:
<221> NAME/KEY: modified_base
<222> LOCATION: (65)..(65)
```

```
<223> OTHER INFORMATION: u=m5u
<220> FEATURE:
<221> NAME/KEY: modified_base
<222> LOCATION: (66)..(66)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u

<400> SEQUENCE: 219
gccgaggugg uggaannggn agacacgcua ccuugaggng guagugccca auagggcuua    60
cggguncaag ucccguccuc gguacca                                       87

<210> SEQ ID NO 220
<211> LENGTH: 87
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(16)
<223> OTHER INFORMATION: n=d
<220> FEATURE:
<221> NAME/KEY: modified_base
<222> LOCATION: (18)..(18)
<223> OTHER INFORMATION: g=gm
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (33)..(33)
<223> OTHER INFORMATION: n=p
<220> FEATURE:
<221> NAME/KEY: modified_base
<222> LOCATION: (40)..(40)
<223> OTHER INFORMATION: n=p
<220> FEATURE:
<221> NAME/KEY: modified_base
<222> LOCATION: (65)..(65)
<223> OTHER INFORMATION: u=m5u
<220> FEATURE:
<221> NAME/KEY: modified_base
<222> LOCATION: (66)..(66)
<223> OTHER INFORMATION: n=p
<220> FEATURE:
<221> NAME/KEY: modified_base
<222> LOCATION: (35)..(35)
<223> OTHER INFORMATION: u=cmnm5um
<220> FEATURE:
<221> NAME/KEY: modified_base
<222> LOCATION: (38)..(38)
<223> OTHER INFORMATION: a=ms2i6a
<220> FEATURE:
<221> NAME/KEY: misc_feature
```

```
<222> LOCATION: (16)..(16)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u

<400> SEQUENCE: 220
gcccggaugg uggaancggn agacacaagg ganuuaaaan cccucggcgu ucgcgcugug      60 cgguncaag ucccgcuccg gguacca                                          87

<210> SEQ ID NO 221
<211> LENGTH: 85
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(16)
<223> OTHER INFORMATION: n=d
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (18)..(18)
<223> OTHER INFORMATION: g=gm
<220> FEATURE:
<221> NAME/KEY: modified_base
<222> LOCATION: (33)..(33)
<223> OTHER INFORMATION: n=p
<220> FEATURE:
<221> NAME/KEY: modified_base
<222> LOCATION: (63)..(63)
<223> OTHER INFORMATION: u=m5u
<220> FEATURE:
<221> NAME/KEY: modified_base
<222> LOCATION: (64)..(64)
<223> OTHER INFORMATION: n=p
<220> FEATURE:
<221> NAME/KEY: modified_base
<222> LOCATION: (40)..(40)
<223> OTHER INFORMATION: n=p
<220> FEATURE:
<221> NAME/KEY: modified_base
<222> LOCATION: (35)..(35)
<223> OTHER INFORMATION: c=cm
<220> FEATURE:
<221> NAME/KEY: modified_base
<222> LOCATION: (38)..(38)
<223> OTHER INFORMATION: a=ms2i6a
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
```

-continued

```
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u

<400> SEQUENCE: 221
gccgaagugg cgaaancggn agacgcaguu ganucaaaan caaccguaga aauacgugcc    60
gguncgaguc cggccuucgg cacca                                         85

<210> SEQ ID NO 222
<211> LENGTH: 76
<212> TYPE: RNA
<213> ORGANISM: Escherichia coli
<220> FEATURE:
<221> NAME/KEY: modified_base
<222> LOCATION: (16)..(17)
<223> OTHER INFORMATION: n=d
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (44)..(44)
<223> OTHER INFORMATION: u=mnm5s2u
<220> FEATURE:
<221> NAME/KEY: modified_base
<222> LOCATION: (47)..(47)
<223> OTHER INFORMATION: a=t6a
<220> FEATURE:
<221> NAME/KEY: modified_base
<222> LOCATION: (49)..(49)
<223> OTHER INFORMATION: n=p
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (47)..(47)
<223> OTHER INFORMATION: u=acp3u
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u
```

-continued

<400> SEQUENCE: 222 ggguucguuag cucagnnggn agagcaguug acuuuuaanc aauuggucgc agguncgaau    60
ccugcacgac ccacca                                                    76

<210> SEQ ID NO 223
<211> LENGTH: 77
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(17)
<223> OTHER INFORMATION: n=d
<220> FEATURE:
<221> NAME/KEY: modified_base
<222> LOCATION: (20)..(21)
<223> OTHER INFORMATION: n=d
<220> FEATURE:
<221> NAME/KEY: modified_base
<222> LOCATION: (18)..(18)
<223> OTHER INFORMATION: g=gm
<220> FEATURE:
<221> NAME/KEY: modified_base
<222> LOCATION: (35)..(35)
<223> OTHER INFORMATION: c=ac4c
<220> FEATURE:
<221> NAME/KEY: modified_base
<222> LOCATION: (38)..(38)
<223> OTHER INFORMATION: a=t6a
<220> FEATURE:
<221> NAME/KEY: modified_base
<222> LOCATION: (40)..(40)
<223> OTHER INFORMATION: n=p
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: modified_base
<222> LOCATION: (47)..(47)
<223> OTHER INFORMATION: g=m7g
<220> FEATURE:
<221> NAME/KEY: modified_base
<222> LOCATION: (48)..(48)
<223> OTHER INFORMATION: u=acp3u
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (56)..(56)

<223> OTHER INFORMATION: n is a, c, g, t or u

<400> SEQUENCE: 223
ggcuacguag cucagnnggn nagagcacau cacucauaan gaugggguca cagguncgaa    60
ucccgucgua gccacca                                                  77

<210> SEQ ID NO 224
<211> LENGTH: 76
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(16)
<223> OTHER INFORMATION: n=d
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (32)..(32)
<223> OTHER INFORMATION: n=p
<220> FEATURE:
<221> NAME/KEY: modified_base
<222> LOCATION: (37)..(37)
<223> OTHER INFORMATION: a=ms2i6a
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (47)..(47)
<223> OTHER INFORMATION: u=acp3u
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (32)..(32)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 224
gcccggauag cucagncggn agagcagggg anugaaaanc cccguguccu ugguncgauu    60
ccgaguccgg gcacca                                                   76

<210> SEQ ID NO 225
<211> LENGTH: 77

```
<212> TYPE: RNA
<213> ORGANISM: Escherichia coli
<220> FEATURE:
<221> NAME/KEY: modified_base
<222> LOCATION: (38)..(38)
<223> OTHER INFORMATION: g=m1g
<220> FEATURE:
<221> NAME/KEY: modified_base
<222> LOCATION: (47)..(47)
<223> OTHER INFORMATION: g=m7g
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 225
cggugauugg cgcagccugg nagcgcacuu cguucgggac gaaggggucg gagguncgaa      60
uccucuauca ccgacca                                                    77

<210> SEQ ID NO 226
<211> LENGTH: 89
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (18)..(18)
<223> OTHER INFORMATION: n=d
<220> FEATURE:
<221> NAME/KEY: modified_base
<222> LOCATION: (36)..(36)
<223> OTHER INFORMATION: a=i6a
<220> FEATURE:
<221> NAME/KEY: modified_base
<222> LOCATION: (68)..(68)
<223> OTHER INFORMATION: u=m5u
<220> FEATURE:
<221> NAME/KEY: modified_base
<222> LOCATION: (69)..(69)
<223> OTHER INFORMATION: n=p
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u

<400> SEQUENCE: 226
aagaucgucg ucuccggnga ggcggcugga cuucaaaucc aguuggggcc gcgcgguccc      60
gggcaggunc gacuccugug aucuugcca                                       89

<210> SEQ ID NO 227
<211> LENGTH: 88
<212> TYPE: RNA
<213> ORGANISM: Escherichia coli
<220> FEATURE:
```

```
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (17)..(17)
<223> OTHER INFORMATION: g=gm
<220> FEATURE:
<221> NAME/KEY: modified_base
<222> LOCATION: (43)..(43)
<223> OTHER INFORMATION: c=cm
<220> FEATURE:
<221> NAME/KEY: modified_base
<222> LOCATION: (45)..(45)
<223> OTHER INFORMATION: u=cmo5u
<220> FEATURE:
<221> NAME/KEY: modified_base
<222> LOCATION: (48)..(48)
<223> OTHER INFORMATION: a=ms2i6a
<220> FEATURE:
<221> NAME/KEY: modified_base
<222> LOCATION: (66)..(66)
<223> OTHER INFORMATION: u=m5u
<220> FEATURE:
<221> NAME/KEY: modified_base
<222> LOCATION: (67)..(67)
<223> OTHER INFORMATION: n=p
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (67)..(67)
<223> OTHER INFORMATION: n is a, c, g, t or u

<400> SEQUENCE: 227
ggaagugugg ccgagcggnn gaaggcaccg gucuugaaaa ccggcgaccc gaaaggguuc    60
cagaguncga aucucugcgc uuccgcca                                      88

<210> SEQ ID NO 228
<211> LENGTH: 90
<212> TYPE: RNA
<213> ORGANISM: Escherichia coli
<220> FEATURE:
<221> NAME/KEY: modified_base
<222> LOCATION: (17)..(17)
<223> OTHER INFORMATION: g=gm
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (38)..(38)
<223> OTHER INFORMATION: a=ms2i6a
<220> FEATURE:
<221> NAME/KEY: modified_base
<222> LOCATION: (68)..(68)
<223> OTHER INFORMATION: u=m5u
<220> FEATURE:
<221> NAME/KEY: modified_base
<222> LOCATION: (69)..(69)
<223> OTHER INFORMATION: n=p
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
```

<400> SEQUENCE: 228
ggagagaugc cggagcggcn gaacggaccg gucucgaaaa ccggaguagg ggcaacucua    60
ccgggggunc aaaucccccu cucuccgcca                                    90

<210> SEQ ID NO 229
<211> LENGTH: 93
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (33)..(33)
<223> OTHER INFORMATION: c=s2c
<220> FEATURE:
<221> NAME/KEY: modified_base
<222> LOCATION: (38)..(38)
<223> OTHER INFORMATION: a=t6a
<220> FEATURE:
<221> NAME/KEY: modified_base
<222> LOCATION: (71)..(71)
<223> OTHER INFORMATION: u=m5u
<220> FEATURE:
<221> NAME/KEY: modified_base
<222> LOCATION: (72)..(72)
<223> OTHER INFORMATION: n=p
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (72)..(72)
<223> OTHER INFORMATION: n is a, c, g, t or u

<400> SEQUENCE: 229
ggugaggugg ccgagaggcn gaaggcgcuc cccugcuaag ggaguaugcg gucaaaagcu    60
gcauccgggg uncgaauccc cgccucaccg cca                                93

<210> SEQ ID NO 230
<211> LENGTH: 88
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (17)..(17)
<223> OTHER INFORMATION: g=gm
<220> FEATURE:
<221> NAME/KEY: modified_base
<222> LOCATION: (19)..(20)
<223> OTHER INFORMATION: n=d
<220> FEATURE:
<221> NAME/KEY: modified_base
<222> LOCATION: (41)..(41)
<223> OTHER INFORMATION: n=p
<220> FEATURE:
<221> NAME/KEY: modified_base
<222> LOCATION: (66)..(66)
<223> OTHER INFORMATION: u=m5u
<220> FEATURE:
<221> NAME/KEY: modified_base
<222> LOCATION: (67)..(67)

```
<223> OTHER INFORMATION: n=p
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (67)..(67)
<223> OTHER INFORMATION: n is a, c, g, t or u

<400> SEQUENCE: 230
ggugaggugu ccgaguggnn gaaggagcac gccuggaaag nguguauacg gcaacguauc    60 gggggguncga aucccccccu caccgcca                                     88

<210> SEQ ID NO 231
<211> LENGTH: 88
<212> TYPE: RNA
<213> ORGANISM: Escherichia coli
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (41)..(41)
<223> OTHER INFORMATION: n=p
<220> FEATURE:
<221> NAME/KEY: modified_base
<222> LOCATION: (66)..(66)
<223> OTHER INFORMATION: u=m5u
<220> FEATURE:
<221> NAME/KEY: modified_base
<222> LOCATION: (67)..(67)
<223> OTHER INFORMATION: n=p
<220> FEATURE:
<221> NAME/KEY: modified_base
<222> LOCATION: (17)..(17)
<223> OTHER INFORMATION: g=gm
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (67)..(67)
<223> OTHER INFORMATION: n is a, c, g, t or u

<400> SEQUENCE: 231
ggugaggugu ccgaguggcn gaaggagcac gccuggaaag nguguauacg gcaacguauc    60
ggggguncga aucccccccu caccgcca                                      88

<210> SEQ ID NO 232
<211> LENGTH: 76
<212> TYPE: RNA
<213> ORGANISM: Escherichia coli
<220> FEATURE:
<221> NAME/KEY: modified_base
<222> LOCATION: (16)..(17)
<223> OTHER INFORMATION: n=d
<220> FEATURE:
<221> NAME/KEY: modified_base
```

```
<222> LOCATION: (20)..(20)
<223> OTHER INFORMATION: n=d
<220> FEATURE:
<221> NAME/KEY: modified_base
<222> LOCATION: (37)..(37)
<223> OTHER INFORMATION: a=m6t6a
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 232
gcugauaugg cucagnnggn agagcgcacc cuugguaagg gugagguccc caguncgacu     60
cuggguauca gcacca                                                    76

<210> SEQ ID NO 233
<211> LENGTH: 76
<212> TYPE: RNA
<213> ORGANISM: Escherichia coli
<220> FEATURE:
<221> NAME/KEY: modified_base
<222> LOCATION: (16)..(17)
<223> OTHER INFORMATION: n=d
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (37)..(37)
<223> OTHER INFORMATION: a=m6t6a
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
```

```
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 233
gcugauauag cucagnnggn agagcgcacc cuugguaagg gugaggucgg caguncgaau     60
cugccuauca gcacca                                                    76

<210> SEQ ID NO 234
<211> LENGTH: 76
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(17)
<223> OTHER INFORMATION: n=d
<220> FEATURE:
<221> NAME/KEY: modified_base
<222> LOCATION: (20)..(20)
<223> OTHER INFORMATION: n=d
<220> FEATURE:
<221> NAME/KEY: modified_base
<222> LOCATION: (32)..(32)
<223> OTHER INFORMATION: c=cm
<220> FEATURE:
<221> NAME/KEY: modified_base
<222> LOCATION: (37)..(37)
<223> OTHER INFORMATION: a=ms2i6a
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u

<400> SEQUENCE: 234
aggggcguag uucaannggn agagcaccgg ucuccaaaac cgggguguugg gaguncgagu    60 cucuccgccc cugcca                                                    76

<210> SEQ ID NO 235
<211> LENGTH: 85
<212> TYPE: RNA
<213> ORGANISM: Escherichia coli
```

```
<220> FEATURE:
<221> NAME/KEY: modified_base
<222> LOCATION: (8)..(9)
<223> OTHER INFORMATION: u=s4u
<220> FEATURE:
<221> NAME/KEY: modified_base
<222> LOCATION: (17)..(17)
<223> OTHER INFORMATION: g=gm
<220> FEATURE:
<221> NAME/KEY: modified_base
<222> LOCATION: (35)..(35)
<223> OTHER INFORMATION: n=q
<220> FEATURE:
<221> NAME/KEY: modified_base
<222> LOCATION: (38)..(38)
<223> OTHER INFORMATION: a=ms2i6a
<220> FEATURE:
<221> NAME/KEY: modified_base
<222> LOCATION: (40)..(40)
<223> OTHER INFORMATION: n=p
<220> FEATURE:
<221> NAME/KEY: modified_base
<222> LOCATION: (63)..(63)
<223> OTHER INFORMATION: u=m5u
<220> FEATURE:
<221> NAME/KEY: modified_base
<222> LOCATION: (64)..(64)
<223> OTHER INFORMATION: n=p
<220> FEATURE:
<221> NAME/KEY: misc_feature
<222> LOCATION: (35)..(35)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u

<400> SEQUENCE: 235
ggugggguuc ccgagcggcc aaagggagca gacunuaaan cugccgucau cgacuucgaa    60
gguncgaauc cuuccccac cacca                                            85

<210> SEQ ID NO 236
<211> LENGTH: 85
<212> TYPE: RNA
<213> ORGANISM: Escherichia coli
<220> FEATURE:
<221> NAME/KEY: modified_base
<222> LOCATION: (8)..(9)
<223> OTHER INFORMATION: u=s4u
<220> FEATURE:
<221> NAME/KEY: modified_base
<222> LOCATION: (17)..(17)
<223> OTHER INFORMATION: g=gm
<220> FEATURE:
<221> NAME/KEY: modified_base
<222> LOCATION: (35)..(35)
<223> OTHER INFORMATION: n=q
<220> FEATURE:
<221> NAME/KEY: modified_base
<222> LOCATION: (38)..(38)
<223> OTHER INFORMATION: a=ms2i6a
<220> FEATURE:
<221> NAME/KEY: modified_base
<222> LOCATION: (40)..(40)
<223> OTHER INFORMATION: n=p
<220> FEATURE:
<221> NAME/KEY: modified_base
<222> LOCATION: (63)..(63)
<223> OTHER INFORMATION: u=m5u
<220> FEATURE:
<221> NAME/KEY: modified_base
<222> LOCATION: (64)..(64)
```

```
<223> OTHER INFORMATION: n=p
<220> FEATURE:
<221> NAME/KEY: misc_feature
<222> LOCATION: (35)..(35)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u

<400> SEQUENCE: 236 gguggguuc ccgagcggcc aaagggagca gacunuaaan cugccgucac agacuucgaa      60
gguncgaauc cuuccccac cacca                                           85

<210> SEQ ID NO 237
<211> LENGTH: 76
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (34)..(34)
<223> OTHER INFORMATION: u=cmo5u
<220> FEATURE:
<221> NAME/KEY: modified_base
<222> LOCATION: (37)..(37)
<223> OTHER INFORMATION: a=m6a
<220> FEATURE:
<221> NAME/KEY: modified_base
<222> LOCATION: (46)..(46)
<223> OTHER INFORMATION: g=m7g
<220> FEATURE:
<221> NAME/KEY: modified_base
<222> LOCATION: (54)..(54)
<223> OTHER INFORMATION: u=m5u
<220> FEATURE:
<221> NAME/KEY: modified_base
<222> LOCATION: (55)..(55)
<223> OTHER INFORMATION: n=p
<220> FEATURE:
<221> NAME/KEY: misc_feature
<222> LOCATION: (55)..(55)
<223> OTHER INFORMATION: n is a, c, g, t or u

<400> SEQUENCE: 237
gggugauuag cucagcdggg agagcaccuc ccuuacaagg aggggucgg cgguncgauc       60 ccgucaucac ccacca                                                    76

<210> SEQ ID NO 238
<211> LENGTH: 77
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(17)
<223> OTHER INFORMATION: n=d
<220> FEATURE:
<221> NAME/KEY: modified_base
<222> LOCATION: (20)..(21)
<223> OTHER INFORMATION: n=d
<220> FEATURE:
<221> NAME/KEY: modified_base
```

```
<222> LOCATION: (47)..(47)
<223> OTHER INFORMATION: g=m7g
<220> FEATURE:
<221> NAME/KEY: modified_base
<222> LOCATION: (48)..(48)
<223> OTHER INFORMATION: u=acp3u
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 238
gcguccguag cucagnnggn nagagcacca ccuugacaug guggggucg gugguncgag      60 uccacucgga cgcacca                                                   77

<210> SEQ ID NO 239
<211> LENGTH: 77
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (16)..(17)
<223> OTHER INFORMATION: n=d
<220> FEATURE:
<221> NAME/KEY: modified_base
<222> LOCATION: (20)..(21)
<223> OTHER INFORMATION: n=d
<220> FEATURE:
<221> NAME/KEY: modified_base
<222> LOCATION: (47)..(47)
<223> OTHER INFORMATION: g=m7g
<220> FEATURE:
<221> NAME/KEY: modified_base
<222> LOCATION: (48)..(48)
<223> OTHER INFORMATION: u=acp3u
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: misc_feature
<222> LOCATION: (16)..(16)
<223> OTHER INFORMATION: n is a, c, g, t or u
<220> FEATURE:
```

-continued

```
<221> NAME/KEY: misc_feature
<222> LOCATION: (17)..(17)
<223> OTHER INFORMATION: n is a, c, g, t or u
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 239
gcguucauag cucagnnggn nagagcacca ccuugacaug ggggggucg uugguncgag    60 uccaauugaa cgcacca                                                 77

<210> SEQ ID NO 240
<211> LENGTH: 77
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (21)..(21)
<223> OTHER INFORMATION: n=d
<220> FEATURE:
<221> NAME/KEY: modified_base
<222> LOCATION: (33)..(33)
<223> OTHER INFORMATION: c=cm
<220> FEATURE:
<221> NAME/KEY: modified_base
<222> LOCATION: (47)..(47)
<223> OTHER INFORMATION: g=m7g
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 240 cgcgggugg agcagccugg nagcucgucg ggcucauaac ccgaaggucg ucgguncaaa    60
uccggccccc gcaacca                                                 77

<210> SEQ ID NO 241
<211> LENGTH: 77
<212> TYPE: RNA
<213> ORGANISM: Escherichia coli
<220> FEATURE:
<221> NAME/KEY: modified_base
<222> LOCATION: (8)..(8)
<223> OTHER INFORMATION: u=s4u
<220> FEATURE:
<221> NAME/KEY: modified_base
<222> LOCATION: (21)..(21)
<223> OTHER INFORMATION: n=d
```

```
<220> FEATURE:
<221> NAME/KEY: modified_base
<222> LOCATION: (33)..(33)
<223> OTHER INFORMATION: c=cm
<220> FEATURE:
<221> NAME/KEY: modified_base
<222> LOCATION: (55)..(55)
<223> OTHER INFORMATION: u=m5u
<220> FEATURE:
<221> NAME/KEY: modified_base
<222> LOCATION: (56)..(56)
<223> OTHER INFORMATION: n=p
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 241 cgcgggugg agcagccugg nagcucgucg ggcucauaac ccgaagaucg ucgguncaaa     60
uccggccccc gcaacca                                                   77

<210> SEQ ID NO 242
<211> LENGTH: 15
<212> TYPE: RNA
<213> ORGANISM: Escherichia coli
<220> FEATURE:
<221> NAME/KEY: modified_base
<222> LOCATION: (10)..(10)
<223> OTHER INFORMATION: u=cmo5u
<220> FEATURE:
<221> NAME/KEY: modified_base
<222> LOCATION: (13)..(13)
<223> OTHER INFORMATION: a=m6a

<400> SEQUENCE: 242
caccucccuu acaag                                                     15

<210> SEQ ID NO 243
<211> LENGTH: 13
<212> TYPE: RNA
<213> ORGANISM: Escherichia coli

<400> SEQUENCE: 243
ucaucaccca cca                                                       13

<210> SEQ ID NO 244
<211> LENGTH: 12
<212> TYPE: RNA
<213> ORGANISM: Escherichia coli

<400> SEQUENCE: 244
uccccccccu cg                                                        12
```